United States Patent
Li et al.

(10) Patent No.: US 12,024,503 B2
(45) Date of Patent: Jul. 2, 2024

(54) BENZETHERS AND ANILINES OF PYRAZOLYL-AMINO-PYRIMIDINYL DERIVATIVES, AND COMPOSITIONS AND METHODS THEREOF

(71) Applicant: LYNK PHARMACEUTICALS CO. LTD., Hangzhou (CN)

(72) Inventors: Xiaodong Li, Hangzhou (CN); Michael Lawrence Vazquez, Creve Coeur, MO (US); Zhaokui Wan, Hangzhou (CN)

(73) Assignee: LYNK PHARMACEUTICALS CO. LTD., Hangzhou (CN)

( * ) Notice: Subject to any disclaimer, the term of this patent is extended or adjusted under 35 U.S.C. 154(b) by 0 days.

(21) Appl. No.: 18/377,741

(22) Filed: Oct. 6, 2023

(65) Prior Publication Data

US 2024/0083882 A1     Mar. 14, 2024

Related U.S. Application Data

(63) Continuation of application No. 17/437,989, filed as application No. PCT/CN2020/083779 on Apr. 8, 2020.

(30) Foreign Application Priority Data

Apr. 8, 2019  (WO) ............... PCT/CN2019/081742

(51) Int. Cl.
C07D 403/12    (2006.01)
C07D 401/14    (2006.01)
C07D 405/14    (2006.01)

(52) U.S. Cl.
CPC ......... C07D 403/12 (2013.01); C07D 401/14 (2013.01); C07D 405/14 (2013.01)

(58) Field of Classification Search
CPC ... C07D 401/14; C07D 403/12; C07D 405/14
See application file for complete search history.

(56) References Cited

U.S. PATENT DOCUMENTS 9,682,941 B2 *   6/2017  Auvin ................. C07D 401/06
2022/0259182 A1 *  8/2022  Li ....................... C07D 401/14

FOREIGN PATENT DOCUMENTS

| | | |
|---|---|---|
| WO | 2012062704 A1 | 5/2012 |
| WO | 2012142329 A1 | 10/2012 |
| WO | 2013034238 A1 | 3/2013 |
| WO | 2014128486 A1 | 8/2014 |

OTHER PUBLICATIONS

Baba, J Med Chem, 1996, vol. 39, 5176-5182. (Year: 1996).*
PCT/CN2020/083779, Int'l Search Report & Written Opinion of ISA, dated Jan. 7, 2020.
PCT/CN2019/081742, Int'l Search Report & Written Opinion of ISA, dated Jul. 2, 2020.

* cited by examiner

*Primary Examiner* — D Margaret M Seaman
(74) *Attorney, Agent, or Firm* — Milstein Zhang & Wu LLC

(57) ABSTRACT

Provided is a novel class of orally and/or topically available, selective and potent JAK inhibitors as safe and effective therapeutics against various diseases and disorders. Also provided is pharmaceutical composition of these compounds and methods of a their preparation and use thereof.

13 Claims, No Drawings

BENZETHERS AND ANILINES OF PYRAZOLYL-AMINO-PYRIMIDINYL DERIVATIVES, AND COMPOSITIONS AND METHODS THEREOF

PRIORITY CLAIMS AND RELATED PATENT APPLICATIONS

This application claims the benefit of priority to and is a continuation of U.S. Ser. No. 17/437,989, filed Sep. 10, 2021, which is the U.S. national phase of and claims priority to PCT/CN2020/083779, filed Apr. 8, 2020, which claims the benefit of priority to PCT/CN2019/081742, filed on Apr. 8, 2019, the entire content of each of which is incorporated herein by reference.

TECHNICAL FIELDS OF THE INVENTION

The invention generally relates to novel compounds and methods for their therapeutic use. More particularly, the invention relates to a novel class of therapeutics that are safe and effective JAK inhibitors. The invention also relates to pharmaceutical compositions of these compounds and methods of preparation and use thereof against various diseases and disorders.

BACKGROUND OF THE INVENTION

Janus kinase (JAK) is a family of intracellular, nonreceptor tyrosine kinases that transduce cytokine-mediated signals via the Janus kinase—Signal Transduction Activators of Transcription (JAK-STAT) pathway. There are four members in the JAK family of enzymes in humans, i.e., JAK1, JAK2, JAK3 and TYK2. The family is defined by the presence of two adjacent kinase domains, JH1 and JH2, of which JH1 performs the phosphorylation involved in pathway activation whereas JH2 regulates JH1 function. (Thomas, et al., 2015 *British Journal of Cancer* 113, 365-371.)

These cytoplasmic tyrosine kinases are associated with membrane cytokine receptors such as common gamma-chain receptors and the glycoprotein 130 (gp130) transmembrane proteins. (Murray, et al. 2007 *Immunol.* 178(5):2623-2629.) About 40 cytokine receptors signal through combinations of these four JAKs and their 7 downstream substrates: the STAT family members. (Ghoreschi et al. 2009 *Immunol Rev.* 228(1):273-287.)

The JAK-STAT signaling pathway plays a major role in many fundamental biological processes, such as apoptosis and inflammation via communication of chemical signals outside of a cell to the cell nucleus, resulting in the activation of genes through transcription. A dysfunctional JAK-STAT pathway may lead to a number of diseases, such as cancer and diseases affecting the immune system.

There has been a growing interest in JAK inhibitors as medication to inhibit the activity of one or more members of the JAK family, thereby interfering with the JAK-STAT signaling pathway. Some JAK inhibitors have been shown to have therapeutic benefits in treating cancer or inflammatory diseases such as rheumatoid arthritis. (Kontzias, et al. 2012 *Current Opinion in Pharmacology* 12 (4): 464-70; Pesu, et al. 2008 *Immunological Reviews* 223: 132-42; Norman 2014 Expert Opinion on Investigational Drugs 23 (8): 1067-77; Forster, et al. 2017 Bioorganic & Medicinal Chemistry Letters 27 (18): 4229-4237.)

Development of JAK inhibitors for the treatment of cancer with low susceptibility to drug resistance remains challenging but necessary for improving the long-term effectiveness of this class of drugs. An urgent need exists across broad therapeutic areas for JAK inhibitors with improved potency and minimal side effects that are also less susceptible to or can overcome drug resistance than existing therapeutics.

SUMMARY OF THE INVENTION

The invention provides novel, selective and potent compounds that are orally and/or topically available and/or suitable for gastrointestinal (GI) tract restricted and/or topical administration. These therapeutic agents are safe and effective JAK inhibitors and may exhibit fewer and/or lesser side effects than currently available drugs. The invention also provides pharmaceutical compositions of these compounds and methods of their preparation and use.

Disclosed herein are a series of novel JAK inhibitors that were specifically designed to fit in the profiles that are potentially suitable for either (I) oral administrations or (II) GI and/or skin topical uses. For compounds designed for oral administration, they are potent for JAK2 with an array of selectivity against other JAK kinases and with good overall drug profiles. For the compounds that are potentially suitable for GI restricted or skin topical uses, they are designed to show strong pan JAK activities including JAK1 and/or TYK2. In particular, these compounds are designed to show minimum oral absorption to limit systemic exposure but high exposure at site of action, in particular in the gastric intestine.

This new class of inhibitors exhibits exceptional potency profiles with JAK2 IC50 values in the low nanomolar range at Km ATP concentration. Some of these compounds also showed exceptional potency against JAK1 and/or TYK2.

In one aspect, the invention generally relates to a compound having the structural formula (I):

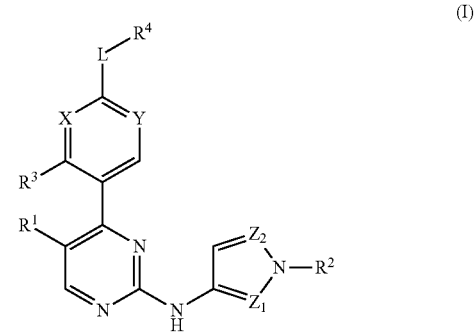

(I)

wherein
L is O or $NR^4$
X is N or $CR^X$, wherein $R^x$ is R', halogen (e.g., Cl, F), CN or OR';
Y is N or $CR^Y$, wherein $R^Y$ is R', halogen (e.g., Cl, F), CN or OR';
each of $Z_i$ and $Z_2$ is independently selected from N and CR', provided that one of $Z_i$ and $Z_2$ is N and the other is CR';
$R^1$ is hydrogen, halogen, CN, $C_1$-$C_6$ (e.g., $C_1$-$C_3$) unsubstituted or substituted alkyl or OR';
$R^2$ is a $C_1$-$C_{16}$ (e.g., Ci-Ce, $C_7$-$Ci_6$) aliphatic group optionally comprising one or more heteroatoms selected from N, O, S and P, wherein the aliphatic group is optionally substituted with one or more of halogen, OR', NRR', CN, CONRR', NRCOR' and $C_1$-$C_6$ (e.g., $C_1$-$C_3$) alkyl, which is in turn optionally substituted with F(e.g., $CH_2F$, $CHF_2$, or $CF_3$), OR' or NRR';

$R^3$ is R' or halogen;

each of $R^4$ and $R^{4'}$, when L is $NR^{4'}$, is selected from hydrogen and $C_1$-$C_{16}$ (e.g., Ci-G, $C_7$-$C_{16}$) aliphatic groups optionally comprising one or more heteroatoms selected from N, O, S and P, and $R^4$ and $R^{4'}$ together may form a 3- to 7-membered ring, having 0 to 3 heteroatoms selected from O, N and S, and wherein each of $R^4$ and $R^{4'}$ is optionally substituted with CN, $CF_3$ or OR'; provided that if one of $R^4$ and $R^{4'}$ is hydrogen, the other is not hydrogen; and each R and R' is independently hydrogen or a $C_1$-$C_{12}$ unsubstituted or substituted alkyl group, or a pharmaceutically acceptable form or an isotope derivative thereof.

In another aspect, the invention generally relates to a pharmaceutical composition comprising a compound disclosed herein, effective to treat or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula (I):

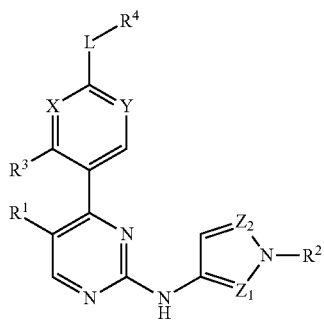

(I)

wherein
L is O or $NR^{4'}$;
X is N or $CR^X$, wherein $R^x$ is R', halogen (e.g., Cl, F), CN or OR';
Y is N or $CR^Y$, wherein $R^Y$ is R', halogen (e.g., Cl, F), CN or OR';
each of Zi and $Z_2$ is independently selected from N and CR', provided that one of Zi and $Z_2$ is N and the other is CR';
$R^1$ is hydrogen, halogen, CN, $C_1$-Ce (e.g., $C_1$-$C_3$) unsubstituted or substituted alkyl or $OR^1$;
$R^2$ is a $C_1$-$C_{16}$ (e.g., Ci-Ce, $C_7$-$Ci_6$) aliphatic group optionally comprising one or more heteroatoms selected from N, O, S and P, wherein the aliphatic group is optionally substituted with one or more of halogen, OR', NRR', CN, CONRR', NRCOR' and $C_1$-$C_6$ (e.g., $C_1$-$C_3$) alkyl, which is in turn optionally substituted with F(e.g., $CH_2F$, $CHF_2$, or $CF_3$), OR' or NRR';
$R^3$ is R' or halogen;
each of $R^4$ and $R^{4'}$, when L is $NR^{4'}$, is selected from hydrogen and $C_1$-$C_{16}$ (e.g., Ci-G, $C_7$-$C_{16}$) aliphatic groups optionally comprising one or more heteroatoms selected from N, O, S and P, and $R^4$ and $R^{4'}$ together may form a 3- to 7-membered ring, having 0 to 3 heteroatoms selected from O, N and S, and wherein each of $R_4$ and $R_4'$ is optionally substituted with CN, CF3 or OR'; provided that if one of $R_4$ and $R_4'$ is hydrogen, the other is not hydrogen; and each R and R' is independently hydrogen or a $C_1$-$C_{12}$ unsubstituted or substituted alkyl group, or a pharmaceutically acceptable form or an isotope derivative thereof, effective to treat, or reduce one or more diseases or disorders, in a mammal, including a human, and a pharmaceutically acceptable excipient, carrier, or diluent.

In yet another aspect, the invention generally relates to a unit dosage form comprising a pharmaceutical composition disclosed herein.

In yet another aspect, the invention generally relates to a method for treating or reducing a disease or disorder. The method includes administering to a subject in need thereof a pharmaceutical composition comprising a compound having the structural formula (I):

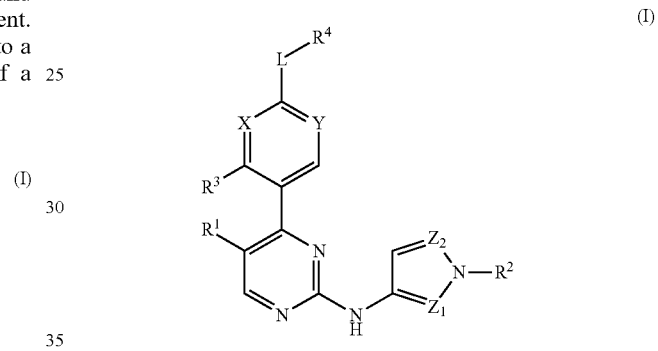

(I)

wherein
L is O or $NR^{4'}$;
X is N or $CR^X$, wherein $R^x$ is R', halogen (e.g., Cl, F), CN or OR';
Y is N or $CR^Y$, wherein $R^Y$ is R', halogen (e.g., Cl, F), CN or OR';
each of Zi and $Z_2$ is independently selected from N and CR', provided that one of Zi and $Z_2$ is N and the other is CR';
$R^1$ is hydrogen, halogen, CN, Ci-Ce (e.g., $C_1$-$C_3$) unsubstituted or substituted alkyl or $OR^1$;
$R^2$ is a $C_1$-$C_{16}$ (e.g., Ci-Ce, $C_7$-$C_{16}$) aliphatic group optionally comprising one or more heteroatoms selected from N, O, S and P, wherein the aliphatic group is optionally substituted with one or more of halogen, OR', NRR', CN, CONRR', NRCOR' and Ci-Ce (e.g., $C_1$-$C_3$) alkyl, which is in turn optionally substituted with F(e.g., $CH_2F$, $CHF_2$, or $CF_3$), OR' or NRR';
$R^3$ is R' or halogen;
each of $R^4$ and $R^{4'}$, when L is $NR^{4'}$, is selected from hydrogen and $C_1$-$C_{16}$ (e.g., Ci-Ce, $C_7$-$C_{16}$) aliphatic groups optionally comprising one or more heteroatoms selected from N, O, S and P, and $R^4$ and $R^{4'}$ together may form a 3- to 7-membered ring, having 0 to 3 heteroatoms selected from O, N and S, and wherein each of $R^4$ and $R^{4'}$ is optionally substituted with CN, CF3 or OR'; provided that if one of $R^4$ and $R^{4'}$ is hydrogen, the other is not hydrogen; and each R and R' is independently hydrogen or a $C_1$-$C_{12}$ unsubstituted or substituted alkyl group, or a pharmaceutically acceptable form or an isotope derivative thereof, effective to treat, prevent, or reduce one or more of inflammatory diseases, immune-mediated diseases, cancer, or a related disease or disorder thereof, in a mammal, including a human, and a pharmaceutically acceptable excipient, carrier, or diluent.

In yet another aspect, the invention generally relates to a method for treating or reducing a disease or disorder. The method includes administering to a subject in need thereof a pharmaceutical composition comprising a compound disclosed herein, wherein the disease or disorder is one or more of inflammatory diseases, immune-mediated diseases and cancer, or a related disease or disorder.

In yet another aspect, the invention generally relates to use of a compound disclosed herein, and a pharmaceutically acceptable excipient, carrier, or diluent, in preparation of a medicament for treating a disease or disorder.

Definitions

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

The following terms, unless indicated otherwise according to the context wherein the terms are found, are intended to have the following meanings.

Ranges provided herein are understood to be shorthand for all of the values within the range. For example, a range of 1 to 16 is understood to include any number, combination of numbers, or sub-range from the group consisting 1, 2, 3, 4, 5, 6, 7, 8, 9, 10, 11, 12, 13, 14, 15 or 16.

As used herein, "at least" a specific value is understood to be that value and all values greater than that value.

Any compositions or methods disclosed herein can be combined with one or more of any of the other compositions and methods provided herein.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

The term "comprising", when used to define compositions and methods, is intended to mean that the compositions and methods include the recited elements, but do not exclude other elements. The term "consisting essentially of", when used to define compositions and methods, shall mean that the compositions and methods include the recited elements and exclude other elements of any essential significance to the compositions and methods. For example, "consisting essentially of" refers to administration of the pharmacologically active agents expressly recited and excludes pharmacologically active agents not expressly recited. The term consisting essentially of does not exclude pharmacologically inactive or inert agents, e.g., pharmaceutically acceptable excipients, carriers or diluents. The term "consisting of", when used to define compositions and methods, shall mean excluding trace elements of other ingredients and substantial method steps. Embodiments defined by each of these transition terms are within the scope of this invention.

Certain compounds of the present invention may exist in particular geometric or stereoisomeric forms. The present invention contemplates all such compounds, including cis- and trans-isomers, atropisomers, R- and ^-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example, "Ci-6 alkyl" is intended to encompass, Ci, C2, C3, C4, C5, Ce, Ci-6, Ci-5, Ci-4, Ci-3, Ci-2, C2-6, C2-5, C2-4, C2-3, C3-6, C3-5, C34, C4-6, C4-5, and C5-6 alkyl.

Where substituent groups are specified by their conventional chemical formulae, written from left to right, they equally encompass the chemically identical substituents that would result from writing the structure from right to left, e.g., —C(=O)—O— is equivalent to —O—C(=O)—.

Structures of compounds of the invention are limited by principles of chemical bonding known to those skilled in the art. Accordingly, where a group may be substituted by one or more of a number of substituents, such substitutions are selected so as to comply with principles of chemical bonding and to give compounds that are not inherently unstable and/or would be known to one of ordinary skill in the art as likely to be unstable under ambient conditions (e.g., aqueous, neutral, and several known physiological conditions).

As used herein, the term "alkyl" refers to a straight or branched hydrocarbon chain radical consisting solely of carbon and hydrogen atoms, containing no unsaturation, having from one to ten carbon atoms (e.g., Ci-10 alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a Ci-6 alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_a$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^3$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each R' is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms (Ci-io) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R_a$, —OC(O)N($R^a$)$_2$, —C(O)N($R^a$)$_2$, —N($R^a$)C(O)OR 1, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., Ce-14 aromatic or Ce-14 aryl) that has at least one ring having a conjugated pi electron system which is carbocyclic (e.g., phenyl, fluorenyl, and naphthyl). In some embodiments, the aryl is a Ce-io aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl (C5), cyclohexyl (C6), cyclohexenyl (C6), cyclohexadienyl (C6) and the like. Examples of $C_{3-7}$ carbocyclyl groups include norbornyl (C). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl (Cs), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N(R)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halogen" refers to fluorine (F), chlorine (Cl), bromine (Br), or iodine (I). As used herein, the term "halide" or "halo", means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroatom" refers to oxygen (O), nitrogen (N), sulfur (S), and phosphorus (P).

As used herein, the term "heteroalkyl" refers to an alkyl radical, which have one or more skeletal chain atoms selected from an atom other than carbon, e.g., oxygen, nitrogen, sulfur, phosphorus or combinations thereof. A numerical range can be given, e.g., C14 heteroalkyl, which refers to the chain length in total, which in this example is 4 atoms long. For example, a —CH$_2$OCH$_2$CH$_3$ radical is referred to as a "C4" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH2CH2OCH3), ethoxymethanyl (—CH2OCH2CH3), (methoxymethoxy)ethanyl (—CH2CH2OCH2OCH3), (methoxymethoxy) methanyl (—CH2OCH2OCH3) and (methoxyethoxy)methanyl (—CH2OCH2CH2OCH3) and the like; amines such as (—CH2CH2NHCH3, —CH$_2$CH$_2$N(CH3)$_2$, —CH2NHCH2CH3, —CH$_2$N(CH$_2$CH3)(CH3)) and the like.

As used herein, the term "heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h] quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo[3,2-c]pyridinyl, 5.6.7.8.9.10-hexahydrocycloocta[d] pyrimidinyl, 5,6,7,8,9,10-hexahydrocycloocta[d]pyridazinyl, 5.6.7.8.9.10-hexahydrocycloocta[d]pyridinyl, isothiazolyl, imidazolyl, indazolyl, indolyl, indazolyl, isoindolyl, indolinyl, isoindobnyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxabnyl, quinolinyl, isoquinolinyl, tetrahydroquinobnyl, 5,6,7,8-tetrahydroquinazobnyl, 5,6,7,8-tetrahydrobenzo[4,5] thieno[2,3-d]pyrimdinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O) N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the term "administering" refers to oral administration, administration as a suppository, topical contact, intravenous, parenteral, intraperitoneal, intramuscular, intralesional, intrathecal, intracranial, inhalation, intraocular, intranasal or subcutaneous administration, or the implantation of a slow-release device, e.g., a mini-osmotic pump, to a subject. Suitable routes of administration for a particular patient will depend on the nature and severity of the disease or condition being treated or the nature of the therapy being used and on the nature of the active compound.

Administration may be by any suitable route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies.

The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, gels, for example, water or water/propylene glycol solutions.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, 1995 *J. Biomater Sci. Polym. Ed.* 7:623-645; as biodegradable and injectable gel formulations (see, e.g., Gao 1995 *Pharm. Res.* 12:857-863); or, as microspheres for oral administration (see, e.g., Eyles 1997 *J. Pharm. Pharmacol.* 49:669-674).

As used herein, the terms "disease," "condition," and "disorder" are used interchangeably herein and refer to a state of being or health status of a patient or subject capable of being treated with a compound, pharmaceutical composition, or method provided herein.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "inhibition," "inhibit" and "inhibiting" and the like in reference to a biological target (e.g., JAKs) inhibitor interaction refers to negatively affecting (e.g., decreasing) the activity or function of the protein relative to the activity or function of the protein in the absence of the inhibitor. In embodiments, inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation).

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high-performance liquid chromatography.

As used herein, a "pharmaceutically acceptable form" of a disclosed compound includes, but is not limited to, pharmaceutically acceptable salts, esters, hydrates, solvates, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof. In some embodiments, a "pharmaceutically acceptable form" includes, but is not limited to, pharmaceutically acceptable isomers and stereoisomers, prodrugs and isotopically labeled derivatives thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchlorate acid or with organic acids such as acetic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, p-toluenesulfonate, undecanoate, valerate salts, and the like. In some embodiments, organic acids from which salts can be derived include, for example, acetic acid, propionic acid, glycolic acid, pyruvic acid, lactic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate." Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in Bioreversible Carriers in Drug Design, ed. Edward B. Roche, American Pharmaceutical Association and Pergamon Press, 1987, both of which are incorporated in full by reference herein.

Prodrug forms often offer advantages of solubility, tissue compatibility, or delayed release in the mammalian organism. (See, Bundgard, Design of Prodrugs, pp. 7-9,21-24, Elsevier, Amsterdam 1985 and Silverman, The Organic Chemistry of Drug Design and Drug Action, pp. 352-401, Academic Press, San Diego, Calif., 1992.) Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having a carbonate, carbamate, amide or alkyl ester moiety covalently bonded to any of the above substituents disclosed herein.

Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. A subject to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), rodents (e.g., rats and/or mice), etc. In certain embodiments, the non-human animal is a mammal. The non-human animal may be a male or female at any stage of development. A non-human animal may be a transgenic animal. Typically, the terms "subject" and "patient" are used interchangeably herein in reference to a human subject.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. Treating or treatment thus refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters, for example, the results of a physical examination, neuropsychiatric exams, and/or a psychiatric evaluation. As compared with an equivalent untreated control, such reduction or degree of amelioration may be at least 5%, 10%, 20%, 40%, 50%, 60%, 80%, 90%, 95%, or 100% as measured by any standard technique.

Treatment methods include administering to a subject a therapeutically effective amount of a compound described herein. The administering step may be a single administration or may include a series of administrations. The length of the treatment period depends on a variety of factors, such as the severity of the condition, the patient's age, the concentration of the compound, the activity of the compositions used in the treatment, or a combination thereof. It will also be appreciated that the effective dosage of an agent used for the treatment may increase or decrease over the course of a particular treatment regime. Changes in dosage may result and become apparent by standard diagnostic assays known in the art. In some instances, chronic administration may be required. For example, the compositions are administered to the subject in an amount and for a duration sufficient to treat the patient.

DETAILED DESCRIPTION OF THE INVENTION

The invention is based on an unexpected discovery of novel, selective and potent compounds that are orally and/or topically available and/or suitable for gastrointestinal (GI) tract restricted administration. A series of novel JAK inhibitors are disclosed herein that have been designed to be potentially suitable for either (I) oral administrations or (II) GI and/or skin topical uses. For compounds designed for oral administration, they are potent for JAK2 with an array of selectivity against other JAK kinases and with good overall drug profiles. For the compounds that are potentially suitable for GI restricted or skin topical uses, they are designed to show strong pan JAK activities including JAK1 and/or TYK2. In particular, these compounds are designed to show minimum oral absorption to limit systemic exposure but high exposure at site of action, in particular in the gastric intestine.

Inhibition of Janus kinases will inevitably inhibit immune function and potentially increase the risk for infections both bacterial and viral. By restricting JAK inhibition to the GI tract, for GI restricted compounds or topically for compounds designed for external use on the skin, the systemic exposure of the compounds is greatly reduced or eliminated thereby preserving immune function. In oncology indications where JAK2 is a driver of the cancer, and inhibition of JAK2 is an appropriate treatment, JAK2 selective inhibitors preserve immune function which is not dependent on JAK2 signaling.

Select compounds of the invention are suitable for oral administrations against cancers. These compounds are designed to show good potency against JAK2 with good oral absorption and good in vivo stability. Additionally, compounds may possess selectivity against other JAK kinases (e.g., JAK1).

Select compounds of the invention are suitable for treating GI diseases with limited systemic exposure after oral administration. These compounds possess good potency against JAK kinases (e.g., JAK1, TYK2 and JAK2) and through limited absorption demonstrate higher exposure at the site of action.

Select compounds of the invention are suitable for the topical skin administration. These compounds show good potency against JAK kinases (e.g., JAK1, TYK2 and JAK2) with limited systemic exposure and higher exposure in the dermis/epidermis and thus at the site of action in the skin.

The invention also provides pharmaceutical compositions of these compounds and methods of preparation and use thereof. The JAK inhibitors disclosed herein exhibited exceptional potency profiles while enjoying favorable pharmacokinetic profiles and drug properties that are suitable for target indications.

In one aspect, the invention generally relates to a compound having the structural formula (I):

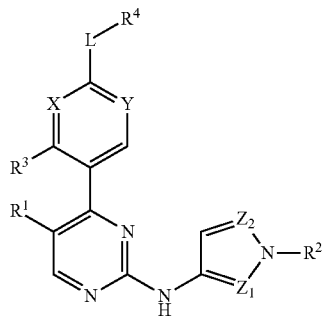

wherein
L is O or $NR^{4'}$;
X is N or $CR^X$, wherein $R^x$ is R', halogen (e.g., Cl, F), CN or OR';
Y is N or $CR^Y$, wherein $R^Y$ is R', halogen (e.g., Cl, F), CN or OR';
each of $Z_i$ and $Z_2$ is independently selected from N and CR', provided that one of $Z_i$ and $Z_2$ is N and the other is CR';
$R^1$ is hydrogen, halogen, CN, $C_1$-$C_6$ (e.g., $C_1$-$C_3$) unsubstituted or substituted alkyl or $OR^1$;
$R^2$ is a $C_1$-$C_{16}$ (e.g., Ci-Ce, $C_7$-$Ci_6$) aliphatic group optionally comprising one or more heteroatoms selected from N, O, S and P, wherein the aliphatic group is optionally substituted with one or more of halogen, OR', NRR', CN, CONRR', NRCOR' and $C_1$-$C_6$ (e.g., $C_1$-$C_3$) alkyl, which is in turn optionally substituted with F(e.g., $CH_2F$, $CHF_2$, or $CF_3$), OR' or NRR';
$R^3$ is R' or halogen;
each of $R^4$ and $R^{4'}$, when L is $NR^{4'}$, is selected from hydrogen and $C_1$-$C_{16}$ (e.g., Ci-G, $C_7$-$C_{16}$) aliphatic groups optionally comprising one or more heteroatoms selected from N, O, S and P, and $R^4$ and $R^{4'}$ together may form a 3- to 7-membered ring, having 0 to 3 heteroatoms selected from O, N and S, and wherein each of $R^4$ and $R^{4'}$ is optionally substituted with CN, $CF_3$ or OR'; provided that if one of $R^4$ and $R^{4'}$ is hydrogen, the other is not hydrogen; and each R and R' is independently hydrogen or a $C_1$-$C_{12}$ unsubstituted or substituted alkyl group, or a pharmaceutically acceptable form or an isotope derivative thereof.

In certain embodiments of (I), L is O having the structural formula:

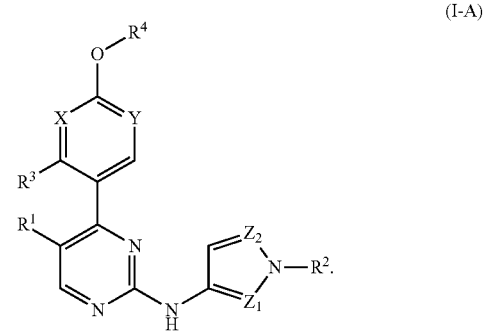

(I-A)

In certain embodiments of (I), L is $NR^{4'}$ having the structural formula:

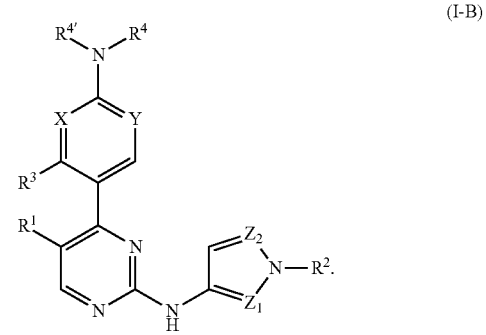

(I-B)

In certain embodiments of (I), X is $CR^X$, wherein $R^x$ is H, halogen, $C_1$-$C_6$ (e.g., $C_1$-$C_3$) unsubstituted or substituted alkyl or alkoxy.

In certain embodiments of (I), X is CH.
In certain embodiments of (I), X is N.
In certain embodiments of (I), Y is $CR^Y$, wherein $R^Y$ is H, halogen, $C_1$-$C_6$ (e.g., $C_1$-$C_3$) unsubstituted or substituted alkyl or alkoxy.

In certain embodiments of (I), Y is CH.
In certain embodiments of (I), Y is N.
In certain embodiments of (I), $Z_1$ is CH and $Z_2$ is N.
In certain embodiments of (I), $Z_1$ is N and $Z_2$ is CH.
In certain embodiments of (I), $R^4$ comprises a linear, branched or cyclic $C_1$-$C_{12}$ (e.g., $C_1$-$C_6$) unsubstituted or substituted alkyl group.

In certain embodiments of (I), $R^4$ comprises a 3- to 7-membered (e.g., 3-, 4- or 5-membered) ring having 0 to 3 (e.g., 0, 1, 2, 3) heteroatoms selected from O, N and S. In certain embodiments of (I), $R^4$ comprises a 3- to 7-membered ring having 0 heteroatoms In certain embodiments of (I), $R^4$ comprises a cyclopropyl ring.

In certain embodiments of (I), $R^4$ comprises a 4-membered ring.

In certain embodiments of (I), $R^4$ comprises a 5-membered ring.

In certain embodiments of (I), $R^4$ is a group that comprises a CN group. In certain embodiments, wherein the CN group is bonded to a carbon atom at β position to L In certain embodiments of (I), the CN group is attached to a secondary carbon atom.

In certain embodiments of (I), the CN group is attached to a tertiary carbon atom.

In certain embodiments of (I), $R^4$ is a $C_3$ alkyl group substituted with CN.

In certain embodiments of (I), $R^4$ is a $C_4$ alkyl group substituted with CN.

In certain embodiments of (I), $R^4$ is a $C_5$ alkyl group substituted with CN.

In certain embodiments of (I), wherein $R^{4'}$ is H.
In certain embodiments of (I), wherein $R^{4'}$ is a $C_1$-$C_3$ alkyl (e.g., methyl, ethyl, propyl). In certain embodiments, wherein $R^{4'}$ is methyl.

In certain embodiments of (I), $R^{4'}$ is methyl.
In certain embodiments of (I), L is O, X is $CR^X$, Y is CH, $Z_1$ is CH and $Z_2$ is N, having the structural formula (II):

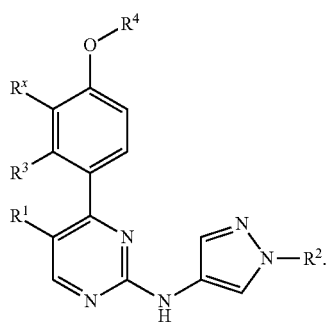

(II)

In certain embodiments of (I), L is $NR^{4'}$, X is $CR^X$, Y is CH, $Z_1$ is CH and $Z_2$ is N, having the structural formula (III):

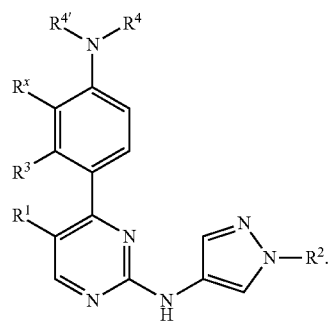

(III)

In certain embodiments of (I), (II) or (III), $R^1$ is F.
In certain embodiments of (I), (II) or (III), $R^1$ is Cl.
In certain embodiments of (I), (II) or (III), $R^1$ is a $C_1$-$C_3$ alkyl (e.g., methyl, ethyl, propyl). In certain embodiments, $R^1$ is methyl.

In certain embodiments of (I), (II) or (III), $R^2$ is a $C_1$-$C_6$ (e.g., $C_1$-$C_3$) aliphatic group with 0 to 2 (e.g., 0, 1 or 2) carbon atoms replaced by one or more heteroatoms selected from N, O, S and P, wherein the aliphatic group is optionally substituted with a CN or $CF_3$ group.

In certain embodiments of (I), (II) or (III), $R^2$ is a $C_7$-$C_{16}$ (e.g., $C_7$-$C_{10}$) aliphatic group with 0 to 3 (e.g., 0, 1, 2 or 3) carbon atoms replaced by one or more heteroatoms selected from N, O, S and P, wherein the aliphatic group is optionally substituted with a CN or $CF_3$ group.

In certain embodiments of (I), (II) or (III), $R^2$ comprises a $C_3$-$C_{16}$ (e.g., $C_3$-$C_{10}$) cyclic alkyl with 0 to 8 (e.g., 0, 1, 2, 3, 4, 5, 6, 7 or 8) carbon atoms replaced by one or more heteroatoms selected from N, O, S and P, optionally substituted with a CN or $CF_3$ group.

In certain embodiments, the cyclic alkyl is a $C_3$-$C_6$ cyclic alkyl.

In certain embodiments, the cyclic alkyl is a $C_3$ cyclic alkyl.

In certain embodiments of (I), (II) or (III), $R^2$ is a group that comprises CN.

In certain embodiments, $R^2$ comprises $CH_2$—CN.
In certain embodiments of (I), (II) or (III), $R^2$ does not comprise CN.

In certain embodiments of (I), (II) or (III), $R^2$ is:

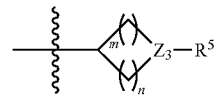

wherein
$Z_3$ is N, CH or O, wherein when $Z_3$ is O, $R^5$ is absent; each of m and n is independently 0, 1, 2, 3 or 4; provided that m and n are not both 0 at the same time, and
$R^5$ is a $C_1$-$C_6$ (e.g., $C_1$-$C_3$) alkyl, CN, halogen or $C(O)R^6$, wherein $R^6$ is a $C_1$-$C_6$ (e.g., $C_1$-$C_3$) alkyl; provided that when $Z_3$ is N, $R^5$ is not CN or halo.

In certain embodiments, each of m and n is 2.
In certain embodiments, $Z_3$ is N.
In certain embodiments, $Z_3$ is O.
In certain embodiments, $R^5$ is a $C_1$-$C_6$ (e.g., $C_1$-$C_3$) alkyl. In certain embodiments, $R^5$ is methyl.

In certain embodiments, $R^5$ is $C(O)R^6$ and $R^6$ is a $C_1$-$C_6$ alkyl, provided at least one of m and n is not 0.

In certain embodiments of (I), (II) or (III), $R^2$ is a substituted or unsubstituted piperidine.

In certain embodiments of (I), (II) or (III), $R^2$ is a substituted or unsubstituted cyclopropyl.

In certain embodiments of (I), (II) or (III), $R^2$ is methyl.

In certain embodiments of (I), (II) or (III), $R^3$ is H.

In certain embodiments of (I), (II) or (III), $R^3$ is CH3.

In certain embodiments of (I), (II) or (III), $R^3$ is F or Cl.

A list of non-limiting examples of the compounds of the invention is provided in Table 1. Certain exemplary data of select compounds are provided in Table 2. Tables 3A and 3B show certain literature compounds and exemplary testing data.

In certain embodiments, a compound of the invention is selected from:

1

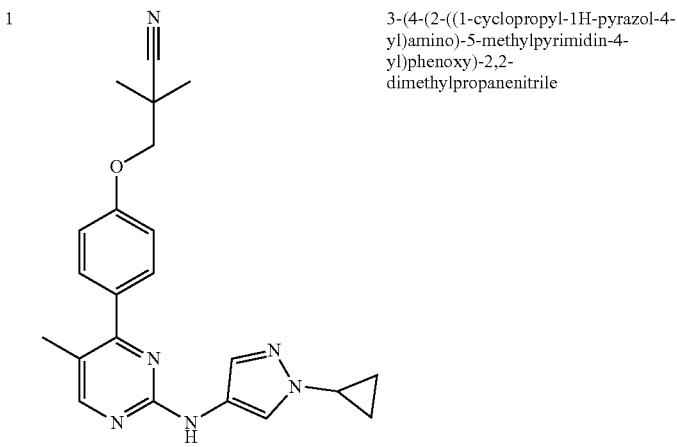

3-(4-(2-((1-cyclopropyl-1H-pyrazol-4-yl)amino)-5-methylpyrimidin-4-yl)phenoxy)-2,2-dimethylpropanenitrile

3

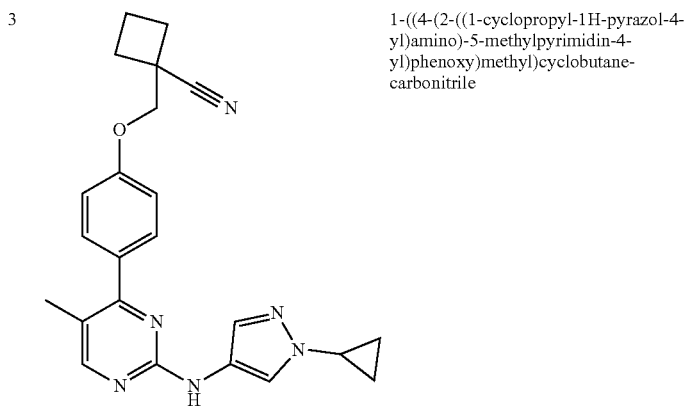

1-((4-(2-((1-cyclopropyl-1H-pyrazol-4-yl)amino)-5-methylpyrimidin-4-yl)phenoxy)methyl)cyclobutane-carbonitrile

12

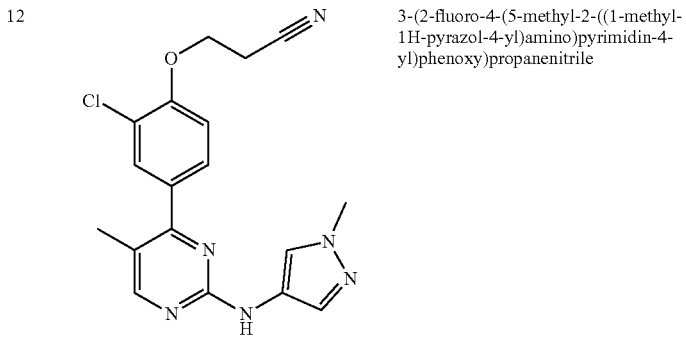

3-(2-fluoro-4-(5-methyl-2-((1-methyl-1H-pyrazol-4-yl)amino)pyrimidin-4-yl)phenoxy)propanenitrile

| | | |
|---|---|---|
| 29 | 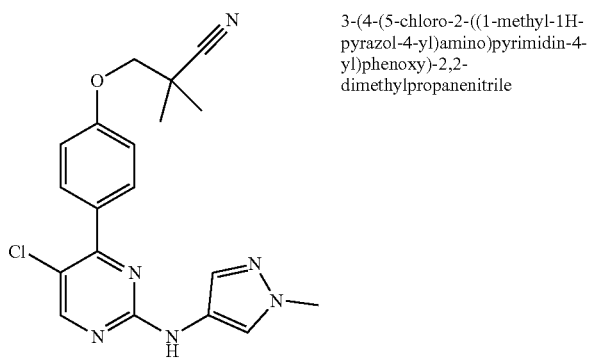 | 3-(4-(5-chloro-2-((1-methyl-1H-pyrazol-4-yl)amino)pyrimidin-4-yl)phenoxy)-2,2-dimethylpropanenitrile |
| 38 | 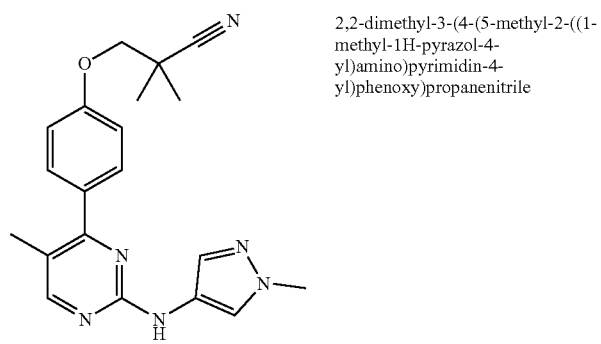 | 2,2-dimethyl-3-(4-(5-methyl-2-((1-methyl-1H-pyrazol-4-yl)amino)pyrimidin-4-yl)phenoxy)propanenitrile |
| 41 | 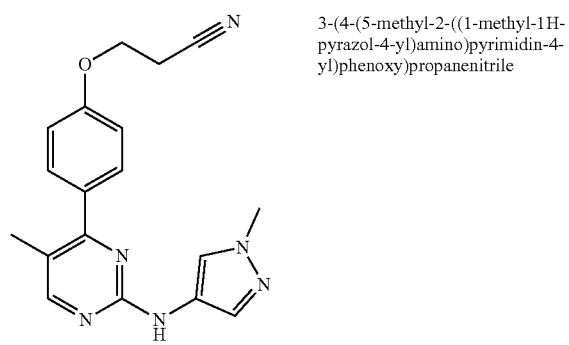 | 3-(4-(5-methyl-2-((1-methyl-1H-pyrazol-4-yl)amino)pyrimidin-4-yl)phenoxy)propanenitrile |
| 42 | 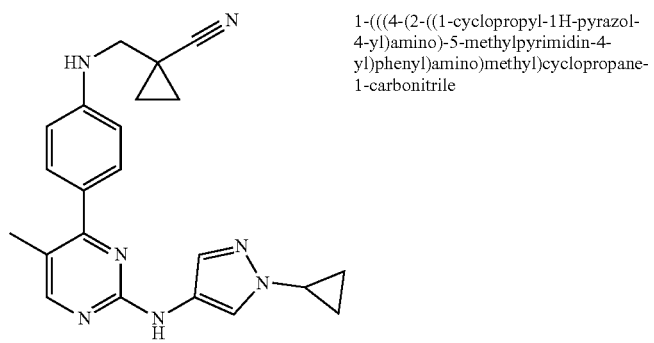 | 1-(((4-(2-((1-cyclopropyl-1H-pyrazol-4-yl)amino)-5-methylpyrimidin-4-yl)phenyl)amino)methyl)cyclopropane-1-carbonitrile |

In certain embodiments, a compound of the invention is selected from:

| Example | Structure | IUPAC name |
|---|---|---|
| 4 | 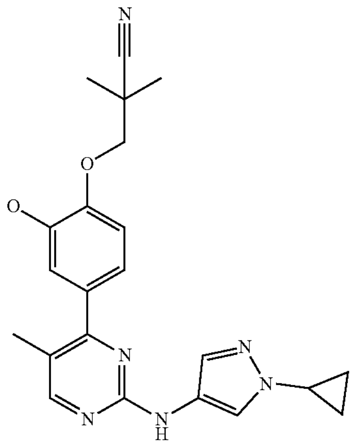 [SMILES: Cc1cnc(Nc2cnn(C3CC3)c2)nc1-c1ccc(OCC(C)(C)C#N)c(O)c1] | 3-(4-(2-((1-cyclopropyl-1H-pyrazol-4-yl)amino)-5-methylpyrimidin-4-yl)-2-fluorophenoxy)-2,2-dimethylpropanenitrile |
| 5 | 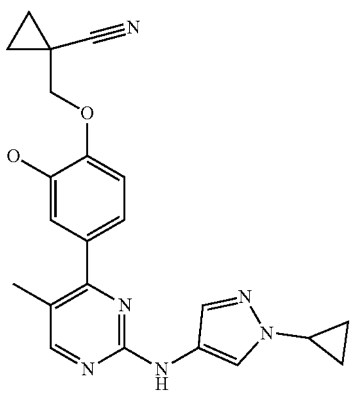 [SMILES: Cc1cnc(Nc2cnn(C3CC3)c2)nc1-c1ccc(OCC2(C#N)CC2)c(O)c1] | 1-((4-(2-((1-cyclopropyl-1H-pyrazol-4-yl)amino)-5-methylpyrimidin-4-yl)-2-fluorophenoxy)methyl)cyclopropane-carbonitrile |
| 6 | 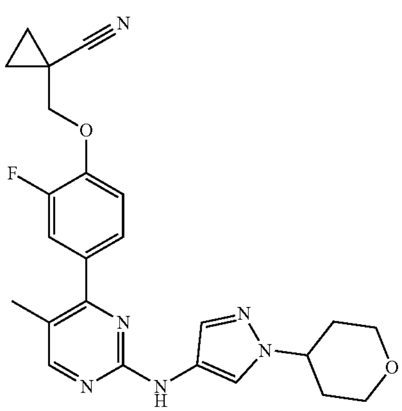 [SMILES: Cc1cnc(Nc2cnn(C3CCOCC3)c2)nc1-c1ccc(OCC2(C#N)CC2)c(F)c1] | 1-((2-fluoro-4-(5-methyl-2-((1-(tetrahydro-2H-pyran-4-yl)-1H-pyrazol-4-yl)amino)pyrimidin-4-yl)phenoxy)methyl)cyclopropane-carbonitrile |

|Example|Structure|IUPAC name|
|---|---|---|
|7| 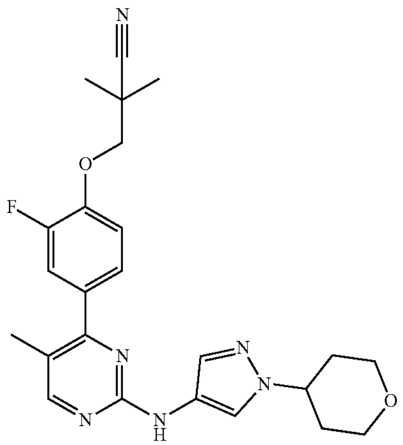 [SMILES: Cc1cnc(Nc2cnn(C3CCOCC3)c2)nc1-c1ccc(OCC(C)(C)C#N)c(F)c1] |3-(2-fluoro-4-(5-methyl-2-((1-(tetrahydro-2H-pyran-4-yl)-1H-pyrazol-4-yl)amino)pyrimidin-4-yl)phenoxy)-2,2-dimethylpropanenitrile|
|13| 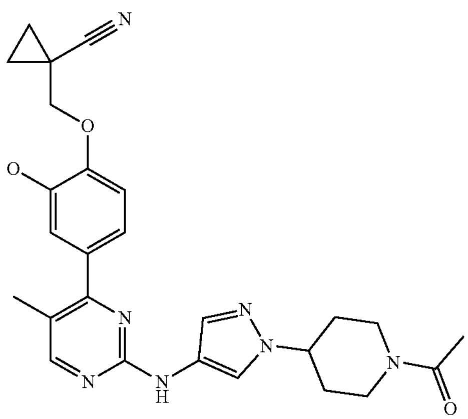 [SMILES: CC(=O)N1CCC(n2cc(Nc3ncc(C)c(-c4ccc(OCC5(C#N)CC5)c(O)c4)n3)cn2)CC1] |1-((4-(2-((1-(1-acetylpiperidin-4-yl)-1H-pyrazol-4-yl)amino)-5-methylpyrimidin-4-yl)-2-fluorophenoxy)methyl)cyclopropane-carbonitrile|
|17| 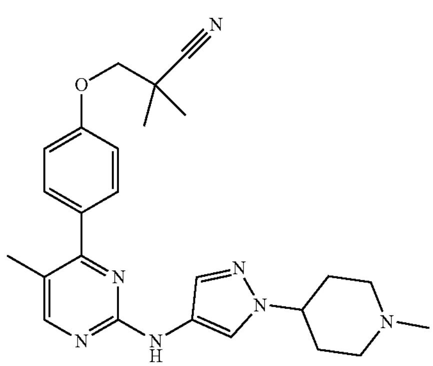 |2,2-dimethyl-3-(4-(5-methyl-2-((1-(1-methylpiperidin-4-yl)-1H-pyrazol-4-yl)amino)pyrimidin-4-yl)phenoxy)propanenitrile|

| Example | Structure | IUPAC name |
|---|---|---|
| 19 | 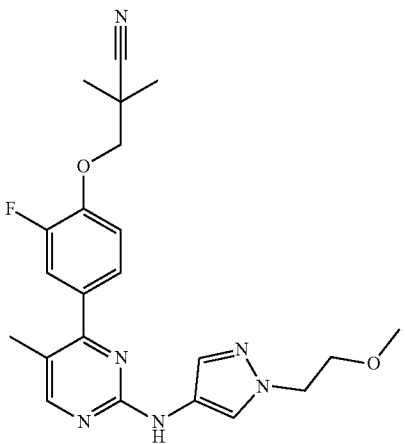 | 3-(2-fluoro-4-(2-((1-(2-methoxyethyl)-1H-pyrazol-4-yl)amino)-5-methylpyrimidin-4-yl)phenoxy)-2,2-dimethylpropanenitrile |
| 20 | 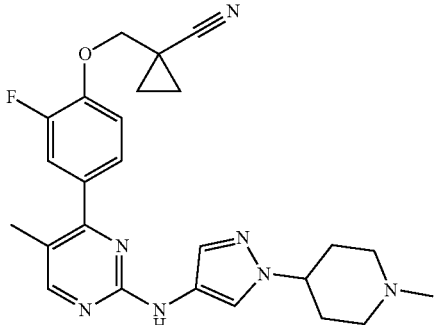 | 1-((2-fluoro-4-(5-methyl-2-((1-(1-methylpiperidin-4-yl)-1H-pyrazol-4-yl)amino)pyrimidin-4-yl)phenoxy)methyl)cyclopropanecarbonitrile |
| 40 | 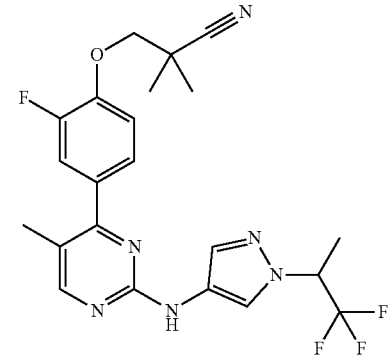 [SMILES: Cc1cnc(Nc2cnn(C(C)C(F)(F)F)c2)nc1-c1ccc(OCC(C)(C)C#N)c(F)c1] | 3-(2-fluoro-4-(5-methyl-2-((1-(1,1,1-trifluoropropan-2-yl)-1H-pyrazol-4-yl)amino)pyrimidin-4-yl)phenoxy)-2,2-dimethylpropanenitrile |

As discussed herein, isotope derivative compounds having one or more hydrogen atoms (e.g., 1, 2, 4, 5, 6, 7, 8, 9, 10, etc.) replaced with deuterium atoms are contemplated in the presented invention. In certain embodiments, isotope derivative compounds of the invention have one hydrogen atom replaced with a deuterium atom.

In another aspect, the invention generally relates to a pharmaceutical composition comprising a compound disclosed herein, effective to treat or reduce one or more diseases or disorders, in a mammal, including a human, and a pharmaceutically acceptable excipient, carrier, or diluent.

In yet another aspect, the invention generally relates to a pharmaceutical composition comprising an amount of a compound having the structural formula (I):

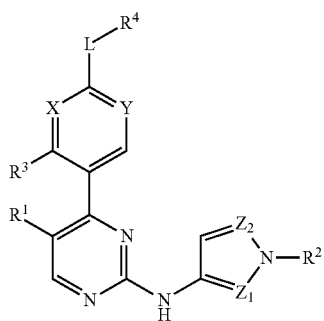

(I)

wherein
L is O or $NR^{4'}$;
X is N or $CR^X$, wherein $R^x$ is R', halogen (e.g., Cl, F), CN or OR';
Y is N or $CR^Y$, wherein $R^Y$ is R', halogen (e.g., Cl, F), CN or OR';
each of $Z_i$ and $Z_2$ is independently selected from N and CR', provided that one of $Z_i$ and $Z_2$ is N and the other is CR';
$R^1$ is hydrogen, halogen, CN, $C_1$-$C_6$ (e.g., $C_1$-$C_3$) unsubstituted or substituted alkyl or $OR^1$;
$R^2$ is a $C_1$-$C_{16}$ (e.g., Ci-Ce, $C_7$-$C_{16}$) aliphatic group optionally comprising one or more heteroatoms selected from N, O, S and P, wherein the aliphatic group is optionally substituted with one or more of halogen, OR', NRR', CN, CONRR', NRCOR' and $C_1$-$C_6$ (e.g., $C_1$-$C_3$) alkyl, which is in turn optionally substituted with F(e.g., CH2F, CHF2, or CF3), OR' or NRR';
$R^3$ is R' or halogen;
each of $R^4$ and $R^{4'}$, when L is $NR^{4'}$, is selected from hydrogen and $C_1$-$C_{16}$ (e.g., Ci-G, $C_7$-$C_{16}$) aliphatic groups optionally comprising one or more heteroatoms selected from N, O, S and P, and $R^4$ and $R^{4'}$ together may form a 3- to 7-membered ring, having 0 to 3 heteroatoms selected from O, N and S, and wherein each of $R^4$ and $R^{4'}$ is optionally substituted with CN, $CF_3$ or OR'; provided that if one of $R^4$ and $R^{4'}$ is hydrogen, the other is not hydrogen; and
each R and R' is independently hydrogen or a $C_1$-$C_{12}$ unsubstituted or substituted alkyl group,
or a pharmaceutically acceptable form or an isotope derivative thereof, effective to treat, or reduce one or more diseases or disorders, in a mammal, including a human, and a pharmaceutically acceptable excipient, carrier, or diluent.

In certain embodiments of the pharmaceutical compositions, L is O, X is $CR^X$, Y is CH, $Z_i$ is CH and $Z_2$ is N, and the compound has the structural formula (II):

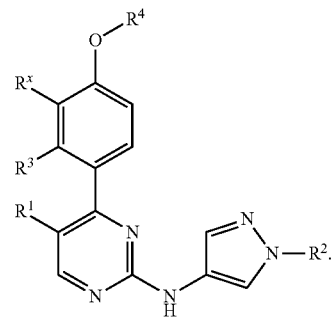

(II)

In certain embodiments of the pharmaceutical compositions, L is $NR^{4'}$, X is $CR^X$, Y is CH, $Z_i$ is CH and $Z_2$ is N, and the compound has the structural formula (II):

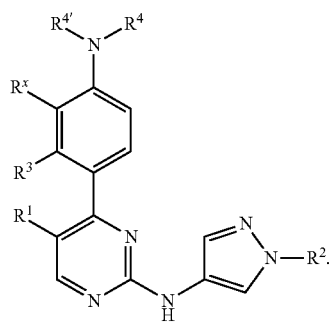

(III)

In certain embodiments of the pharmaceutical compositions, $R^4$ comprises a linear, branched or cyclic $C_1$-$C_{12}$ (e.g., Ci-Ce, $C_7$-$C_{12}$) unsubstituted or substituted alkyl group.

In certain embodiments of the pharmaceutical compositions, $R^4$ comprises a 3- to 7-membered (e.g., 3-, 4- or 5-membered) ring having 0 to 3 (e.g., 0, 1, 2, 3) heteroatoms selected from O, N and S. In certain embodiments of the pharmaceutical compositions, $R^4$ comprises a 3- to 7-membered (e.g., 3-, 4- or 5-membered) ring having 0 heteroatoms.

In certain embodiments, the pharmaceutical composition of the invention is suitable for oral administration.

In certain embodiments, the pharmaceutical composition of the invention is suitable for topical administration.

In certain embodiments, the pharmaceutical composition of the invention is suitable for G1-restricted administration.

In certain embodiments, the pharmaceutical composition of the invention is useful to treat or reduce one or more of inflammatory diseases, immune-mediated diseases and cancers, or a related disease or disorder.

In certain embodiments, the pharmaceutical composition of the invention is useful for treating or reducing an inflammatory disease, or a related disease or disorder.

In certain embodiments, the pharmaceutical composition of the invention is useful for treating or reducing an immune-mediated disease, or a related disease or disorder.

In certain embodiments, the pharmaceutical composition of the invention is useful for treating or reducing cancer, or a related disease or disorder.

In certain embodiments, the pharmaceutical composition of the invention is useful for treating or reducing a disease or disorder selected from: inflammatory bowel disease, psoriasis, vitiligo, alopecia areata, alopecia totalis, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

In yet another aspect, the invention generally relates to a unit dosage form comprising a pharmaceutical composition disclosed herein.

In certain embodiments, the unit dosage form is a solid dosage form, for example, in the forms of capsules, tablets, pills, powders or granules. In certain embodiments, the unit dosage form is a capsule. In certain embodiments, the unit dosage form is a tablet.

In certain embodiments, the unit dosage form is a liquid dosage form, for example, in the forms of emulsions, solutions, suspensions, syrups or elixirs.

In yet another aspect, the invention generally relates to a method for treating or reducing a disease or disorder. The method includes administering to a subject in need thereof a pharmaceutical composition comprising a compound having the structural formula (I):

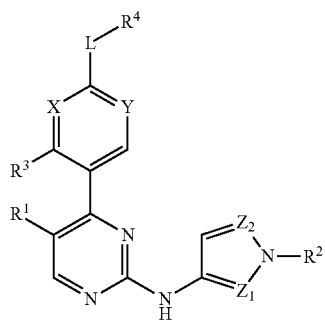

(I)

wherein
L is O or $NR^{4'}$;
X is N or $CR^X$, wherein $R^x$ is R', halogen (e.g., Cl, F), CN or OR';
Y is N or $CR^Y$, wherein $R^Y$ is R', halogen (e.g., Cl, F), CN or OR';
each of Zi and $Z_2$ is independently selected from N and CR', provided that one of Zi and $Z_2$ is N and the other is CR';
$R^1$ is hydrogen, halogen, CN, $C_1$-$C_6$ (e.g., $C_1$-$C_3$) unsubstituted or substituted alkyl or $OR^1$;
$R^2$ is a $C_1$-$C_{16}$ (e.g., Ci-Ce, $C_7$-$Ci_6$) aliphatic group optionally comprising one or more heteroatoms selected from N, O, S and P, wherein the aliphatic group is optionally substituted with one or more of halogen, OR', NRR', CN, CONRR', NRCOR' and $C_1$-$C_6$ (e.g., $C_1$-$C_3$) alkyl, which is in turn optionally substituted with F(e.g., $CH_2F$, $CHF_2$, or $CF_3$), OR' or NRR';
$R^3$ is R' or halogen;
each of $R^4$ and $R^{4'}$, when L is $NR^{4'}$, is selected from hydrogen and $C_1$-$C_{16}$ (e.g., Ci-G, $C_7$-$C_{16}$) aliphatic groups optionally comprising one or more heteroatoms selected from N, O, S and P, and $R^4$ and $R^{4'}$ together may form a 3- to 7-membered ring, having 0 to 3 heteroatoms selected from O, N and S, and wherein each of $R^4$ and $R^{4'}$ is optionally substituted with CN, $CF_3$ or OR'; provided that if one of $R^4$ and $R^{4'}$ is hydrogen, the other is not hydrogen; and
each R and R' is independently hydrogen or a $C_1$-$C_{12}$ unsubstituted or substituted alkyl group,
or a pharmaceutically acceptable form or an isotope derivative thereof, effective to treat, prevent, or reduce one or more of inflammatory diseases, immune-mediated diseases, cancer, or a related disease or disorder thereof, in a mammal, including a human, and a pharmaceutically acceptable excipient, carrier, or diluent.

In certain embodiments of the method, L is O, X is $CR^X$, Y is CH, Zi is CH and $Z_2$ is N, and the compound has the structural formula (II):

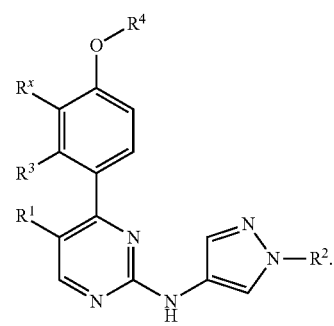

(II)

In certain embodiments of the method, L is $NR^{4'}$, X is $CR^X$, Y is CH, Zi is CH and $Z_2$ is N, and the compound has the structural formula (III):

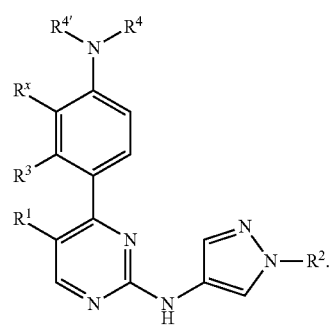

(III)

In certain embodiments of the method, $R^4$ comprises a linear, branched or cyclic Ci-$C_{12}$ (e.g., Ci-Ce, $C_7$-$C_{12}$) unsubstituted or substituted alkyl group.

In certain embodiments of the method, $R^4$ comprises a 3- to 7-membered (e.g., 3-, 4- or 5-membered) ring having 0 to 3 (e.g., 0, 1, 2, 3) heteroatoms selected from O, N and S. In certain embodiments of the pharmaceutical compositions, $R^4$ comprises a 3- to 7-membered (e.g., 3-, 4- or 5-membered) ring having 0 heteroatoms.

In yet another aspect, the invention generally relates to a method for treating or reducing a disease or disorder. The method includes administering to a subject in need thereof a pharmaceutical composition comprising a compound disclosed herein, wherein the disease or disorder is one or more of inflammatory diseases, immune-mediated diseases and cancer, or a related disease or disorder.

In certain embodiments of the method, the disease or disorder is an inflammatory disease.

In certain embodiments of the method, the disease or disorder is an immune-mediated disease.

In certain embodiments of the method, the disease or disorder is cancer.

In certain embodiments of the method, the disease or disorder is selected from: inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

In certain embodiments of the method, the administration is via oral administration.

In certain embodiments of the method, the administration is via topical administration.

In certain embodiments of the method, the administration is via G1-restricted administration.

In yet another aspect, the invention generally relates to use of a compound disclosed herein, and a pharmaceutically acceptable excipient, carrier, or diluent, in preparation of a medicament for treating a disease or disorder.

In certain embodiments of the use, the disease or disorder is one or more of inflammatory diseases, immune-mediated diseases and cancer.

In certain embodiments of the use, the disease or disorder is an autoimmune disease.

In certain embodiments of the use, the disease or disorder is an immune-mediated disease.

In certain embodiments of the use, the disease or disorder is cancer.

In certain embodiments of the use, the medicament is for oral administration.

In certain embodiments of the use, the medicament is for topical administration.

In certain embodiments of the use, the medicament is for GI restriction administration.

The term "inflammatory disease" refers to a disease or condition characterized by aberrant inflammation, e.g. an increased level of inflammation compared to a control such as a healthy person not suffering from a disease. Examples of inflammatory diseases that may be treated with a compound, pharmaceutical composition, or method described herein include autoimmune diseases, traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders, which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound of the present disclosure may be particularly efficacious (due to, for example, limitations of current therapies) are described in more detail hereafter.

The term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include acne vulgaris, acute disseminated encephalomyelitis, acute necrotizing hemorrhagic leukoencephalitis, Addison's disease, agammaglobulinemia, Aicardi-Goutieres syndrome (AGS), alopecia areata, alopecia totalis, amyloidosis, ankylosing spondylitis, anti-GBM/anti-TBM nephritis, antiphospholipid syndrome, autoimmune angioedema, autoimmune aplastic anemia, autoimmune dysautonomia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal or neuronal neuropathies, balo disease, Behcet's disease, bullous pemphigoid, cardiomyopathy, Castleman disease, celiac disease, Chagas disease, chronic atypical neutrophilic dermatosis with lipodystrophy and elevated temperature (CANDLE), chronic active hepatitis, chronic fatigue syndrome, chronic inflammatory demyelinating polyneuropathy, chronic recurrent multifocal ostomyelitis, Churg-Strauss syndrome, cicatricial pemphigoid/benign mucosal pemphigoid, Crohn's disease, Cogans syndrome, cold agglutinin disease, congenital heart block, coxsackie myocarditis, CREST disease, Cushing's disease, demyelinating neuropathies, depression, dermatitis herpetiformis, dermatomyositis, Devic's disease (neuromyelitis optica), discoid lupus, Dressler's syndrome, dry eye syndrome DES (keratoconjunctivitis sicca), endometriosis, eosinophilic esophagitis, eosinophilic fasciitis, erythema nodosum, essential mixed cryoglobulinemia, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, graft-versus-host disease (GVDH), Graves' disease, Guillain-Barre syndrome, Hashimoto's encephalitis, Hashimoto's thyroiditis, hemolytic anemia, Henoch-Schonlein purpura, herpes gestationis, hidradenitis suppurativa, hypogammaglobulinemia, idiopathic thrombocytopenic purpura, IgA nephropathy, IgG4-related sclerosing disease, inflammatory bowel disease (IBD), immunoregulatory lipoproteins, inclusion body myositis, interstitial cystitis, juvenile arthritis, juvenile diabetes (Type 1 diabetes), juvenile dermatomyositis (JDM), juvenile myositis, Kawasaki syndrome, Lambert-Eaton syndrome, leukocytoclastic vasculitis, lichen planus, lichen sclerosus, ligneous conjunctivitis, linear IgA disease, lupus, lyme disease, chronic, Meniere's disease, microscopic polyangiitis, mixed connective tissue disease, Mooren's ulcer, Mucha-Habermann disease, multiple sclerosis (MS), myasthenia gravis, myositis, narcolepsy, neuromyelitis optica, neutropenia, ocular cicatricial pemphigoid, optic neuritis, palindromic rheumatism, pediatric autoimmune neuropsychiatric disorders associated with *streptococcus*, paraneoplastic cerebellar degeneration, paroxysmal nocturnal hemoglobinuria p, Parry Romberg syndrome, Parsonnage-Turner syndrome, Pars planitis (peripheral uveitis), pemphigus, peripheral neuropathy, perivenous encephalomyelitis, pernicious anemia, POEMS syndrome, polyarteritis nodosa, polycystic ovary syndrome (PCOS), Type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, plaque psoriasis, idiopathic pulmonary fibrosis, pyoderma gangrenosum, pure red cell aplasia, Raynauds phenomenon, reactive Arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, stimulator of interferon genes (STING)-associated vasculopathy with onset during infancy (SAVI), subacute bacterial endocarditis, Susac's syndrome, sympathetic ophthalmia, systemic lupus erythematosus (SLE), Takayasu's arteritis, temporal arteritis/Giant cell arteritis, thrombocytopenic purpura, Tolosa-Hunt syndrome, transplant rejection (allograft transplant rejection), transverse myelitis, Type 1 diabetes, ulcerative colitis, undifferentiated connective tissue disease, uveitis, vasculitis, vesiculobullous dermatosis, vitiligo, or Wegener's granulomatosis.

The term "immune-mediated disease" refers to chronic inflammatory diseases perpetuated by antibodies and cellular immunity. Immune-mediated diseases include, for example, but not limited to, asthma, allergies, arthritis (e.g., rheumatoid arthritis, psoriatic arthritis, and ankylosing spondylitis), juvenile arthritis, inflammatory bowel diseases (e.g., ulcerative colitis and Crohn's disease), endocrinopathies (e.g., type 1 diabetes and Graves' disease), neurodegenerative diseases (e.g., multiple sclerosis (MS)), autistic spectrum disorder, depression, Alzheimer's disease, Guillain-Barre syndrome, obsessive-compulsive disorder, optic neuritis, retinal degeneration, dry eye syndrome DES, Sjogren's syndrome, amyotrophic lateral sclerosis (ALS), Parkinson's disease, Huntington's Disease, Guillain-Barre syndrome, myasthenia gravis, and chronic idiopathic demyelinating (CID)), vascular diseases (e.g., autoimmune hearing loss, systemic vasculitis, and atherosclerosis), and skin diseases (e.g., acne vulgaris dermatomyositis, pemphigus, systemic lupus erythematosus (SLE), discoid lupus erthematosus, scleroderma, psoriasis, plaque psoriasis, vasculitics, vitiligo and alopecias). Hashimoto's thyroiditis, pernicious anemia, Cushing's disease, Addison's disease, chronic active hepatitis, polycystic ovary syndrome (PCOS), celiac disease, pemphigus, transplant rejection (allograft transplant rejection), graft-versus-host disease (GVDH).

The term "cancer" as used herein refers to all types of cancer, neoplasm or malignant tumors found in mammals, e.g., humans, including hematological cancers leukemia, and lymphomas, T-ALL, large B-cell lymphoma, solid cancers such as carcinomas and sarcomas. Exemplary cancers include blood cancer, brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers include cancer of the thyroid, endocrine system, brain, breast, cervix, colon, head & neck, liver, kidney, lung, non-small cell lung, melanoma, mesothelioma, ovary, sarcoma, stomach, uterus, medulloblastoma, colorectal cancer, pancreatic cancer. Additional examples include penile, skin—non-melanoma, anal, hepatobiliary, esophagogastric, uterine sarcoma, gastrointestinal stromal tumor, salivary gland, peripheral nervous system, soft tissue sarcoma, bone, renal, myeloproliferative neoplasms, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, metastatic leiomyosarcoma, synovial sarcoma, undifferentiated pleomorphic sarcoma, round cell liposarcoma or prostate cancer.

In certain embodiments of the use, the disease or disorder is selected from: inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer and ovarian cancer.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^{1}H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. (See, WO 2007/005643, WO 2007/005644, WO 2007/016361, and WO 2007/016431.)

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure. Solvates and polymorphs of the compounds of the invention are also contemplated herein. Solvates of the compounds of the present invention include, for example, hydrates.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and ^-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

EXAMPLES

A series of analogues were designed, synthesized and tested. Examples of such compounds are provided below.

Abbreviations

Certain abbreviations are listed below.
Methanol: MeOH
Dichloromethane: DCM

Petroleum ether: PE
Ethyl acetate: EtOAc
Triethylamine: TEA
Sodium hydroxide: NaOH
Nitrogen: $N_2$
Thin-Layer Chromatography: TLC
High Performance Liquid Chromatography: HPLC
N,N-Diisopropylethylamine: DIPEA
N,N-Dimethylformamide: DMF
4-Methylmorpholine: NMM
Room temperature: RT
Hours: hrs
X-Phos: 2-Dicyclohexylphosphino-2',4',6'-triisopropylbiphenyl
Xant-phos: 4,5-Bis(diphenylphosphino)-9,9-dimethylxanthene Representative Methods of Prep-HPLC: (Flow Rate and Gradient May Change)

Exemplary methods for prep-HPLC are provided below.

Method A: NH4HCO3:

(Column: XBrige Prep C18 5 pm OBD 19*150 mm, PN 186002979; mobile phase: CH3CN in water (0.1% NH4HCO3) from 20% to 60%, flow rate: 15 mL/min).

Method B:TFA:

(Column: XBridge Prep C18 5 pm OBD 19*150 mm, PN 186002979; mobile phase: CH3CN in water (0.1% formic acid) from 15% to 40%, flow rate: 15 mL/min)

Representative Methods of Analytical-HPLC

Method 1: Analysis was performed on an Agilent 1260 series HPLC-6120MS. UHPLC Long Gradient Equivalent 5% to 95% acetonitrile (containing 0.02% NH4OAc) in water run time of 6.5 minutes with a flow rate of 1.5 mL/min. A XBridge C18 column (5 pm, 4.6*50 mm; PN 1860031 13) was used at a temperature of 40° C.

Method 2: Analysis was performed on an Agilent 1200 series HPLC-6120MS. UHPLC Long Gradient Equivalent 5% to 95% acetonitrile (containing 0.1% trifluoroacetic acid) in water run time of 6.5 minutes with a flow rate of 1.5 mL/min. A XBridge C18 column (5 pm, 4.6*50 mm; PN 1860031 13) was used at a temperature of 40° C.

Method 3: Analysis was performed on an Agilent 1260 series HPLC-6120MS. UHPLC Long Gradient Equivalent 5% to 95% acetonitrile (containing 0.02% NH4OAc) in water run time of 6.5 minutes with a flow rate of 2 mL/min. A Diamonsil Plus C18 column (5 pm, 4.6*30 mm Cat #99436) was used at a temperature of 40° C.

Example 1

Step 1. 4-(2-Chloro-5-methylpyrimidin-4-yl)phenol (1b)

A mixture of compound 1a (3.0 g, 18.40 mmol), (4-hydroxyphenyl)boronic acid (4.46 g, 20.24 mmol), Na2CO3 (3.90 g, 36.8 mmol) and Pd(dppf)Cb (942 mg, 1.288 mmol) in 1,4-dioxane/tbO (24 mL/6 mL) was stirred at 60° C. under N2 overnight. The mixture was cooled down to RT and concentrated. The residue was purified by column chromatography on silica gel (eluent: PE: EtOAc=2:1) to give the product (2.22 g, 55% yield) as a white solid. LC-MS (Method 2): $t_R$=1.34 mm, m/z (M+H)$^+$=221.1.

Step 2. 4-(2-((1-Cyclopropyl-1//-pyrazol-4-yl)amino)-5-methylpyrimidin-4-yl)phenol (1c)

A mixture of compound 1 b (500 mg, 2.27 mmol), 1-cyclopropyl-lif-pyrazol-4-amine (418 mg, 3.40 mmol), Pd2(dba)3 (145 mg, 0.1589 mmol), X-Phos (151 mg, 0.32 mmol) and Cs$_2$CO$_3$ (1.11 g, 3.40 mmol) in 1,4-dioxane (10 mL) was stirred at 100° C. under N2for 3 hrs. The mixture was cooled down to RT and concentrated. The residue was purified by column chromatography on silica gel (eluent: DCM: MeOH=30:1) to give the product (366 mg, 53% yield) as an off-white solid. LC-MS (Method 1): $t_R$=2.89 min, m/z (M+H)$^+$=308.0.

Step 3. 3-Hydroxy-2,2-dimethylpropanenitrile (1e)

To a solution of compound Id (2.0 g, 15.7 mmol) in MeOH (30 mL) was added NaBH$_4$ (898 mg, 23.6 mmol) in portions. The mixture was stirred at 0° C.—RT for 2 hrs. The mixture was quenched with acetone (2 mL) and concentrated under reduced pressure. The residue was diluted with DCM (10 mL) and filtered. The filtrate was concentrated to give the crude product (1.23 g, 79% yield) as colorless oil. $^3$M NMR (400 MHz, DMSO-d$_6$) δ 5.45 (t, J=5.6 Hz, 1H), 3.36 (d, J=6.0 Hz, 2H), 1.22 (s, 6H).

Step 4. 2-Cyano-2-methylpropyl methanesulfonate (1f)

To a solution of compound 1e (300 mg, 3.03 mmol) and TEA (2.17 g, 21.4 mmol) in DCM (4 mL) was dropwise added MsCl (1.47 g, 12.84 mmol) at 0° C. The mixture was stirred at 0° C.—RT under N2 for 1 hour. The mixture was added water (20 mL volume) and extracted with DCM (30 mL*2). The combined organic layers were washed with brine, dried over Na$_2$SC>$_4$, filtered and concentrated to give the crude product (600 mg, 100% yield) as yellow oil. $^1$H NMR (400 MHz, CDCh) δ 4.12 (s, 2H), 3.12 (s, 3H), 1.45 (s, 6H).

Step 5. 3-(4-(2-((1-Cyclopropyl-Lif-pyrazol-4-yl)amino)-5-methylpyrimidin-4-yl)phenoxy)-2,2-dimethylpropanenitrile (1)

A mixture of compound 1c (80 mg, 0.261 mmol), compound If (139 mg, 0.783 mmol) and CS2CO3 (170 mg, 0.522 mmol) in DMF (1.5 mL) was stirred at 100° C. overnight. The mixture was cooled down to RT and filtered. The filtrate was concentrated and purified by prep-HPLC (Method A) to give the product (51.9 mg, 51% yield) as a light yellow solid. LC-MS (Method 1): $t_R$=3.51 mm, m/z (M+H)$^+$=389.2. ¾ NMR (400 MHz, DMSO-d$_6$) δ 9.28 (s, 1H), 8.30 (s, 1H), 7.90 (s, 1H), 7.69 (d, J=8.4 Hz, 2H), 7.47 (s, 1H), 7.13 (d, J=8.8 Hz, 2H), 4.10 (s, 2H), 3.67-3.62 (m, 1H), 2.21 (s, 3H), 1.44 (s, 6H), 0.98-0.91 (m, 4H).

Example 2

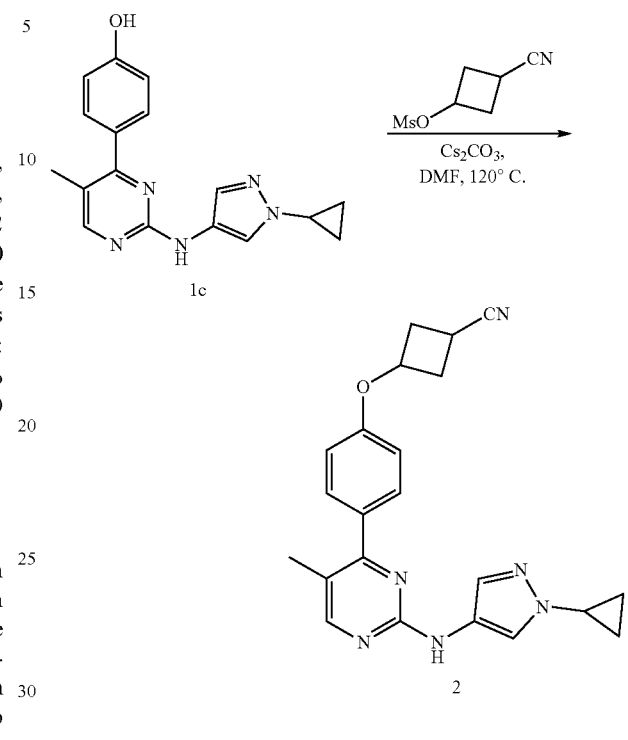

3-(4-(2-((1-Cyclopropyl-1fT-pyrazol-4-yl)amino)-5-methylpyrimidin-4-yl)phenoxy)cyclobutanecarbonitrile (2)

Compound 2 (12.1 mg) was synthesized in 15% yield by utilizing a similar preparative procedure to the final step of Example 1 with compound 1c (65 mg, 0.211 mmol) and 3-cyanocyclobutyl methanesulfonate (129 mg, 0.741 mmol) as starting materials. LC-MS (Method 1): $t_R$=3.75 mm, m/z (M+H)$^+$=387.2. ¾ NMR (400 MHz, DMSO-d$_6$) δ 9.28 (s, 1H), 8.30 (s, 1H), 7.89 (s, 1H), 7.66 (d, J=8.0 Hz, 2H), 7.48 (s, 1H), 6.99 (d, J=8.8 Hz, 2H), 5.09-5.03 (m, 0.8H), 4.80-4.77 (m, 0.2H), 3.67-3.62 (m, 1H), 3.49-3.43 (m, 2H), 3.15-3.10 (m, 0.2H), 2.99-2.92 (m, 0.4H), 2.88-2.82 (m, 1.4H), 2.43-2.35 (m, 1H), 2.20 (s, 3H), 0.99-0.89 (m, 4H).

Example 3

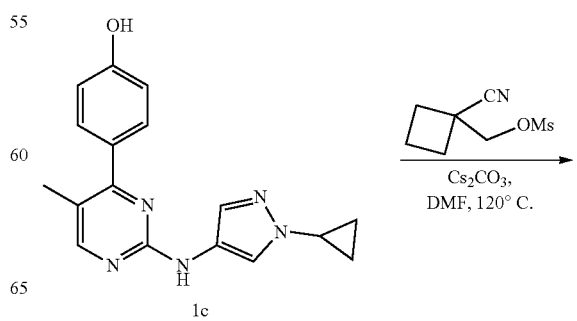

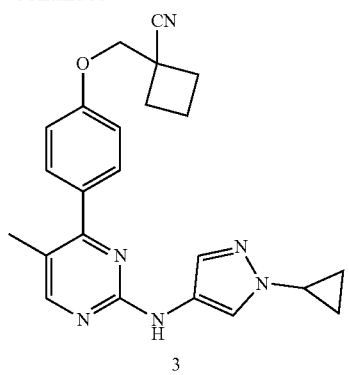

1-((4-(2-((1-Cyclopropyl-1*H*-pyrazol-4-yl)amino)-5-methylpyrimidin-4-yl)phenoxy)methyl)cyclobutanecarbonitrile (3)

Compound 3 (27.8 mg) was synthesized in 39% yield by utilizing a similar preparative procedure to the final step of Example 1 with compound 1c (55 mg, 0.179 mmol) and (1-cyanocyclobutyl)methyl methanesulfonate (140 mg, 0.719 mmol) as starting materials. LC-MS (Method 1): $t_R$=3.47 mm, m/z (M+H)$^+$=401.2. ¾ NMR (400 MHz, DMSO-d$_6$) δ 9.29 (s, 1H), 8.30 (s, 1H), 7.90 (s, 1H), 7.69 (d, J=8.4 Hz, 2H), 7.47 (s, 1H), 7.13 (d, J=8.8 Hz, 2H), 4.34 (s, 2H), 3.67-3.62 (m, 1H), 2.54-2.53 (m, 2H), 2.32-2.25 (m, 2H), 2.21 (s, 3H), 2.14-2.11 (m, 2H), 0.97-0.91 (m, 4H).

Example 4

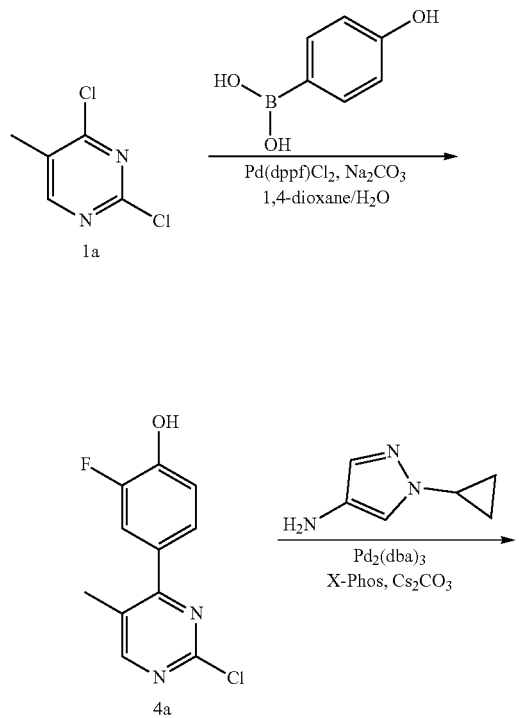

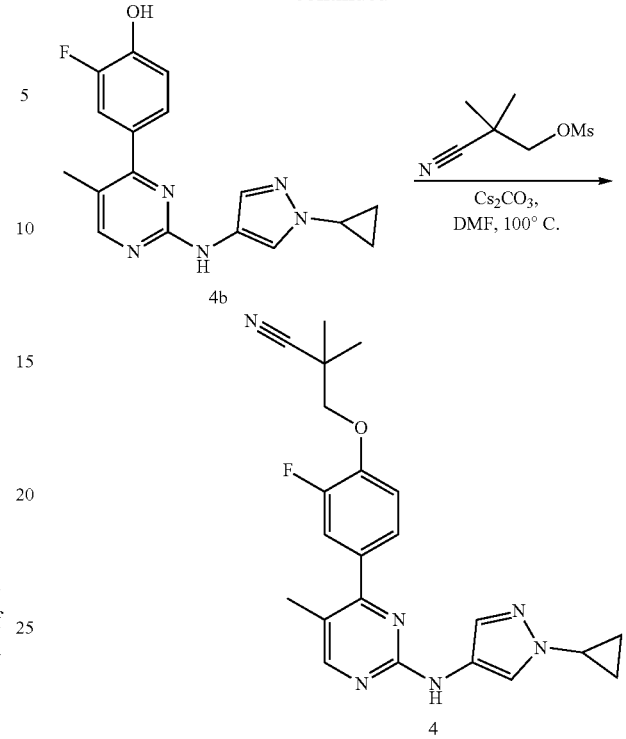

Step 1. 4-(2-Chloro-5-methylpyrimidin-4-yl)-2-fluorophenol (4a)

Compound 4a (375 mg) was synthesized in 49% yield by utilizing a similar preparative procedure to the first step of Example 1 with compound 1a (523 mg, 3.21 mmol) and (3-fluoro-4-hydroxyphenyl)boronic acid (500 mg, 3.21 mmol) as starting materials. LC-MS (Method 2): $t_R$-1.42 min, m/z (M+H)$^+$=239.0.

Step 2. 4-(2-((1-Cyclopropyl-1*H*-pyrazol-4-yl)amino)-5-methylpyrimidin-4-yl)-2-fluorophenol (4b)

Compound 4b (190 mg) was synthesized in 37% yield by utilizing a similar preparative procedure to the second step of Example 1 with compound 4a (375 mg, 1.576 mmol) and 1-cyclopropyl-1*H*-pyrazol-4-amine (233 mg, 1.891 mmol) as starting materials. LC-MS (Method 1): $t_R$=1.45 min, m/z (M+H)$^+$=326.1.

Step 3. 3-(4-(2-((1-Cyclopropyl-Li7-pyrazol-4-yl)amino)-5-methylpyrimidin-4-yl)-2-fluorophenoxy)-2,2-dimethylpropanenitrile (4)

Compound 4 (27.2 mg) was synthesized in 22% yield by utilizing a similar preparative procedure to the final step of Example 1 with compound 4b (95 mg, 0.292 mmol) and 2-cyano-2-methylpropyl methanesulfonate (155 mg, 0.877 mmol) as starting materials. LC-MS (Method 1): $t_R$=4.07 min, m/z (M+H)$^+$=407.2. ¾ NMR (400 MHz, DMSO-d$_6$) δ 9.33 (s, 1H), 8.33 (s, 1H), 7.90 (s, 1H), 7.62 (dd, J=1.6, 14.0 Hz, 1H), 7.52 (d, J=8.0 Hz, 1H), 7.47 (s, 1H), 7.34 (t, J=8.8 Hz, 1H), 4.19 (s, 2H), 3.67-3.63 (m, 1H), 2.22 (s, 3H), 1.45 (s, 6H), 1.00-0.91 (m, 4H).

Example 5

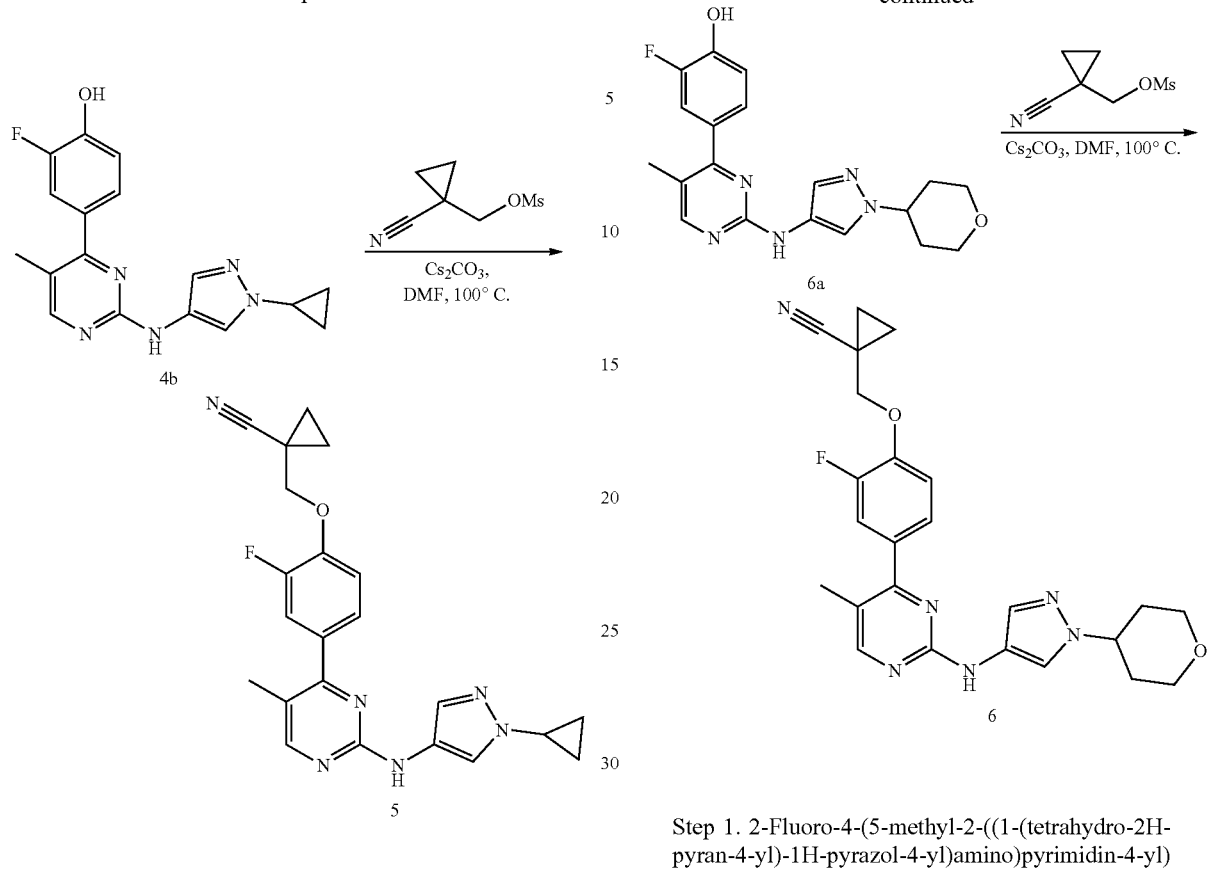

1-((4-(2-((1-Cyclopropyl-1H-pyrazol-4-yl)amino)-5-methylpyrimidin-4-yl)-2-fluorophenoxy)methyl) cyclopropanecarbonitrile (5)

Compound 5 (34.5 mg) was synthesized in 28% yield by utilizing a similar preparative procedure to the final step of Example 1 with compound 4b (100 mg, 0.307 mmol) and (1-cyanocyclopropyl)methyl methanesulfonate (162 mg, 0.922 mmol) as starting materials. LC-MS (Method 1): $t_R$=3.60 mm, m/z (M+H)$^+$=405.1. ¾ NMR (400 MHz, DMSO-d$_6$) δ 9.33 (s, 1H), 8.33 (s, 1H), 7.89 (s, 1H), 7.61 (d, J=12.4 Hz, 1H), 7.51 (d, J=8.8 Hz, 1H), 7.47 (s, 1H), 7.26 (t, J=8.4 Hz, 1H), 4.20 (s, 2H), 3.66-3.63 (m, 1H), 2.22 (s, 3H), 1.453-1.40 (m, 2H), 1.22-1.19 (m, 2H), 1.00-0.89 (m, 4H). $^{19}$F NMR (376 MHz, DMSO-d$_6$) δ-134.28.

Example 6

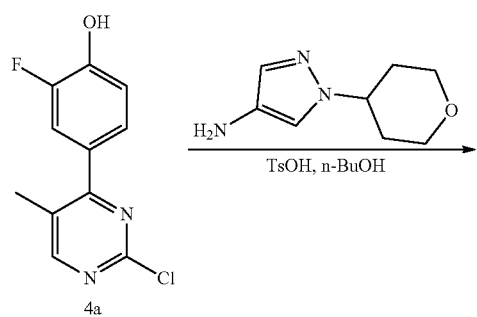

Step 1. 2-Fluoro-4-(5-methyl-2-((1-(tetrahydro-2H-pyran-4-yl)-1H-pyrazol-4-yl)amino)pyrimidin-4-yl) phenol (6a)

A mixture of compound 4a (300 mg, 1.26 mmol), 1-(tetrahydro-2H-pyran-4-yl)-1H-pyrazol-4-amine (318 mg, 1.89 mmol) and TsOH (105 mg, 0.63 mmol) in n-BuOH (2 mL) was stirred at 120° C. for 6 hrs. The mixture was cooled to RT, diluted with DCM (30 mL) and concentrated to give a residue. The residue was diluted with DCM (10 mL) and TLO (10 mL), and extracted with DCM (10 mL*3). The combined organic layers were dried over Na$_2$SC>$_4$, filtered and concentrated to give a crude product (224 mg, 48% yield) as a green solid. LC-MS (Method 2): $t_R$=1.41 mm, m/z (M+H)$^+$=370.1.

Step 2. 1-((2-Fluoro-4-(5-methyl-2-((1-(tetrahydro-2//-pyran-4-yl)-1//-pyrazol-4-yl)amino)pyrimidin-4-yl)phenoxy)methyl)cyclopropanecarbonitrile (6)

Compound 6 (43.7 mg) was synthesized in 45% yield by utilizing a similar preparative procedure to the final step of Example 1 with compound 6a (80 mg, 0.217 mmol) and (1-cyanocyclopropyl)methyl methanesulfonate (114 mg, 0.650 mmol) as starting materials. LC-MS (Method 1): $t_R$=3.16 mm, m/z (M+H)$^+$=449.2. $^1$H NMR (400 MHz, DMSO-d$_6$) δ 9.32 (s, 1H), 8.32 (s, 1H), 7.91 (s, 1H), 7.62 (d, J=12.4 Hz, 1H), 7.52 (t, J=6.0 Hz, 2H), 7.26 (t, J=8.8 Hz, 1H), 4.35-4.30 (m, 1H), 4.20 (s, 2H), 3.96-3.93 (m, 2H), 3.48-3.42 (m, 2H), 2.22 (s, 3H), 1.96-1.85 (m, 4H), 1.43-1.40 (m, 2H), 1.22-1.19 (m, 2H). $^{19}$F NMR (376 MHz, DMSO-d$_6$) δ-134.29.

Example 7

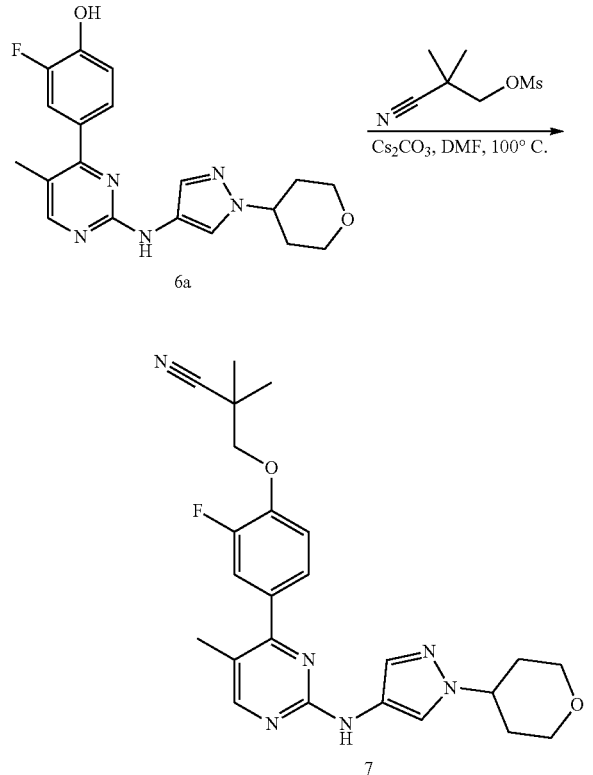

3-(2-Fluoro-4-(5-methyl-2-((1-(tetrahydro-2H-pyran-4-yl)-1H-pyrazol-4-yl)amino)pyrimidin-4-yl)phenoxy)-2,2-dimethylpropanenitrile (7)

Compound 7 (36.8 mg) was synthesized in 60% yield by utilizing a similar preparative procedure to the final step of Example 1 with compound 6a (50 mg, 0.14 mmol) and 2-cyano-2-methylpropyl methanesulfonate (72 mg, 0.41 mmol) as starting materials. LC-MS (Method 1): $t_R$=3.531 min, m/z (M+H)$^+$=451.2. ¾ NMR (400 MHz, DMSO-$d_6$) δ 9.32 (s, 1H), 8.32 (s, 1H), 7.91 (s, 1H), 7.62 (d, J=12.4 Hz, 1H), 7.53 (t, J=10.4 Hz, 2H), 7.33 (t, J=8.4 Hz, 1H), 4.37-4.29 (m, 1H), 4.19 (s, 2H), 3.94 (d, J=11.2 Hz, 2H), 3.48-3.42 (m, 2H), 2.22 (s, 3H), 1.96-1.87 (m, 4H), 1.45 (s, 6H). $^{19}$F NMR (376 MHz, DMSO-$d_6$) δ -134.83.

Example 8

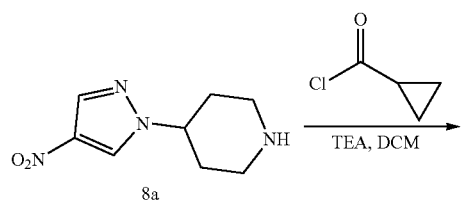

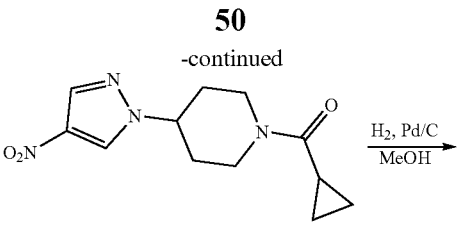

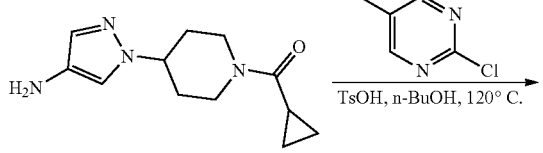

Step 1. Cyclopropyl(4-(4-nitro-1H-pyrazol-1-yl)piperidin-1-yl)methanone (8b)

To a solution of compound 8a (1.0 g, 5.096 mmol) and TEA (1.55 g, 15.288 mmol) in DCM (10 mL) was added cyclopropanecarbonyl chloride (692 mg, 6.625 mmol) dropwise at 0° C. The mixture was stirred at RT for 1 hr. The mixture was diluted with DCM (100 mL) and washed with water (30 mL). The separated organic layers were washed with brine, dried over $Na_2SO_4$ and filtered. The filtrate was concentrated and purified by LCC (eluent: DCM:MeOH=50:1) to give the product (1.08 g, 80% yield) as a white solid. LC-MS (Method 2): $t_R$=1.25 min, m/z (M+H)$^+$=265.1.

Step 2. (4-(4-Amino-1/T-pyrazol-1-yl)piperidin-1-yl)(cyclopropyl)methanone (8c)

To a solution of compound 8b (500 mg, 1.89 mmol) in MeOH (6 mL) was added Pd/C (100 mg, 10% Pd/C wetted with ca. 55% water). The mixture was stirred at RT under ¾ (1 atm) overnight. The mixture was filtered. The filtrate was concentrated to give the crude product (472 mg, 100% yield) as brown oil. LC-MS (Method 2): $t_R$=0.76 min, m/z $(M+H)^+$=235.1.

Step 3. Cyclopropyl(4-(4-((4-(3-fluoro-4-hydroxyphenyl)-5-methylpyrimidin-2-yl)amino)-1//-pyrazol-1-yl)piperidin-1-yl)methanone (8d)

Compound 8d (479 mg) was synthesized in 87% yield by utilizing a similar preparative procedure to the first step of Example 6 with compound 4a (300 mg, 1.26 mmol) and compound 8c (442 mg, 1.89 mmol) as starting materials. LC-MS (Method 2): $t_R$=1.38 min, m/z $(M+H)^+$=437.2.

Step 4. 1-((4-(2-((1-(1-(Cyclopropanecarbonyl)piperidin-4-yl)-1/T-pyrazol-4-yl)amino)-5-methylpyrimidin-4-yl)-2-fluorophenoxy)methyl)cyclopropanecarbonitrile (8)

Compound 8 (30.3 mg) was synthesized in 32% yield by utilizing a similar preparative procedure to the final step of Example 1 with compound 8d (80 mg, 0.183 mmol) and (1-cyanocyclopropyl)methyl methanesulfonate (96 mg, 0.549 mmol) as starting materials. LC-MS (Method 1): $t_R$=3.73 mm, m/z $(M+H)^+$=516.3. ¾ NMR (400 MHz, DMSO-$d_6$) δ 9.33 (s, 1H), 8.32 (s, 1H), 7.91 (s, 1H), 7.62 (d, J=12.4 Hz, 1H), 7.52 (t, J=6.8 Hz, 2H), 7.25 (t, J=8.8 Hz, 1H), 4.45-4.32 (m, 3H), 4.20 (s, 2H), 3.28-3.23 (m, 2H), 2.81-2.70 (m, 1H), 2.22 (s, 3H), 2.07-1.98 (m, 2H), 1.87-1.65 (m, 2H), 1.43-1.40 (m, 2H), 1.22-1.19 (m, 2H), 0.72-0.70 (m, 4H). $^{19}$F NMR (376 MHz, DMSO-$d_6$) δ-134.24.

Example 9

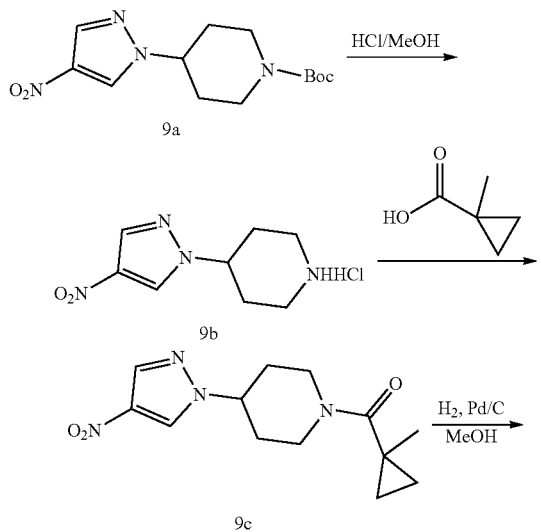

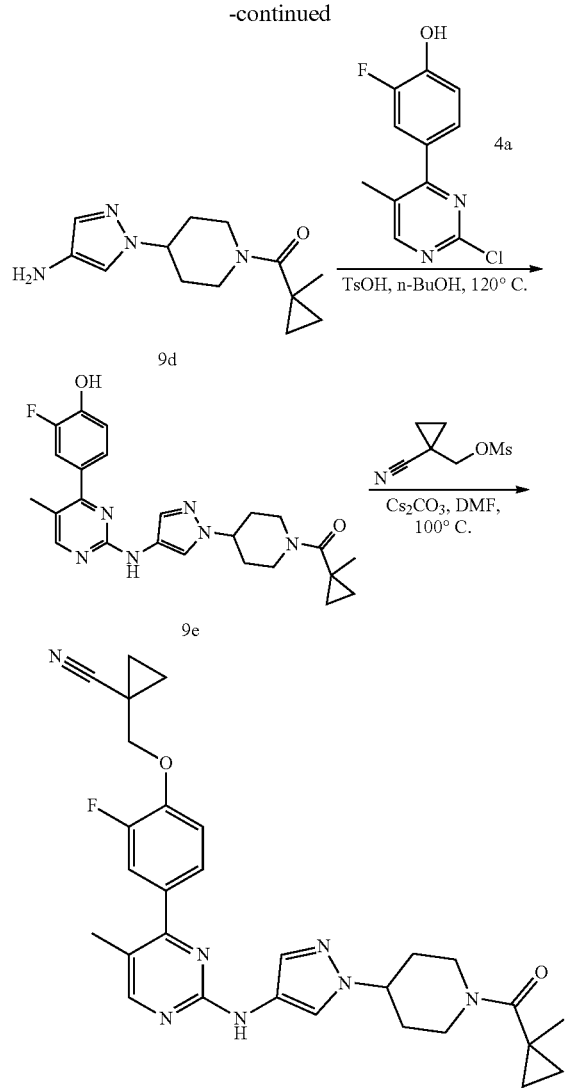

Step 1. 4-(4-Nitro-1//-pyrazol-1-yl)piperidine hydrochloride (9b)

A solution of compound 9a (1.91 g, 6.45 mmol) in a solution of HCl(g) in MeOH (2M, 20 mL) and DCM (5 mL) was stirred at RT for 2 hrs. The mixture was concentrated and purified by prep-HPhC to give the product (840 mg, 60% yield) as a white solid. LC-MS (Method 2): $t_R$=0.49 min, m/z $(M+H)^+$=197.3.

Step 2. (1-Methylcyclopropyl)(4-(4-nitro-L/T-pyrazol-1-yl)piperidin-1-yl)methanone (9c)

To a solution of 1-methylcyclopropanecarboxylic acid (500 mg, 5.0 mmol) in DCM (20 mL) was added oxalyl dichloride (760 mg, 6.0 mml) followed by 1 drop of DMF at 0° C. After stirring for 2 hrs at RT, the reaction mixture was concentrated to afford 1-methylcyclopropanecarbonyl chloride. To a solution of compound 9b (840 mg, 3.01 mmol) and TEA (1.09 g, 10.83 mmol) in THF (4 mL) was added 1-methylcyclopropanecarbonyl chloride (590 mg, 5.00 mmol). The mixture was stirred at RT for 1 hr. The mixture was diluted with 3/4 0 (20 mL) and extracted with DCM (30 mL*2). The combined organic layers were washed with brine, concentrated and purified by LCC (eluent: DCM:MeOH=50:1) to give the product (400 mg, 40% yield) as a yellow solid. LC-MS (Method 2): $t_R$=1.28 mi m/z (M+H)$^+$=279.4.

Step 3. (4-(4-Amino-1/T-pyrazol-1-yl)piperidin-1-yl)(1-methylcyclopropyl)methanone (9d)

To a solution of compound 9c (400 mg, 1.35 mmol) in MeOH (10 mL) was added Pd/C (100 mg, 10% Pd/C wetted with ca. 55% water). The mixture was stirred at 50° C. under 34 (50 psi) for 2 hrs. The mixture was filtered. The filtrate was concentrated to give the crude product (360 mg, 100% yield) as brown oil. LC-MS (Method 2): t=0.95 mi m/z (M+H)=249.1.

Step 4. (4-(4-((4-(3-Fluoro-4-hydroxyphenyl)-5-methylpyrimidin-2-yl)amino)-1/T-pyrazol-1-yl)piperidin-1-yl)(1-methylcyclopropyl)methanone (9e)

Compound 9e (321 mg) was synthesized in 69% yield by utilizing a similar preparative procedure to the first step of Example 6 with compound 4a (247 mg, 1.04 mmol) and compound 9d (442 mg, 1.89 mmol) as starting materials. LC-MS (Method 2): $t_R$=1.40 min, m/z (M+H)$^+$=451.2.

Step 5. 1-((2-Fluoro-4-(5-methyl-2-((1-(1-(1-methylcyclopropanecarbonyl)piperidin-4-yl)-1//-pyrazol-4-yl)amino)pyrimidin-4-yl)phenoxy)methyl)cyclopiOpanecarbonitrile (9)

Compound 9 (19.9 mg) was synthesized in 24% yield by utilizing a similar preparative procedure to the final step of Example 1 with compound 9e (72 mg, 0.16 mmol) and (1-cyanocyclopropyl)methyl methanesulfonate (84 mg, 0.48 mmol) as starting materials. LC-MS (Method 1): $t_R$=3.65 mm, m/z (M+H)$^+$=530.3. ¾ NMR (400 MHz, DMSO-$d_6$) δ 9.35 (s, 1H), 8.32 (s, 1H), 7.93 (s, 1H), 7.62 (d, J=12.0 Hz, 1H), 7.53-7.50 (m, 2H), 7.25 (t, J=8.4 Hz, 1H), 4.37-4.32 (m, 3H), 4.20 (s, 2H), 3.08-2.88 (m, 2H), 2.22 (s, 3H), 2.05-2.02 (m, 2H), 1.80-1.71 (m, 2H), 1.43-1.40 (m, 2H), 1.24 (s, 3H), 1.22-1.19 (m, 2H), 0.82-0.79 (m, 2H), 0.56-0.53 (m, 2H). $^{19}$F NMR (376 MHz, DMSO-$d_6$) δ-134.27.

Example 10

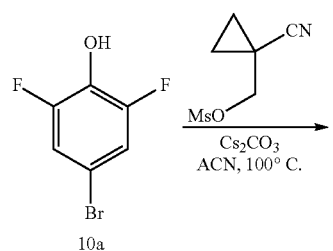

10a

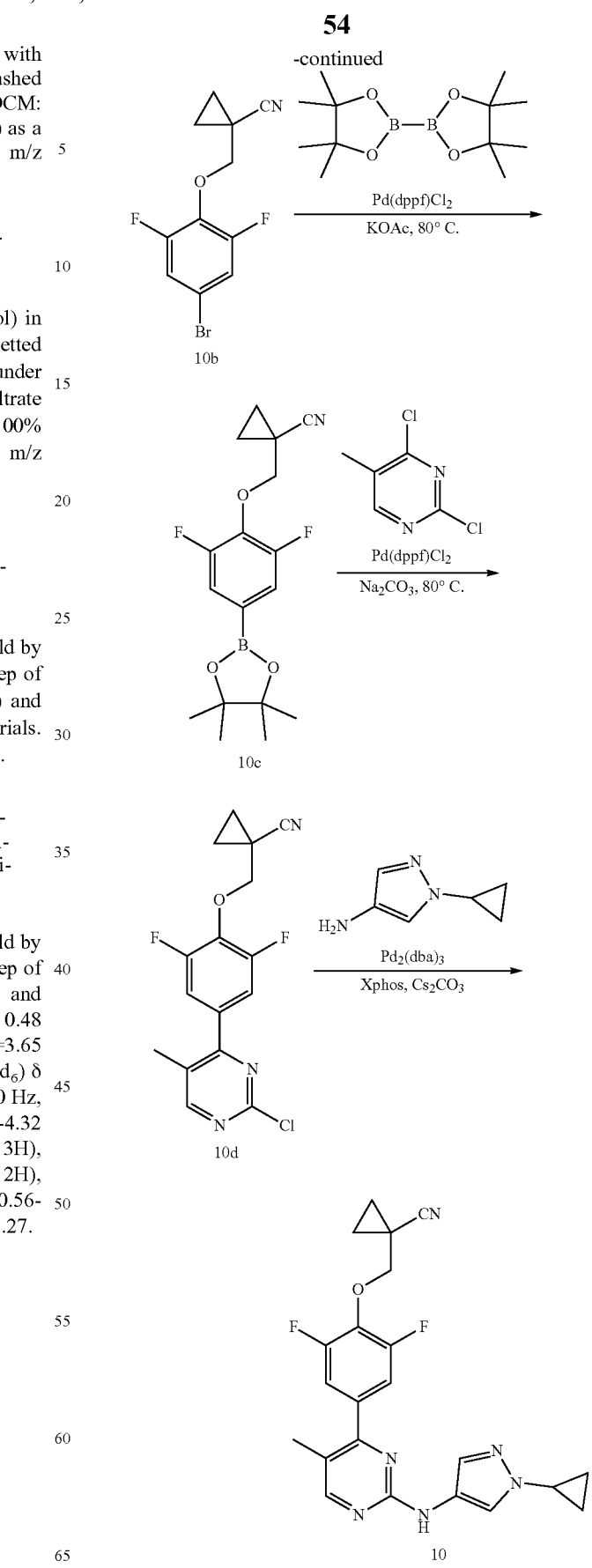

10

Step 1. 1-((4-Bromo-2,6-difluorophenoxy)methyl)cyclopropanecarbonitrile (10b)

A mixture of compound 10a (510 mg, 2.45 mmol), (1-cyanocyclopropyl)methyl methanesulfonate (472 mg, 2.70 mmol) and CS2CO3 (1.60 g, 4.93 mmol) in 16 mL of acetonitrile was stirred at 100° C. for 2 hrs. After cooling down to RT, the mixture was concentrated and the residue was purified by chromatography on silica gel (elute: PE:EtOAc from 20:1 to 10:1) to afford the title product as colorless oil (555 mg, 79% yield). ¾ NMR (400 MHz, DMSO-d$_6$) δ 7.58-7.51 (m, 2H), 4.13 (s, 2H), 1.36-1.32 (m, 2H), 1.11-1.08 (m, 2H).

Step 2. 1-((2,6-Difluoro-4-(4,4,5,5-tetramethyl-1,3,2-dioxaborolan-2-yl)phenoxy)methyl)cyclopropanecarbonitrile (10c)

A mixture of compound 10b (555 mg, 1.93 mmol), bis(pinacolato)diboron (637 mg, 2.51 mmol), Pd(dppf)Cl$_2$ (141 mg, 0.193 mmol) and KOAc (378 mg, 3.86 mmol) in 14 mL of 1,4-dixoane was stirred at 80° C. for 16 hrs under N2atmosphere. After cooling down to RT, the mixture was filtered and the filtrate was concentrated to afford the title product as a yellow solid (645 mg, crude, 100% yield). LC-MS (Method 1): t$_R$=1.88 min, m/z (M+18)$^+$=353.2.

Step 3. 1-((4-(2-Chloro-5-methylpyrimidin-4-yl)-2,6-difluorophenoxy)methyl)cyclopropanecarbonitrile (10d)

Compound 10d (490 mg) was synthesized in 76% yield by utilizing a similar preparative procedure to the first step of Example 1 with compound 10c (645 mg, 3.21 mmol) and 2,4-dichloro-5-methylpyrimidine (314 mg, 1.93 mmol) as starting materials. LC-MS (Method 2): t$_R$=1.63 min, m/z (M+H)$^+$=336.1.

Step 4. 1-((4-(2-((1-Cyclopropyl-1//-pyrazol-4-yl)amino)-5-methylpyrimidin-4-yl)-2,6-difluorophenoxy)methyl)cyclopropanecarbonitrile (10)

Compound 10 (54 mg) was synthesized in 21% yield by utilizing a similar preparative procedure to the second step of Example 1 with compound 10d (200 mg, 0.597 mmol) and 1-cyclopropyl-1//-pyrazol-4-amine (110 mg, 0.895 mmol) as starting materials. LC-MS (Method 1): t$_R$=2.33 min, m/z (M+H)$^+$=423.1. ¾ NMR (400 MHz, DMSO-d$_6$) δ 9.38 (s, 1H), 8.37 (s, 1H), 7.89 (s, 1H), 7.52-7.47 (m, 3H), 4.24 (s, 2H), 3.67-3.62 (m, 1H), 2.21 (s, 3H), 1.38-1.35 (m, 2H), 1.16-1.13 (m, 2H), 1.00-0.89 (m, 4H).

Example 11

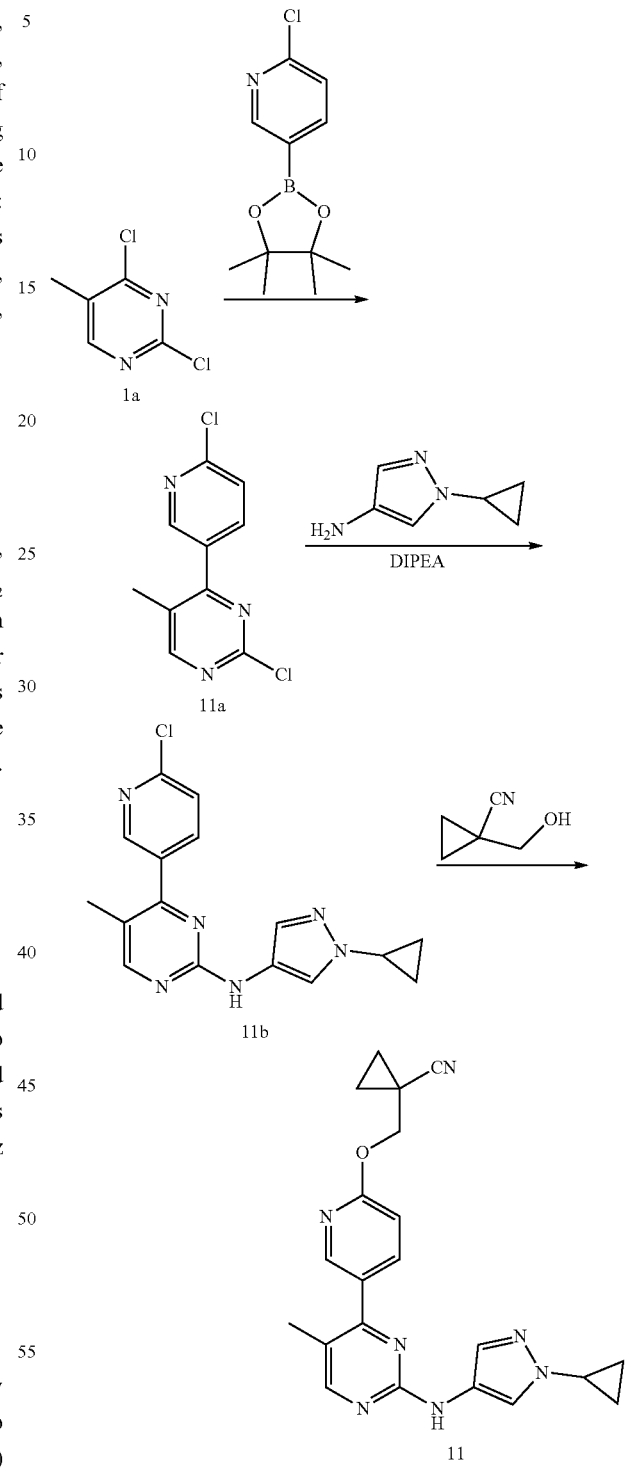

Step 1. 2-Chloro-4-(6-chloropyridin-3-yl)-5-methylpyrimidine (11a)

Compound 11a (1.0 g) was synthesized in 100% yield utilizing a similar preparative procedure to the first step of Example 1 with compound 1a (1.36 g, 8.36 mmol) and 2-chloro-5-(4,4,5,5-tetramethyl-1,3,2-dioxaborolan-2-yl)pyridine (1.0 g, 4.18 mmol) as starting materials. LC-MS (Method 2): $t_R$=1.42 min, m/z (M+H)$^+$=240.0.

Step 2. 4-(6-Chloropyridin-3-yl)-/V-(1-cyclopropyl-1//-pyrazol-4-yl)-5-methylpyrimidin-2-amine (lib)

A mixture of 11a (200 mg, 0.84 mmol), 1-cyclopropyl-liT-pyrazol-4-amine (204 mg, 1.66 mmol) and DIPEA (322 mg, 2.50 mmol) in NMP (0.5 mL) was stirred at 170° C. for 1 hour under microwave. The mixture was diluted with water (5 mL) and extracted with EtOAc (15 mL*3). The separated organic layer was washed with brine (20 mL) and concentrated. The residue was purified by FCC (PE: EtOAc=2:1) to afford the title compound (130 mg, 48% yield) as yellow solid. ¾ NMR (400 MHz, CDCh-d$_6$) δ 8.69 (s, 1H), 8.32 (s, 1H), 7.94 (dd, J=2.4, 8.4 Hz, 1H), 7.88 (s, 1H), 7.48 (s, 1H), 7.46 (d, J=8.4 Hz, 1H), 6.78 (s, 1H), 3.59-3.55 (m, 1H), 2.27 (s, 3H), 1.13-1.12 (m, 2H), 1.00-0.99 (m, 2H).

Step 3. 1-(((5-(2-((1-Cyclopropyl-1/T-pyrazol-4-yl)amino)-5-methylpyrimidin-4-yl)pyridin-2-yl)oxy)methyl)cyclopropanecarbonitrile (11)

To a solution of 1-(hydroxymethyl)cyclopropanecarbonitrile (35 mg, 0.36 mmol) in THF (1 mL) was added NaH (11 mg, 0.28 mmol, 60% in mineral oil) at 0° C. After stirring for 2 hrs at 0° C.—RT, compound lib (60 mg, 0.18 mmol) was added to the reaction mixture. Then the reaction was stirred for 8 hrs at 80° C. After cooling to RT, the mixture was diluted with water (10 mL) and extracted with EtOAc (20 mL*3). The separated organic layer was concentrated. The residue was purified by prep-HPLC to afford title compound (10 mg, 14% yield) as yellow solid. LC-MS (Method 1): $t_R$=3.60 min, m/z (M+H)$^+$=388.2; ¾ NMR (400 MHz, CDCh) δ 8.43 (s, 1H), 8.28 (s, 1H), 7.95 (dd, J=2.4, 8.8 Hz, 1H), 7.89 (s, 1H), 7.50 (s, 1H), 6.96 (d, J=8.4 Hz, 1H), 6.75 (s, 1H), 4.40 (s, 2H), 3.59-3.56 (m, 1H), 2.28 (s, 3H), 1.43-1.40 (m, 2H), 1.18-1.11 (m, 4H), 1.02-0.99 (m, 2H).

Example 12

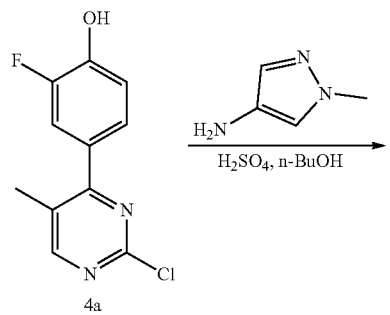

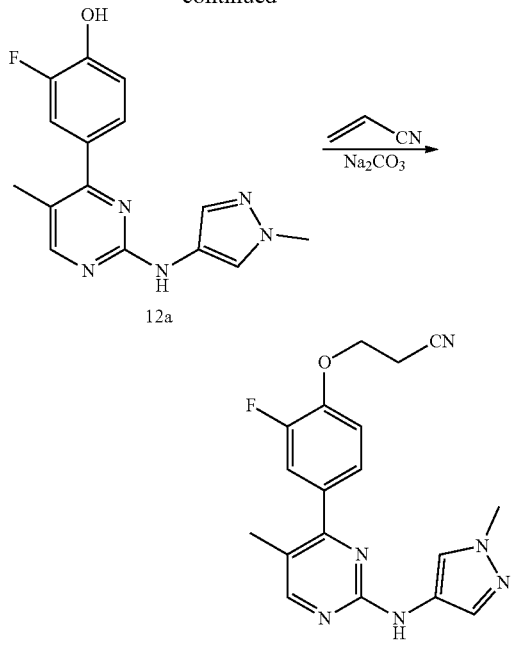

Step 1. 2-Fluoro-4-(5-methyl-2-((1-methyl-I//-pyrazol-4-yl)amino)pyrimidin-4-yl)phenol (12a)

A mixture of 4a (500 mg, 2.1 mmol), 1-methyl-1if-pyrazol-4-amine (295 mg, 3.0 mmol) and cone. H2SO4 (1 drop) in n-BuOH (3 mL) was stirred at 120° C. for 2 hours. The reaction mixture was concentrated and purified by silica gel column (DCM: MeOH=20:1) to give the product (357 mg, 57% yield) as a brown solid. LC-MS (Method 3): $t_R$=1.28 min, m/z (M+H)$^+$=300.1.

Step 2. 3-(2-Fluoro-4-(5-methyl-2-((1-methyl-Li7-pyrazol-4-yl)amino)pyrimidin-4-yl)phenoxy)propanenitrile (12)

A mixture of 12a (100 mg, 0.34 mmol), K2CO3 (94 mg, 0.68 mmol) and BuOH (26 mg, 0.34 mmol) in acrylonitrile (1.8 g, 34 mmol) was stirred at 120° C. under microwave for 6 hours. The mixture was cooled to RT and concentrated. The residue was purified by Prep-HPLC to afford the title product (4.3 mg, 4% yield) as a yellow solid. LC-MS (Method 1): $t_R$=3.37 min, m/z (M+H)$^+$=353.1. ¾ NMR (400 MHz, DMSO-d$_6$) δ 9.33 (s, 1H), 8.32 (s, 1H), 7.82 (s, 1H), 7.60 (dd, J=1.2, 12.8 Hz, 1H), 7.51 (d, J=8.0 Hz, 1H), 7.48 (s, 1H), 7.33 (t, J=8.8 Hz, 1H), 4.36 (t, J=6.0 Hz, 2H), 3.78 (s, 3H), 3.09 (t, J=5.6 Hz, 2H), 2.21 (s, 3H).

Example 13

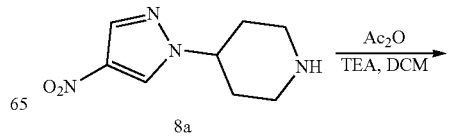

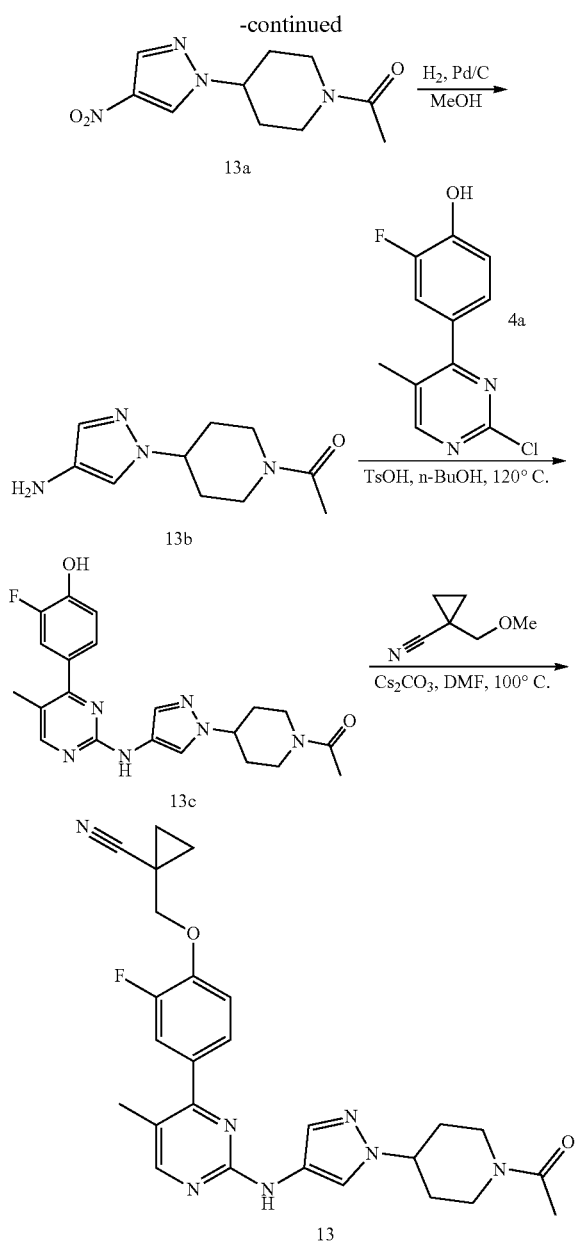

Step 1. 1-(4-(4-Nitro-1//-pyrazol-1-yl)piperidin-1-yl)ethanone (13a)

A solution of compound 8a (1.0 g, 5.096 mmol) and TEA (1.55 g, 15.288 mmol) in DCM (10 mL) was stirred at 0° C. for 10 minutes. Then the mixture was added acetic anhydride (676 mg, 6.625 mmol). The mixture was stirred at RT for 4 hrs. The mixture was diluted with $H_2O$ (50 mL) and extracted with DCM (50 mL*3). The combined organic layers were washed with brine, concentrated and purified by FCC (eluent: DCM: MeOH=30:1) to give the product (963 g, 79% yield) as a white solid. LC-MS (Method 2): $t_R$=1.06 min, m/z (M+H)$^+$=239.1.

Step 2. 1-(4-(4-Amino-1/T-pyrazol-1-yl)piperidin-1-yl)ethanone (13b)

To a solution of compound 13a (460 mg, 1.93 mmol) in MeOH (6 mL) was added Pd/C (100 mg, 10% Pd/C wetted with ca. 55% water). The mixture was stirred at RT under ¾ (1 atm) overnight. The mixture was filtered. The filtrate was concentrated to give the crude product (432 mg, 100% yield) as brown oil. ¾ NMR (400 MHz, CDCl$_3$) δ 7.16 (s, 1H), 7.02 (s, 1H), 4.70 (d, J=13.2 Hz, 1H), 4.22-4.18 (m, 1H), 3.92 (d, J=14.0 Hz, 1H), 3.24-3.17 (m, 1H), 2.76-2.71 (m, 1H), 2.12 (s, 3H), 1.97-1.83 (m, 4H).

Step 3. 1-(4-(4-((4-(3-Fluoro-4-hydroxyphenyl)-5-methylpyrimidin-2-yl)amino)-1/T-pyrazol-1-yl)piperidin-1-yl)ethanone (13c)

Compound 13c (479 mg) was synthesized in 87% yield by utilizing a similar preparative procedure to the first step of Example 6 with compound 4a (350 mg, 1.49 mmol) and compound 13b (402 mg, 1.93 mmol) as starting materials. LC-MS (Method 2): $t_R$=1.17 min, m/z (M+H)$^+$=411.0.

Step 4. 1-((4-(2-((1-(1-Acetylpiperidin-4-yl)-1//-pyrazol-4-yl)amino)-5-methylpyrimidin-4-yl)-2-fluorophenoxy)methyl)cyclopropanecarbonitrile (13)

Compound 13 (19.4 mg) was synthesized in 20% yield by utilizing a similar preparative procedure to the final step of Example 1 with compound 13c (80 mg, 0.195 mmol) and (1-cyanocyclopropyl)methyl methanesulfonate (102 mg, 0.585 mmol) as starting materials. LC-MS (Method 1): $t_R$=3.39 mm, m/z (M+H)$^+$=490.3. ¾ NMR (400 MHz, DMSO-d$_6$) δ 9.33 (s, 1H), 8.32 (s, 1H), 7.91 (s, 1H), 7.62 (d, J=12.4 Hz, 1H), 7.52 (t, J=6.4 Hz, 2H), 7.25 (t, J=8.8 Hz, 1H), 4.45-4.31 (m, 2H), 4.20 (s, 2H), 3.90 (d, J=13.6 Hz, 1H), 3.18 (t, J=12.4 Hz, 1H), 2.70 (t, J=12.8 Hz, 1H), 2.22 (s, 3H), 2.03-1.97 (m, 5H), 1.89-1.79 (m, 1H), 1.73-1.63 (m, 1H), 1.22-1.19 (m, 2H), 0.72-0.70 (m, 2H). $^{19}F$ NMR (376 MHz, DMSO-d$_6$) δ-134.27.

Example 14

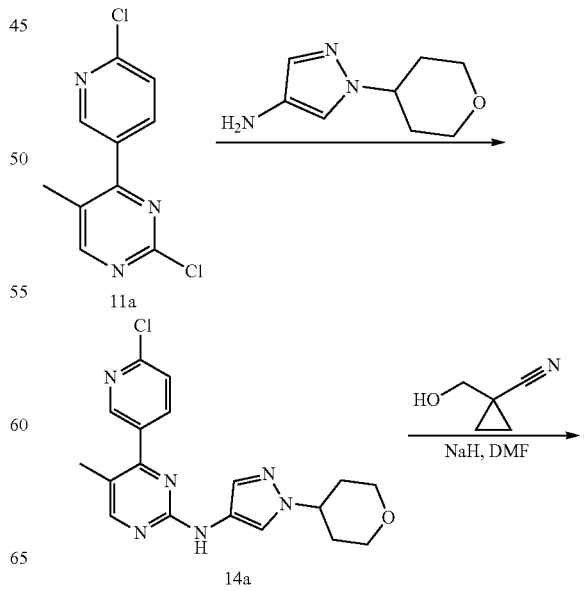

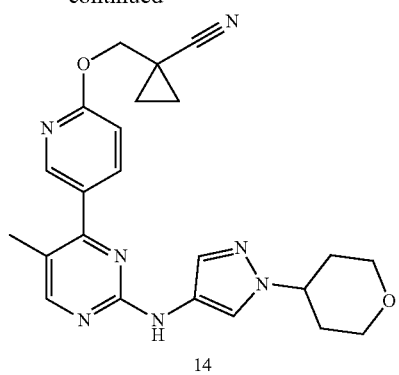

Step 1. 4-(6-Chloropyridin-3-yl)-5-methyl-/V-(1-(tetrahydro-2//-pyran-4-yl)-//-pyrazol-4-yl)pyrimidin-2-amine (14a)

A mixture of compound 11a (380 mg, 1.58 mmol), 1-(tetrahydro-2//-pyran-4-yl)-1H-pyrazol-4-amine (530 mg, 3.17 mmol) and DIPEA (611 mg, 4.74 mmol) in NMP (1 mL) was stirred at 170° C. for 3 hrs in microwave. After cooling down to RT, the mixture was diluted with water (3 mL) and extracted with EtOAc (10 mL*3). The separated organic layer was washed with brine (5 mL*3) and concentrated. The residue was purified by LCC (PE/EtOAc=2/1) to afford the title compound (330 mg, 57% yield) as a yellow solid. LC-MS (Method 2): $t_R$=1.49 min, m/z (M+H)$^+$=371.1.

Step 2. 1-(((5-(5-methyl-2-((1-(tetrahydiO-2//-pyran-4-yl)-1//-pyrazol-4-yl)amino)pyrimidin-4-yl)pyridin-2-yl)oxy)methyl)cyclopropanecarbonitrile (14)

To a solution of 1-(hydroxymethyl)cyclopropanecarbonitrile (37 mg, 0.38 mmol) in THF (1 mL) was added NaH (11 mg, 0.26 mmol, 60% in mineral oil) at RT. After stirring for 2 hrs at RT, compound 14a (70 mg, 0.19 mmol) was added to the reaction. The mixture was stirred for 18 hrs at 80° C. After cooling down to RT, the mixture was diluted with water (1 mL) and extracted with EtOAc (5 mL*3). The combined organic layers were concentrated and the residue was purified by prep-HPLC (Method A) to afford the title compound (17.5 mg, 22% yield) as a yellow solid. LC-MS (Method 1): $t_R$=3.45 mm, m/z (M+H)$^+$=432.2; ¾ NMR (400 MHz, CDCh) δ 8.43 (s, 1H), 8.28 (s, 1H), 7.96 (dd, J=2.4, 8.8 Hz 1H), 7.91 (s, 1H), 7.55 (s, 1H), 6.96 (d, J=8.4 Hz, 1H), 6.78 (m, 1H), 4.40 (s, 2H), 4.33-4.29 (m, 1H), 4.13-4.10 (m, 2H), 3.58-3.51 (m, 2H), 2.29 (s, 3H), 2.12-2.07 (m, 4H), 1.43-1.40 (m, 2H), 1.19-1.16 (m, 2H).

Example 15

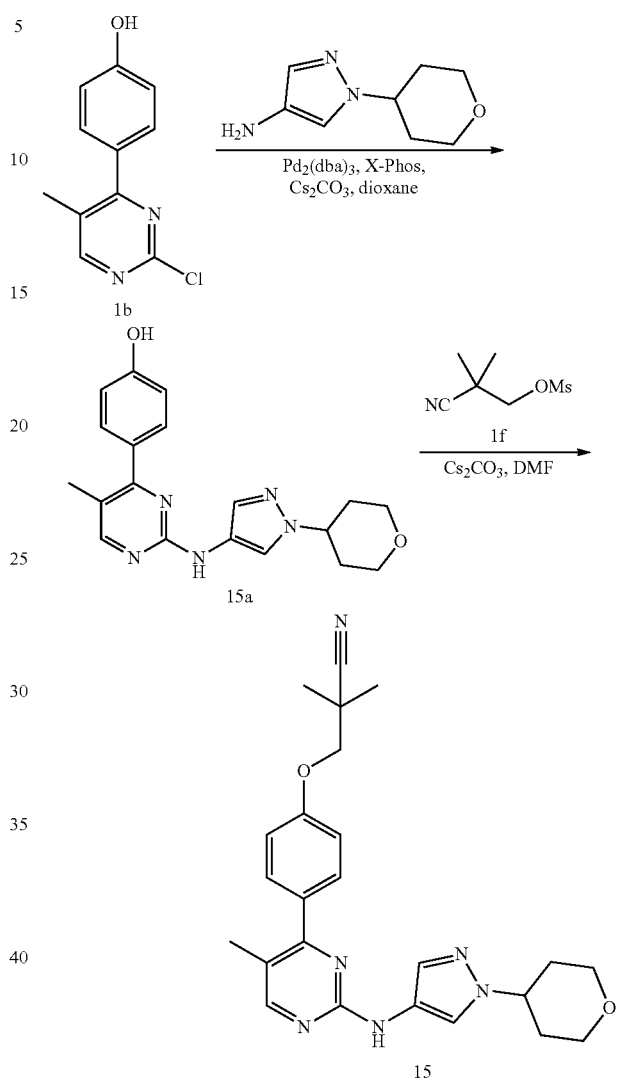

Step 1. 4-(5-Methyl-2-((1-(tetrahydro-2/T-pyran-4-yl)-1/T-pyrazol-4-yl)amino)pyrimidin-4-yl)phenol (15a)

Compound 15a (200 mg) was synthesized in 25% yield by utilizing a similar preparative procedure to the second step of Example 4 with compound 1 b (500 mg, 2.26 mmol) and 1-(tetrahydro-2//-pyran-4-yl)-1//-pyrazol-4-amine (377 mg, 2.26 mmol) as starting materials. LC-MS (Method 2): $t_R$=1.38 mm, m/z (M+H)$^+$=352.1.

Step 2. 2,2-Dimethyl-3-(4-(5-methyl-2-((1-(tetrahydro-2//-pyran-4-yl)-1//-pyrazol-4-yl)amino)pyrimidin-4-yl)phenoxy)propanenitrile (15)

A mixture of compound 15a (50 mg, 0.14 mmol), compound If (50 mg, 0.28 mmol), CS2CO3 (93 mg, 0.28 mmol) in DMF (1 mL) was stirred at 120° C. for 2 hours. The mixture was cooled down to RT, diluted with H2O (10 mL) and extracted with EtOAc (10 mL). The separated organic layer was concentrated. The residue was purified by prep-HPLC (Method A) to give the title compound (30 mg, 50% yield) as white solid. LC-MS (Method 1): $t_R$=3.75 min, m/z (M+H)$^+$=433.3. ¾ NMR (400 MHz, DMSO-$d_6$) δ 9.28 (s, 1H), 8.30 (s, 1H), 7.91 (s, 1H), 7.69 (d, J=8.4 Hz, 2H), 7.55 (s, 1H), 7.13 (d, J=8.8 Hz, 2H), 4.34-4.31 (m, 1H), 4.10 (s, 2H), 3.96-3.93 (m, 2H), 3.48-3.38 (m, 2H), 2.21 (s, 3H), 1.96-1.87 (m, 4H), 1.44 (s, 6H).

Example 16

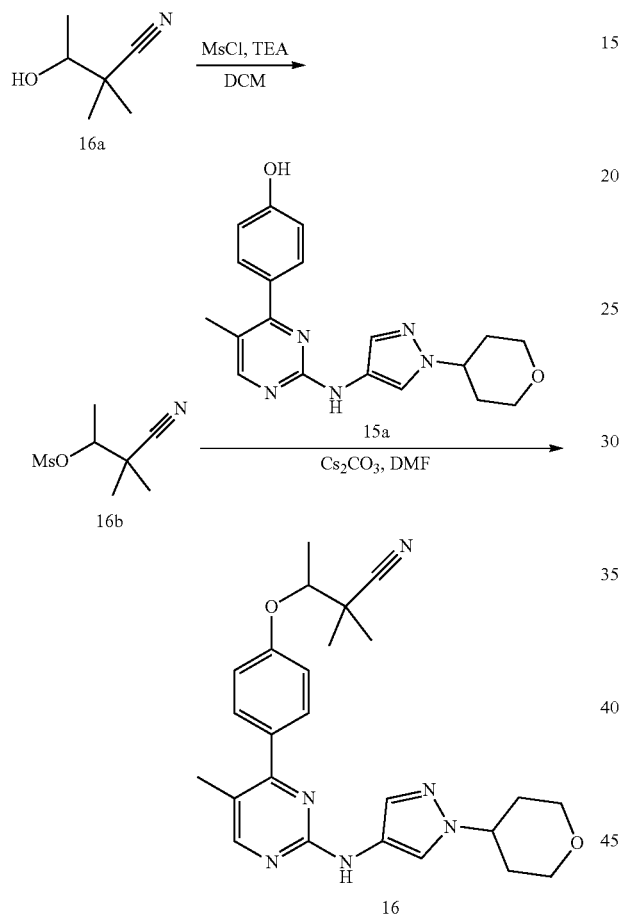

Step 1. 3-Cyano-3-methylbutan-2-yl methanesulfonate (16b)

Compound 16b (300 mg) was synthesized in 89% yield by utilizing a similar preparative procedure to the fourth step of Example 1 with compound 16a (200 mg, 1.77 mmol) as starting materials. ¾ NMR (400 MHz, CDCl₃) δ 4.68-4.63 (m, 1H), 3.11 (s, 3H), 1.43 (d, J=4.8 Hz, 3H), 1.41-1.39 (m, 6H).

Step 2. 2,2-Dimethyl-3-(4-(5-methyl-2-((1-(tetrahydro-2//-pyran-4-yl)-1//-pyrazol-4-yl)amino)pyrimidin-4-yl)phenoxy)butanenitrile (16)

Compound 16 (4 mg) was synthesized in 6% yield by utilizing a similar preparative procedure to the final step of Example 1 with compound 16b (53 mg, 0.28 mmol) and compound 15a (50 mg, 0.14 mmol) as starting materials. LC-MS (Method 1): $t_R$=2.93 min, m/z (M+H)$^+$=447.2. ¾ NMR (400 MHz, CD₃OD) δ 8.27 (s, 1H), 8.05 (s, 1H), 7.70 (d, J=8.8 Hz, 2H), 7.64 (s, 1H), 7.13 (d, J=8.8 Hz, 2H), 4.53-4.48 (m, 1H), 4.40-4.32 (m, 1H), 4.09-4.06 (m, 2H), 3.63-3.55 (m, 2H), 2.28 (s, 3H), 2.09-2.04 (m, 4H), 1.51-1.45 (m, 9H).

Example 17

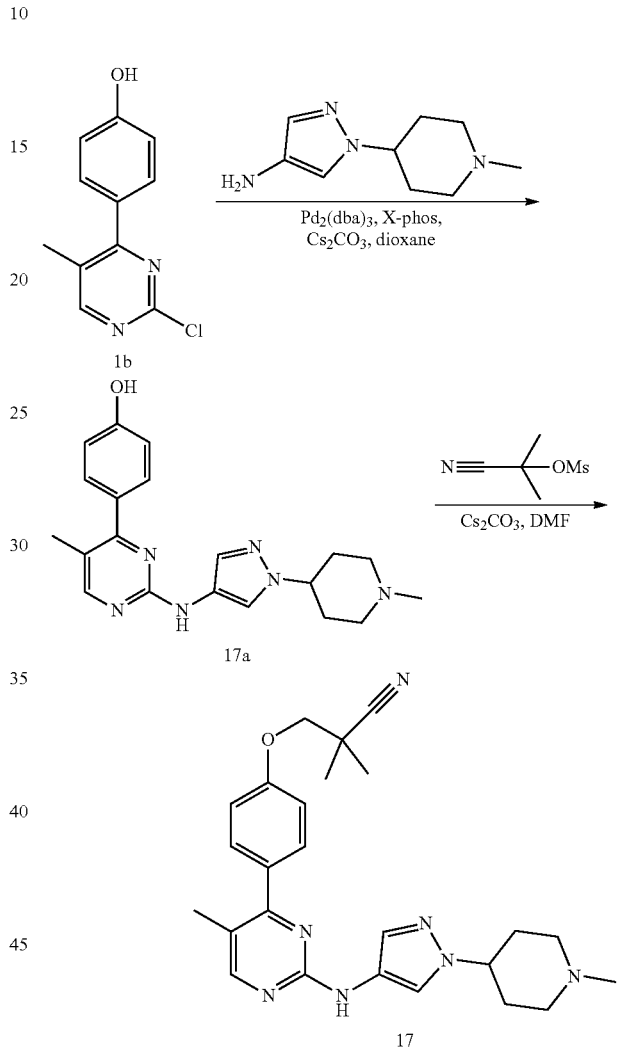

Step 1. 4-(5-Methyl-2-((1-(1-methylpiperidin-4-yl)-1//-pyrazol-4-yl)amino)pyrimidin-4-yl)phenol (17a)

Compound 17a (200 mg) was synthesized in 40% yield by utilizing a similar preparative procedure to second step of Example 1 with compound 1 b (300 mg, 1.36 mmol) and 1-(1-methylpiperidin-4-yl)-1//-pyrazol-4-amine (294 mg, 1.631 mmol) as starting materials. LC-MS (Method 2): $t_R$=1.19 min, m/z (M+H)$^+$=365.2.

Step 2. 2,2-Dimethyl-3-(4-(5-methyl-2-((1-(1-methylpiperidin-4-yl)-1//-pyrazol-4-yl)amino)pyrimidin-4-yl)phenoxy)propanenitrile (17)

Compound 17 (6.9 mg) was synthesized in 11% yield by utilizing a similar preparative procedure to the final step of Example 1 with compound 17a (50 mg, 0.137 mmol) and 2-cyanopropan-2-yl methanesulfonate (49 mg, 0.277 mmol) as starting materials. LC-MS (Method 1): $t_R$=3.48 min, m/z (M+H)$^+$=446.2. ¾ NMR (400 MHz, DMSO-$d_6$) δ 9.27 (s, 1H), 8.29 (s, 1H), 7.88 (s, 1H), 7.69 (d, J=8.4 Hz, 2H), 7.54 (s, 1H), 7.12 (d, J=8.8 Hz, 2H), 4.09 (s, 2H), 4.00-4.07 (m, 1H), 2.83 (d, J=11.6 Hz, 2H), 2.51 (s, 3H), 2.50 (s, 3H), 2.18 (t, J=10.4 Hz, 2H), 1.84-2.05 (m, 4H), 1.44 (s, 6H).

Example 18

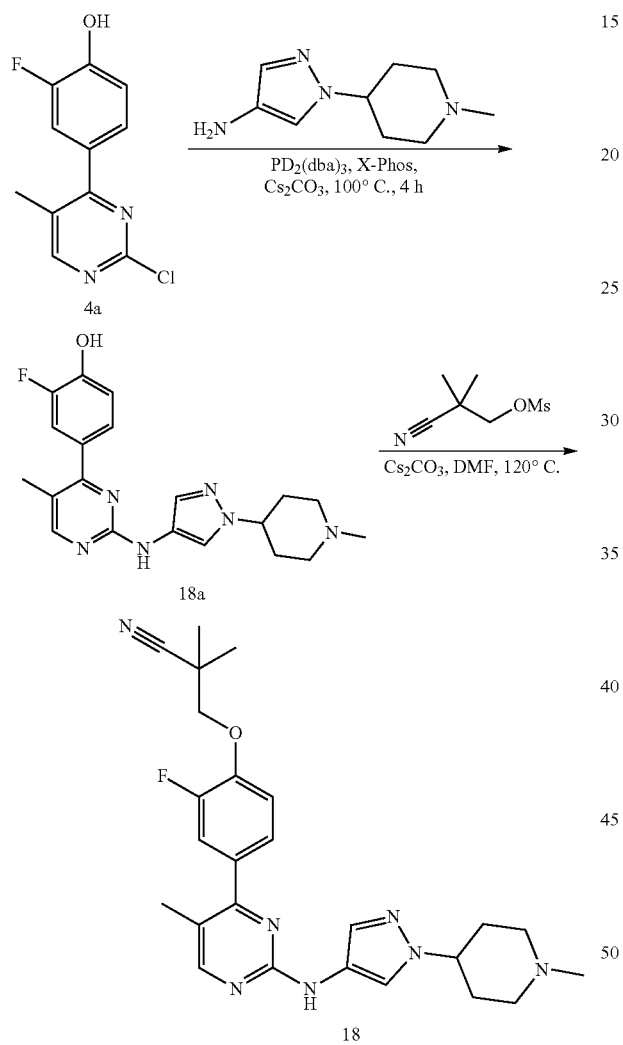

Step 1. 2-Fluoro-4-(5-methyl-2-((1-(1-methylpiperidin-4-yl)-1//-pyrazol-4-yl)amino)pyrimidin-4-yl)phenol (18a)

Compound 18a (500 mg) was synthesized in 86% yield by utilizing a similar preparative procedure to the second step of Example 1 with compound 4a (364 mg, 1.53 mmol) and 1-(1-methylpiperidin-4-yl)-1//-pyrazol-4-amine (330 mg, 1.83 mmol) as starting materials. LC-MS (Method 2): $t_R$=1.36 min, m/z (M+H)$^+$=383.2.

Step 2. 3-(2-FluoiO-4-(5-methyl-2-((1-(1-methylpiperidin-4-yl)-1//-pyrazol-4-yl)amino)pyrimidin-4-yl)phenoxy)-2,2-dimethylpropanenitrile (18)

Compound 18 (12.7 mg) was synthesized in 13% yield by utilizing a similar preparative procedure to the final step of Example 1 with compound 18a (80 mg, 0.209 mmol) and 2-cyano-2-methylpropyl methanesulfonate (56 mg, 0.314 mmol) as starting materials. LC-MS (Method 1): $t_R$=3.80 mm, m/z (M+H)$^+$=464.2. ¾ NMR (400 MHz, DMSO-$d_6$) δ 9.31 (s, 1H), 8.32 (s, 1H), 7.89 (s, 1H), 7.62 (d, J=13.6 Hz, 1H), 7.53 (d, J=4.8 Hz, 2H), 7.33 (t, J=8.4 Hz, 1H), 4.19 (s, 2H), 4.05-4.03 (m, 1H), 2.84 (d, J=11.6 Hz, 2H), 2.22 (s, 3H), 2.20 (s, 3H), 2.05 (t, J=10.8 Hz, 2H), 1.97-1.87 (m, 4H), 1.45 (s, 6H). $^{19}$F NMR (400 MHz, DMSO-$d_6$) δ-134.84.

Example 19

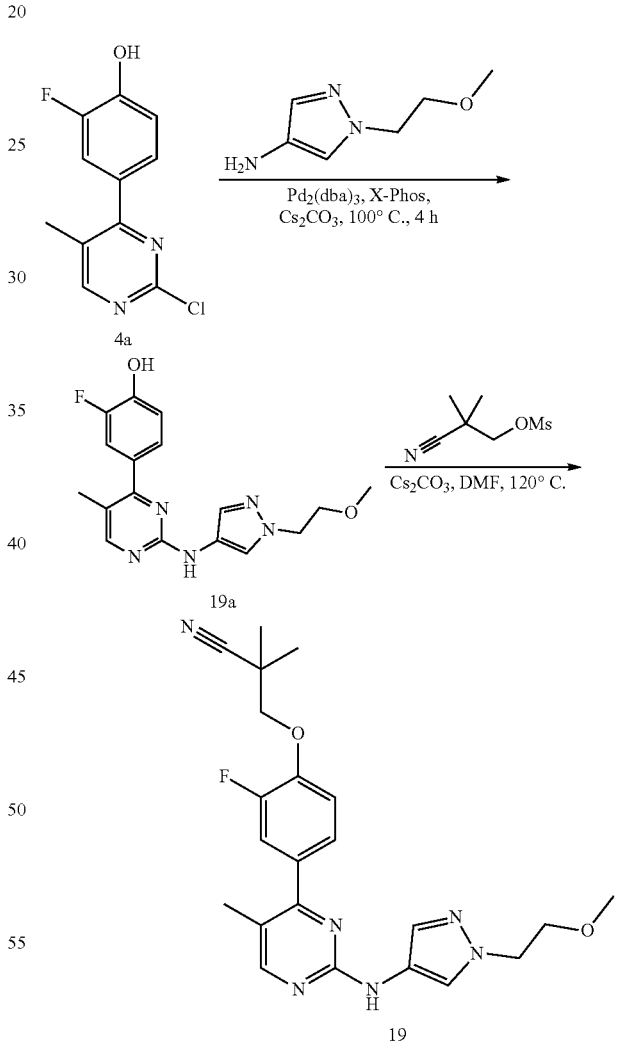

Step 1. 2-Fuoro-4-(2-((1-(2-methoxyethyl)-1//-pyrazol-4-yl)amino)-5-methylpyrimidin-4-yl)phenol (19a)

Compound 19a (390 mg) was synthesized in 68% yield by utilizing a similar preparative procedure to the second step of Example 1 with compound 4a (400 mg, 1.68 mmol) and 1-(2-methoxy ethyl)-1if-pyrazol-4-amine (284 mg, 2.02 mmol) as starting materials. LC-MS (Method 2): $t_R$=1.40 min, m/z (M+H)$^+$=344.2.

Step 2. 3-(2-Fuoro-4-(2-((1-(2-methoxyethyl)-1//-pyrazol-4-yl)amino)-5-methylpyrimidin-4-yl)phenoxy)-2,2-dimethylpropanenitrile (19)

Compound 19 (24.1 mg) was synthesized in 22% yield by utilizing a similar preparative procedure to the final step of Example 1 with compound 19a (87 mg, 0.25 mmol) and 2-cyano-2-methylpropyl methanesulfonate (67 mg, 0.38 mmol) as starting materials. LC-MS (Method 1): $t_R$=3.31 min, m/z (M+H)$^+$=425.2. $^1$H NMR (400 MHz, DMSO-d$_6$) δ 9.33 (s, 1H), 8.33 (s, 1H), 7.88 (s, 1H), 7.61 (dd, J=2.0, 12.4 Hz, 1H), 7.52-7.50 (m, 2H), 7.34 (t, J=8.8 Hz, 1H), 4.19 (t, J=4.8 Hz, 4H), 3.65 (t, J=5.2 Hz, 2H), 3.23 (s, 3H), 2.23 (s, 3H), 1.45 (s, 6H).

Example 20

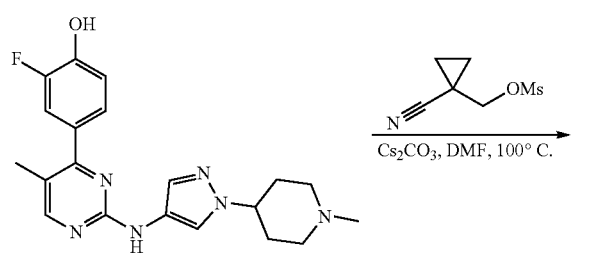

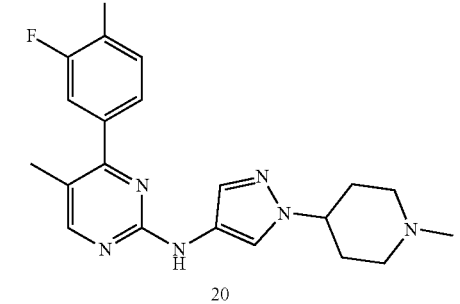

1-((2-Fluoro-4-(5-methyl-2-((1-(1-methylpiperidin-4-yl)-1//-pyrazol-4-yl)amino)pyrimidin-4-yl)phenoxy)methyl)cyclopropanecarbonitrile (20)

Compound 20 (16.0 mg) was synthesized in 17% yield by utilizing a similar preparative procedure to the final step of Example 1 with compound 18a (80 mg, 0.209 mmol) and (1-cyanocyclopropyl)methyl methanesulfonate (55 mg, 0.314 mmol) as starting materials. LC-MS (Method 1): $t_R$=2.87 mm, m/z (M+H)$^+$=462.2. ¾ NMR (400 MHz, DMSO-d$_6$) δ 9.30 (s, 1H), 8.32 (s, 1H), 7.89 (s, 1H), 7.62 (d, J=12.0 Hz, 1H), 7.52-7.50 (d, J=9.6 Hz, 2H), 7.25 (t, J=8.8 Hz, 1H), 4.20 (s, 2H), 4.06-4.00 (m, 1H), 2.84 (d, J=11.2 Hz, 2H), 2.22 (s, 3H), 2.19 (s, 3H), 2.04 (t, J=11.2 Hz, 2H), 1.97-1.87 (m, 4H), 1.43-1.40 (m, 2H), 1.22-1.19 (m, 2H). $^{19}$F NMR (400 MHz, DMSO-d$_6$) δ-134.30.

Example 21

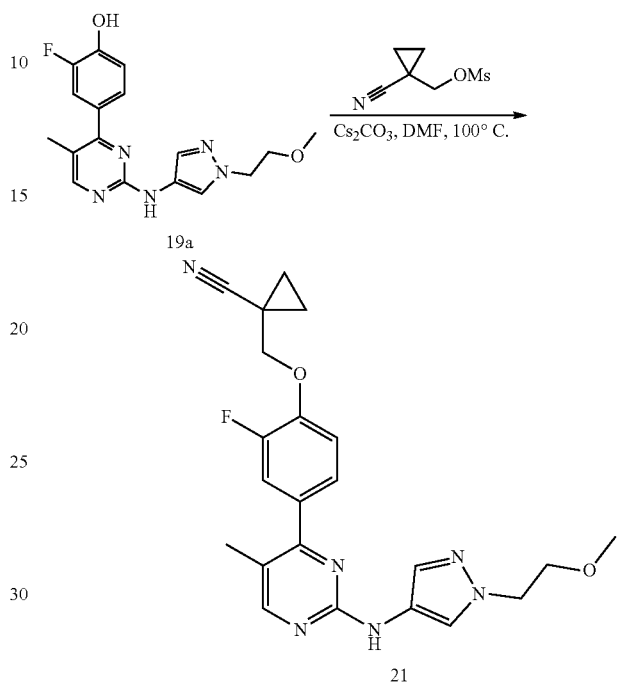

1-((2-FluoiO-4-(2-((1-(2-methoxyethyl)-1//-pyrazol-4-yl)amino)-5-methylpyrimidin-4-yl)phenoxy)methyl)cyclopropanecarbonitrile (21)

Compound 21 (17.6 mg) was synthesized in 16% yield by utilizing a similar preparative procedure to the final step of Example 1 with compound 19a (87 mg, 0.25 mmol) and (1-cyanocyclopropyl)methyl methanesulfonate (67 mg, 0.38 mmol) as starting materials. LC-MS (Method 1): $t_R$=3.61 mm, m/z (M+H)$^+$=423.2. $^1$H NMR (400 MHz, DMSO-d$_6$) δ 9.33 (s, 1H), 8.33 (s, 1H), 7.88 (s, 1H), 7.61 (d, J=12.0 Hz, 1H), 7.51 (d, J=4.8 Hz, 2H), 7.26 (t, J=8.8 Hz, 1H), 4.19 (t, J=6.4 Hz, 4H), 3.65 (t, J=5.2 Hz, 2H), 3.23 (s, 3H), 2.22 (s, 3H), 1.43-1.40 (m, 2H), 1.22-1.19 (m, 2H).

Example 22

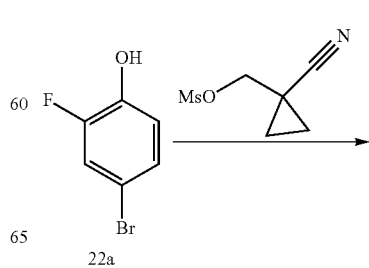

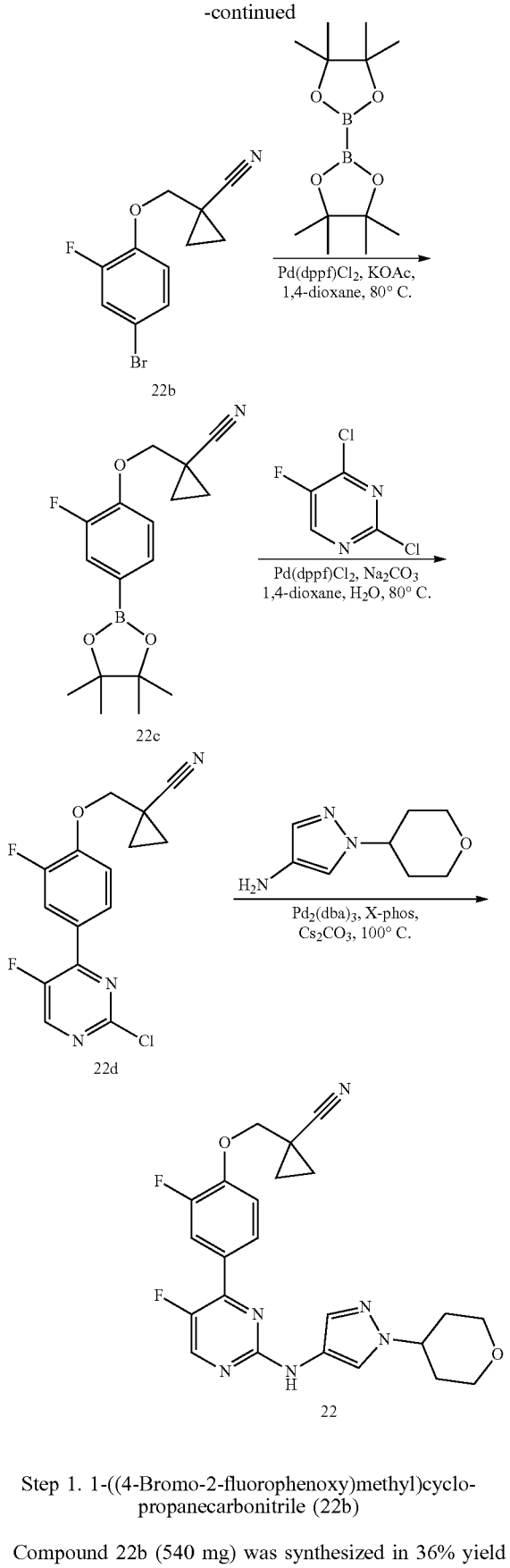

of Example 10 with compound 22a (1.05 g, 5.49 mmol) and (1-cyanocyclopropyl)methyl methanesulfonate (1.44 g, 8.25 mmol) as starting materials. $^1$H NMR (400 MHz, CDCl$_3$) δ 7.27-7.24 (m, 1H), 7.19 (d, J=8.4 Hz, 1H), 6.88 (d, J=8.4 Hz, 1H), 4.02 (s, 2H), 1.42-1.39 (m, 2H), 1.14-1.10 (m, 2H).

Step 2. 1-((2-Fluoro-4-(4,4,5,5-tetramethyl-1,3,2-dioxaborolan-2-yl)phenoxy)methyl)cyclopropanecarbonitrile (22c)

Compound 22c (crude) was synthesized by utilizing a similar preparative procedure to the second step of Example 10 with compound 22b (440 mg, 1.63 mmol) and 4,4,4',4',5,5,5',5'-octamethyl-2,2'-bi(1,3,2-dioxaborolane) (455 mg, 1.79 mmol) as starting materials. The crude product was used for next step without further purification.

Step 3. 1-((4-(2-Chloro-5-fluoropyrimidin-4-yl)-2-fluorophenoxy)methyl)cyclopropanecarbonitrile (22d)

Compound 22d (358 mg) was synthesized in 68% yield by utilizing a similar preparative procedure to the third step of Example 10 with compound 22c (517 mg, 1.63 mmol) and 2,4-dichloro-5-fluoropyrimidine (327 mg, 1.96 mmol) as starting materials. LC-MS (Method 2): t$_R$=1.67 mm, m/z (M+H)$^+$=322.0.

Step 4. 1-((2-Fluoro-4-(5-fluoro-2-((1-(tetrahydro-2//-pyran-4-yl)-1//-pyrazol-4-yl)amino)pyrimidin-4-yl)phenoxy)methyl)cyclopropanecarbonitrile (22)

Compound 22 (7.8 mg) was synthesized in 7% yield by utilizing a similar preparative procedure to the second step of Example 1 with compound 22d (80 mg, 0.25 mmol) and 1-(tetrahydro-2//-pyran-4-yl)-1//-pyrazol-4-amine (50 mg, 0.299 mmol) as starting materials. LC-M S (Method 1): t$_R$=3.58 mm, m/z (M+H)$^+$=453.2. $^1$H NMR (400 MHz, DMSO-d$_6$) δ 9.55 (s, 1H), 8.54 (d, J=3.6 Hz, 1H), 7.94-7.86 (m, 3H), 7.57 (s, 1H), 7.33 (t, J=8.8 Hz, 1H), 4.37-4.33 (m, 1H), 4.24 (s, 2H), 3.96 (d, J=10.4 Hz, 2H), 3.46 (t, J=10.8 Hz, 2H), 1.96-1.90 (m, 4H), 1.43-1.42 (m, 2H), 1.23-1.21 (m, 2H). $^{19}$F NMR (376 MHz, DMSO-d$_6$) δ-133.62, −153.22.

Example 23

Step 1. 1-((4-Bromo-2-fluorophenoxy)methyl)cyclopropanecarbonitrile (22b)

Compound 22b (540 mg) was synthesized in 36% yield by utilizing a similar preparative procedure to the first step

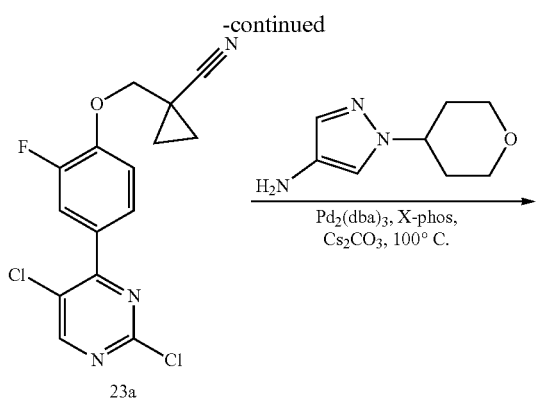

Example 24

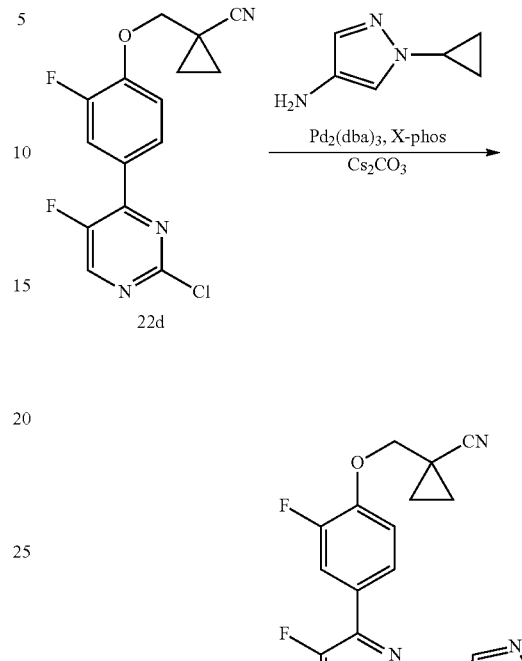

Step 1. 1-((4-(2,5-Dichloropyrimidin-4-yl)-2-fluorophenoxy)methyl)cyclopropanecarbonitrile (23a)

A mixture of compound 22c (449 mg, 1.415 mmol), 2,4,5-trichloropyrimidine (306 mg, 1.698 mmol), Pd(PPh₃)₄ (164 mg, 0.1415 mmol) and Na2CO3 (300 mg, 2.83 mmol) in 1,4-dioxane/PhO (6 mL/1.5 mL) was stirred at 90° C. under N2for 2.5 hrs. The mixture was cooled down to RT and filtered. The filtrate was concentrated and the residue was purified by column chromatography on silica gel (eluent: PE: EtOAc=6:1) to give the product (317 mg, 67% yield) as a yellow solid. LC-MS (Method 2): t$_R$=1.73 min, m/z (M+H)⁺=338.1.

Step 2. 1-((4-(5-Chloro-2-((1-(tetrahydro-2//-pyran-4-yl)-1//-pyrazol-4-yl)amino)pyrimidin-4-yl)-2-fluorophenoxy)methyl)cyclopropanecarbonitrile (23)

A mixture of compound 23a (80 mg, 0.237 mmol), 1-(tetrahydro-2//-pyran-4-yl)-1H-pyrazol-4-amine (48 mg, 0.285 mmol), Pd2(dba)₃ (22 mg, 0.0237 mmol), X-Phos (23 mg, 0.0474 mmol) and Cs₂CO₃ (116 mg, 0.356 mmol) in 1,4-dioxane(1 mL) was stirred at 100° C. under N2 overnight. The mixture was cooled down to RT and filtered. The filtrate was concentrated and the residue was purified by prep-HPLC (Method A) to give the product (5.9 mg, 5% yield) as a yellow solid. LC-MS (Method 1): t$_R$=2.77 mm, m/z (M+H)⁺=469.1. ¹H NMR (400 MHz, DMSO-d₆) δ 9.76 (s, 1H), 8.52 (s, 1H), 7.91 (s, 1H), 7.78-7.70 (m, 2H), 7.56 (s, 1H), 7.29 (t, J=8.8 Hz, 1H), 4.38-4.31 (m, 1H), 4.22 (s, 2H), 3.94 (d, J=11.6 Hz, 2H), 3.48-3.42 (m, 2H), 1.96-1.84 (m, 4H), 1.43-1.40 (m, 2H), 1.22-1.19 (m, 2H). ¹⁹F NMR (376 MHz, DMSO-d₆) δ-134.17.

1-((4-(2-((1-Cyclopropyl-1//-pyrazol-4-yl)amino)-5-fluoropyrimidin-4-yl)-2-fluorophenoxy)methyl)cyclopropanecarbonitrile (24)

Compound 24 (10 mg) was synthesized in 10% yield by utilizing a similar preparative procedure to the second step of Example 1 with compound 22d (80 mg, 0.25 mmol) and 1-cyclopropyl-1/-pyrazol-4-amine (36.9 mg, 0.3 mmol) as starting materials. LC-MS (Method 1): t$_R$=3.84 min, m/z (M+H)⁺=409.2; ¾ NMR (400 MHz, CD₃OD) δ 8.37 (d, J=4.4 Hz, 1H), 7.99-7.93 (m, 3H), 7.59 (s, 1H), 7.24 (t, J=8.4 Hz, 1H), 4.19 (s, 2H), 3.65-3.60 (m, 1H), 1.43 (dd, J=5.2, 7.2 Hz, 2H), 1.25 (dd, J=6.0, 7.6 Hz, 2H), 1.09-1.04 (m, 4H).

Example 25

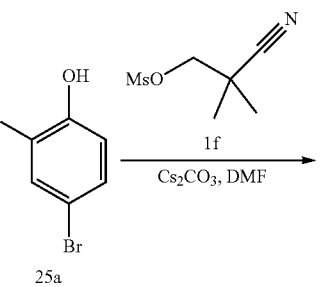

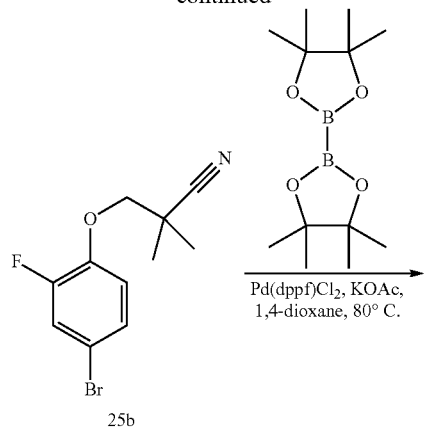

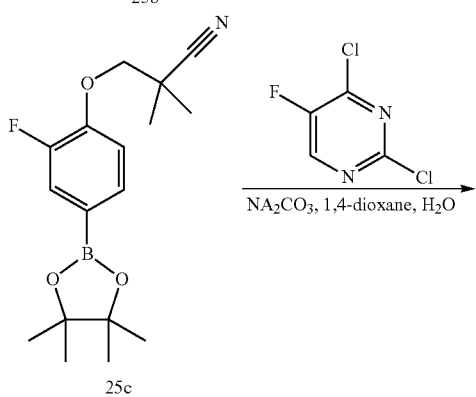

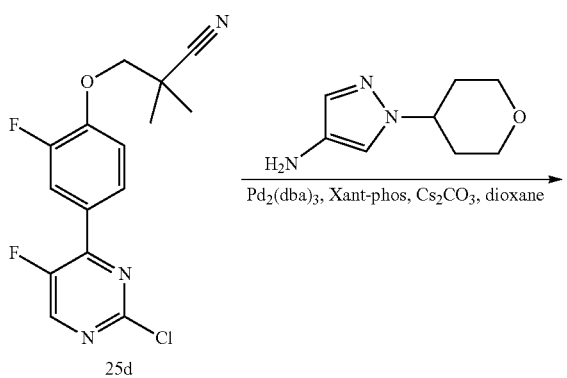

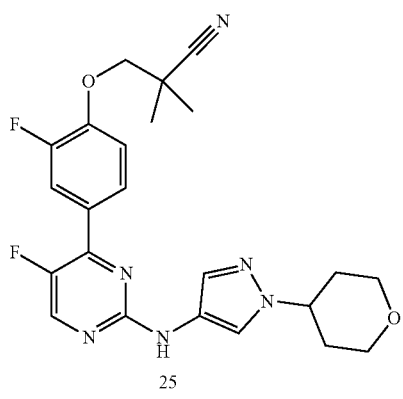

Step 1. 3-(4-Bromo-2-fluorophenoxy)-2,2-dimethyl-propanenitrile (25b)

To a mixture of 4-bromo-2-fluorophenol (482 mg, 2.524 mmol) and compound If (670 mg, 3.785 mmol) in DMF (10 mL) was added CS2CO3 (1.645 g, 5.046 mmol). The mixture was stirred at 120° C. for 16 hrs. The mixture was cooled down to RT, filtered and the filtrate was concentrated to afford the residue. The residue was washed with PE/EtOAc/DCM (10 mL, v:v:v=1:1:1). The filtrate was concentrated to afford the product (800 mg, 99.6% yield) as brown oil. M NMR (400 MHz, CDCh) δ 7.28-7.21 (m, 1H), 7.21-7.18 (m, 1H), 6.87 (t, J=8.8 Hz, 1H), 3.94 (s, 2H), 1.49 (s, 6H).

Step 2. 3-(2-Fluoro-4-(4,4,5,5-tetramethyl-1,3,2-dioxaborolan-2-yl)phenoxy)-2,2-dimethylpropanenitrile (25c)

A mixture of compound 25b (400 mg, 1.471 mmol) and 4,4,4',4',5,5,5',5'-octamethyl-2,2'-bi(1,3,2-dioxaborolane) (411 mg, 1.618 mmol) in 1,4-dioxane (10 mL) was added Pd(dppf)Cl2 (215 mg, 0.294 mmol) and KOAc (288 mg, 2.939 mmol) under N2. The mixture was stirred at 80° C. for 3 hrs. The reaction mixture was used to the next step without purification.

Step 3. 3-(4-(2-Chloro-5-fluoropyrimidin-4-yl)-2-fluorophenoxy)-2,2-dimethylpropanenitrile (25d)

To the reaction mixture of step 2 was added 2,4-dichloro-5-fluoropyrimidine (184 mg, 1.102 mmol), $Na_2CO_3$ (234 mg, 2.21 mmol), H2O (1 mL), 1,4-dioxane (3 mL) and Pd(dppf)Cl2 (81 mg, 0.11 mmol) under N2. The mixture was stirred at 80° C. for 1 hour. The mixture was cooled down to RT, filtered and the filtrate was concentrated. The residue was purified by column chromatography on silica gel (PE:EtOAc=10:1) to afford the product (160 mg, 34% yield for three steps) as a white solid. LC-MS (Method 2): $t_R$=1.51 min, m/z (M+H)+=323.9.

Step 4. 3-(2-FluoiO-4-(5-fluoiO-2-((1-(tetrahydiO-2//-pyran-4-yl)-//-pyrazol-4-yl)amino)pyrimidin-4-yl)phenoxy)-2,2-dimethylpropanenitrile (25)

To a mixture of compound 25d (70 mg, 0.22 mmol), 1-(tetrahydro-2//-pyran-4-yl)-H-pyrazol-4-amine (51 mg, 0.31 mmol), Xant-phos (21 mg, 0.04 mmol) in 1,4-dioxane (3 mL) was added $CS_2CO_3$ (141 mg, 0.43 mmol) and $Pd_2(dba)_3$ (20 mg, 0.02 mmol) under N2. The mixture was stirred at 110° C. for 16 hrs. The mixture was filtered and the filtrate was concentrated. The crude product was purified by prep-HPLC (Method A) to afford the product (10.2 mg, 10.4% yield) as a yellow solid. LC-MS (Method 1): $t_R$=3.22 min, m/z (M+H)+=455.2. ¾ NMR (400 MHz, DMSO-$d_6$) δ 9.60 (s, 1H), 8.58 (d, J=5.2 Hz, 1H), 7.98-7.91 (m, 3H), 7.60 (s, 1H), 7.44 (t, J=12.0 Hz, 1H), 4.43-4.36 (m, 1H), 4.25 (s, 2H), 3.99 (d, J=14.8 Hz, 2H), 3.53-3.37 (m, 2H), 2.01-1.92 (m, 4H), 1.43 (s, 6H).

Example 26

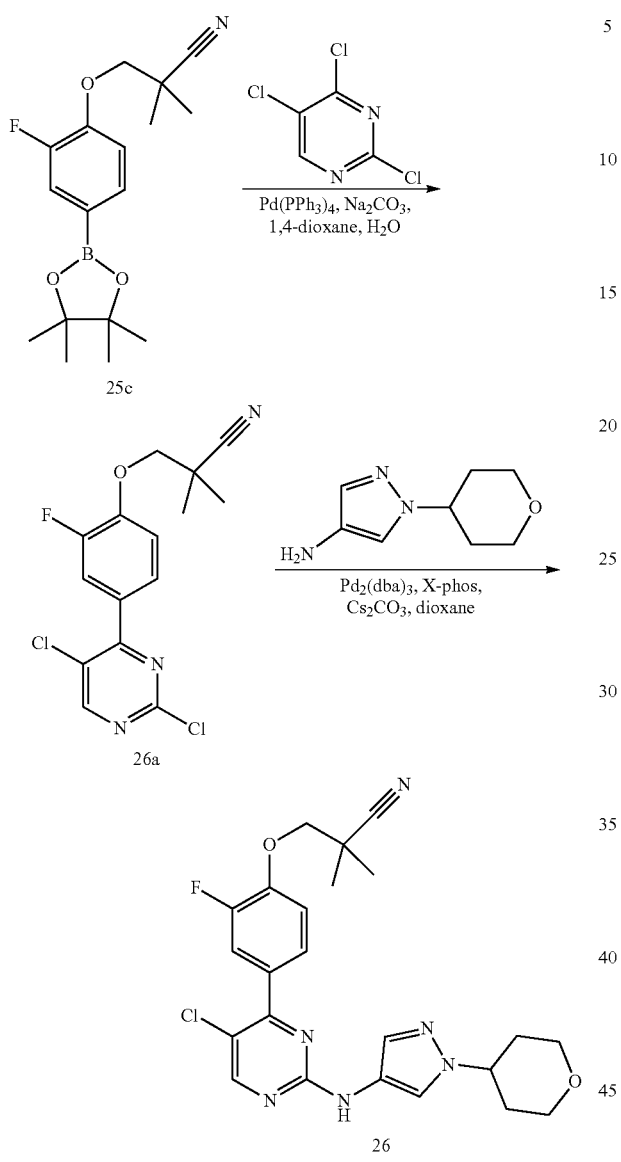

Step 1. 3-(4-(2,5-Dichloropyrimidin-4-yl)-2-fluorophenoxy)-2,2-dimethylpropanenitrile (26a)

Compound 26a (0.65 g) was synthesized in 47% yield by utilizing a similar preparative procedure to the first step of Example 1 with compound 25c (1.29 g, 4.04 mmol) and 2,4,5-trichloropyrimidine (728 mg, 4.04 mmol) as starting materials. LC-MS (Method 2): $t_R$=1.76 min, m/z (M+H)$^+$=340.0.

Step 2. 3-(4-(5-Chloro-2-((1-(tetrahydro-2//-pyran-4-yl)-1//-pyrazol-4-yl)amino)pyrimidin-4-yl)-2-fluorophenoxy)-2,2-dimethylpropanenitrile (26)

Compound 26 (4.1 mg) was synthesized in 3% yield by utilizing a similar preparative procedure to the second step of Example 1 with compound 26a (90 mg, 0.26 mmol) and 1-(tetrahydro-2//-pyran-4-yl)-1//-pyrazol-4-amine (53 mg, 0.32 mmol) as starting materials. The title compound was purified by prep-HPLC (method B). LC-MS (Method 1): $t_R$=3.99 min, m/z (M+H)$^+$=471.2. $^1$H NMR (400 MHz, DMSO-d$_6$) δ 9.78 (s, 1H), 8.53 (s, 1H), 7.92 (s, 1H), 7.91-7.73 (m, 2H), 7.57 (s, 1H), 7.40-7.35 (m, 1H), 4.38-4.32 (m, 1H), 4.42 (s, 2H), 3.95 (d, J=10.4 Hz, 2H), 3.48-3.42 (m, 2H), 1.98-1.86 (m, 4H), 1.45 (s, 6H).

Example 27

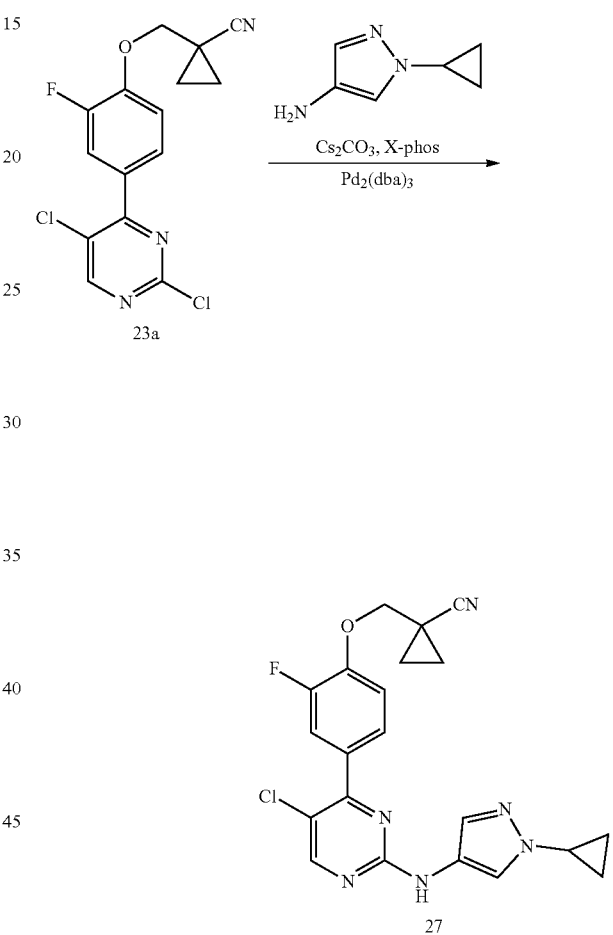

1-((4-(5-Chloro-2-((1-cyclopropyl-1//-pyrazol-4-yl)amino)pyrimidin-4-yl)-2-fluorophenoxy)methyl)cyclopropanecarbonitrile (27)

Compound 27 (10 mg) was synthesized in 10% yield by utilizing a similar preparative procedure to the second step of Example 1 with compound 23a (80 mg, 0.24 mmol) and 1-cyclopropyl-1//-pyrazol-4-amine (35 mg, 0.29 mmol) as starting materials. LC-MS (Method 1): $t_R$=2.87 min, m/z (M+H)+=425.1; ¾ NMR (400 MHz, CD$_3$OD) δ 8.36 (s, 1H), 7.87 (s, 1H), 7.63 (t, J=7.2 Hz, 2H), 7.47 (s, 1H), 7.12 (t, J=8.4 Hz, 1H), 4.07 (s, 2H), 3.52-3.48 (m, 1H), 1.32 (dd, J=5.2, 7.6 Hz, 2H), 1.13 (dd, J=5.2, 7.6 Hz, 2H), 0.96-0.89 (m, 4H).

Example 28

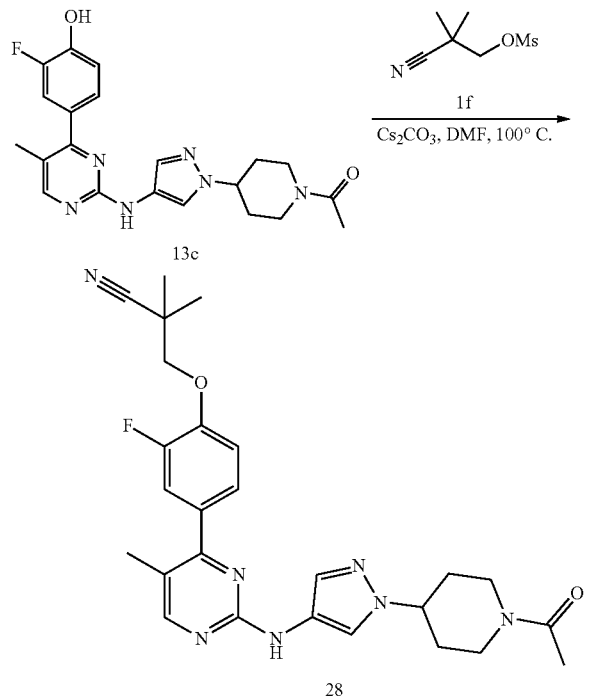

3-(4-(2-((1-(1-Acetylpiperidin-4-yl)-1//-pyrazol-4-yl)amino)-5-methylpyrimidin-4-yl)-2-fluorophenoxy)-2,2-dimethylpropanenitrile (28)

Compound 28 (15.1 mg) was synthesized in 25% yield by utilizing a similar preparative procedure to the final step of Example 1 with compound 13c (50 mg, 0.22 mmol) and compound 1f (65 mg, 0.366 mmol) as starting materials. LC-MS (Method 1): $t_R$=3.35 min, m/z (M+H)$^+$=492.2. ¾ NMR (400 MHz, DMSO-d$_6$) δ 9.35 (s, 1H), 8.32 (s, 1H), 7.91 (s, 1H), 7.62 (d, J=12.4 Hz, 1H), 7.54-7.52 (m, 2H), 7.33 (t, J=8.4 Hz, 1H), 4.45-4.33 (m, 2H), 4.19 (s, 2H), 3.89 (d, J=14.0 Hz, 1H), 3.21-3.15 (m, 1H), 2.69 (t, J=12.8 Hz, 1H), 2.22 (s, 3H), 2.03 (s, 3H), 2.00-1.94 (m, 2H) 1.89-1.79 (m, 1H), 1.73-1.62 (m, 1H), 1.45 (s, 6H). $^{19}$F NMR (376 MHz, DMSO-d$_6$) δ-134.83.

Example 29

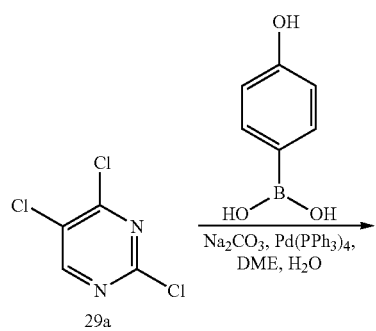

Step 1. 4-(2,5-Dichloropyrimidin-4-yl)phenol (29b)

Compound 29b (1.1 g) was synthesized in 85% yield by utilizing a similar preparative procedure to the first step of Example 1 with compound 29a (1.0 g, 5.46 mmol) and (4-hydroxyphenyl)boronic acid (0.68 g, 4.92 mmol) as starting materials. $^1$H NMR (400 MHz, DMSO-d$_6$) δ 8.83 (s, 1H), 8.14 (s, 1H), 7.88 (d, J=8.8 Hz, 2H), 7.26 (d, J=8.8 Hz, 2H).

Step 2. 4-(5-ChloiO-2-((1-methyl-1//-pyrazol-4-yl)amino)pyrimidin-4-yl)phenol (29c)

Compound 29c (380 mg) was synthesized in 80% yield by utilizing a similar preparative procedure to the second step of Example 1 with compound 29b (300 mg, 1.24 mmol) and 1-methyl-lif-pyrazol-4-amine (144 mg, 1.48 mmol) as starting materials. LC-MS (Method 2): $t_R$=1.56 min, m/z (M+H)$^+$=302.0.

Step 3. 3-(4-(5-ChloiO-2-((1-methyl-1//-pyrazol-4-yl)amino)pyrimidin-4-yl)phenoxy)-2,2-dimethylpropanenitrile (29)

Compound 29 (12.9 mg) was synthesized in 10% yield by utilizing a similar preparative procedure to the final step of Example 1 with compound 29c (100 mg, 0.33 mmol) and compound 1f (117 mg, 0.66 mmol) as starting materials. LC-MS (Method 1): $t_R$=3.85 min, m/z (M+H)$^+$=383.2. 1H NMR (400 MHz, CDCl3) δ 8.37 (s, 1H), 7.89 (d, J=8.7 Hz, 2H), 7.81 (s, 1H), 7.50 (s, 1H), 7.03 (d, J=8.8 Hz, 2H), 3.98 (s, 2H), 3.89 (s, 3H), 1.56 (s, 6H).

Example 30

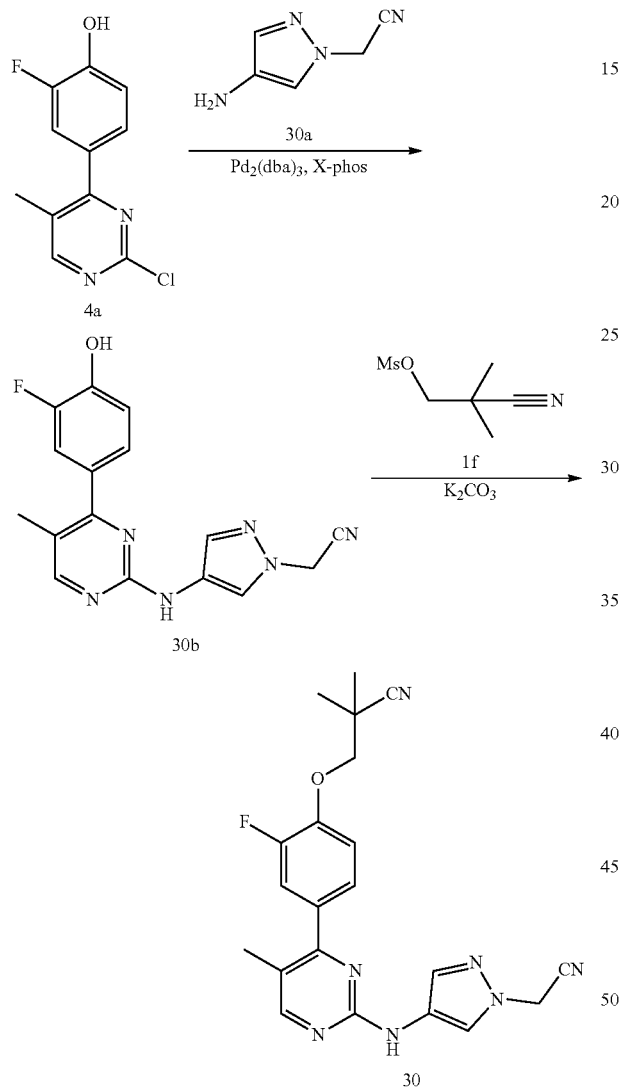

Step 1. 2-(4-((4-(3-Fuoro-4-hydroxyphenyl)-5-methylpyrimidin-2-yl)amino)-1//-pyrazol-1-yl)acetonitrile (30b)

Compound 30b (160 mg) was synthesized in 30% yield by utilizing a similar preparative procedure to the second step of Example 1 with compound 4a (400 mg, 1.68 mmol) and compound 30a (280 mg, 2.02 mmol) as starting materials. LC-MS (Method 2): t¾=1.25 min, m/z (M+H)$^+$=325.1.

Step 2. 3-(4-(2-((1-(Cyanomethyl)-1//-pyrazol-4-yl) amino)-5-methylpyrimidin-4-yl)-2-fluorophenoxy)-2,2-dimethylpropanenitrile (30)

Compound 30 (4.7 mg) was synthesized in 6% yield by utilizing a similar preparative procedure to the final step of Example 1 with compound 30b (70 mg, 0.22 mmol) and compound 1f (57 mg, 0.32 mmol) as starting materials. LC-MS (Method 1): $t_R$=3.61 min, m/z (M+H)$^+$=406.2. ¾ NMR (400 MHz, CDCl3) δ 8.30 (s, 1H), 8.10 (s, 1H), 7.56 (s, 1H), 7.46-7.39 (m, 2H), 7.09 (t, J=8.0 Hz, 1H), 6.90 (s, 1H), 5.04 (s, 2H), 4.05 (s, 2H), 2.28 (s, 3H), 1.54 (s, 6H).

Example 31

1-((4-(2-((1-(Cyanomethyl)-1//-pyrazol-4-yl)amino)-5-methylpyrimidin-4-yl)-2-fluorophenoxy)methyl) cyclopropanecarbonitrile (31)

Compound 31 (95 mg) was synthesized in 100% yield by utilizing a similar preparative procedure to the final step of Example 1 with compound 30b (70 mg, 0.22 mmol) and (1-cyanocyclopropyl)methyl methanesulfonate (57 mg, 0.32 mmol) as starting materials. LC-MS (Method 1): $t_R$=2.99 min, m/z (M+H)$^+$=404.2. ¾ NMR (400 MHz, CDCl3) δ 8.34 (s, 1H), 8.15 (s, 1H), 7.73 (s, 1H), 7.58-7.50 (m, 2H), 7.25 (t, J=10.8 Hz, 1H), 5.31 (s, 2H), 4.20 (s, 2H), 2.31 (s, 3H), 1.48-1.44 (m, 2H), 1.29-1.25 (m, 2H).

Example 32

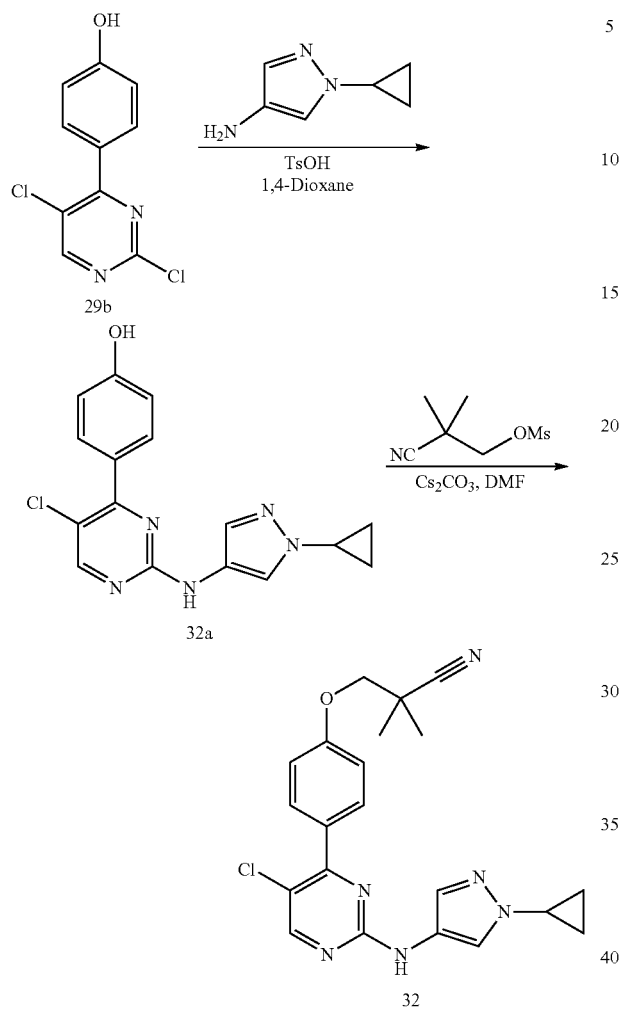

Step 1. 4-(5-Chloro-2-((1-cyclopropyl-1H-pyrazol-4-yl)amino)pyrimidin-4-yl)phenol (32a)

A solution of compound 29b (200 mg, 0.84 mmol), 1-cyclopropyl-lif-pyrazol-4-amine (155 mg, 1.26 mmol) and TsOH (15 mg, 0.084 mmol) in 1,4-dioxane (2 mL) was stirred at 100° C. overnight. The mixture was concentrated in vacuo. The residue was purified by flash chromatography (PE: EtOAc=2:1) to give the compound (120 mg, 44% yield) as a white solid. ¾ NMR (400 MHz, DMSO-$d_6$) δ 10.00 (s, 1H), 9.66 (s, 1H), 8.46 (s, 1H), 7.90 (s, 1H), 7.75 (d, J=8.8 Hz, 2H), 7.50 (s, 1H), 6.90 (d, J=8.8 Hz, 2H), 3.68-3.66 (m, 1H), 0.98-0.92 (m, 4H).

Step 2. 3-(4-(5-Chloro-2-((1-cyclopropyl-I//-pyrazol-4-yl)amino)pyrimidin-4-yl)phenoxy)-2,2-dimethylpropanenitrile (32)

Compound 32 (49.6 mg) was synthesized in 33% yield by utilizing a similar preparative procedure to the final step of Example 1 with compound 32a (120 mg, 0.37 mmol) and 2-cyano-2-methylpropyl methanesulfonate (131 mg, 0.74 mmol) as starting materials. LC-MS (Method 1): $t_R$=3.74 mm, m/z (M+H)⁺=409.2. ¾ NMR (400 MHz, DMSO-$d_6$) δ 9.72 (s, 1H), 8.50 (s, 1H), 7.90-7.84 (m, 3H), 7.50 (s, 1H), 7.16 (d, J=8.8 Hz, 2H), 4.11 (s, 2H), 3.69-3.65 (m, 1H), 1.44 (s, 6H), 1.01-0.90 (m, 4H).

Example 33

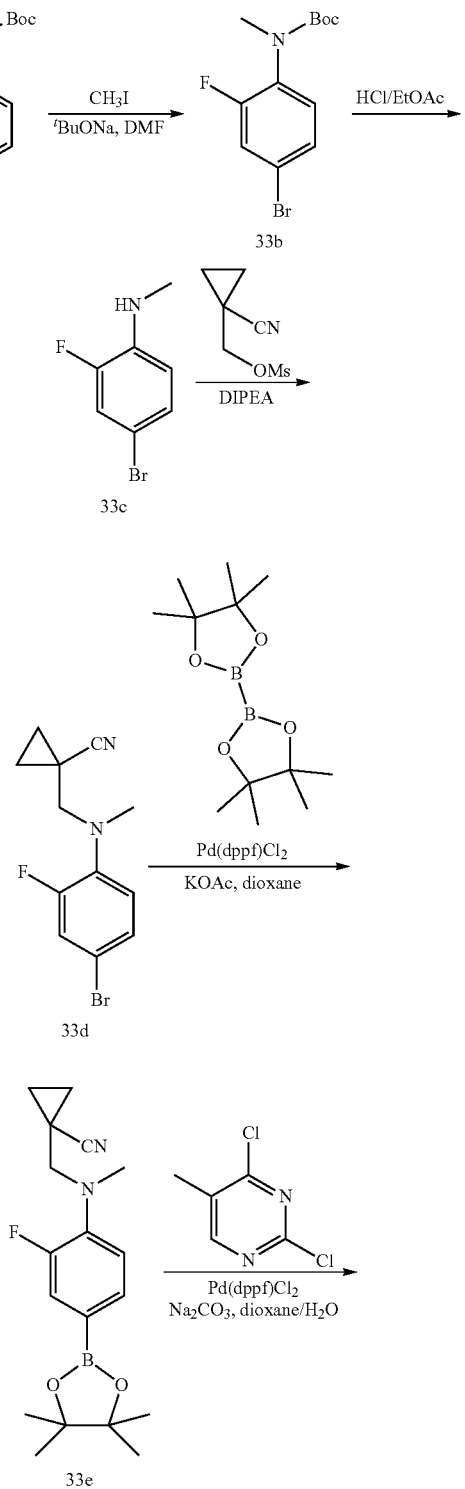

-continued

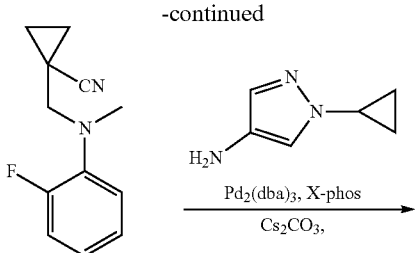

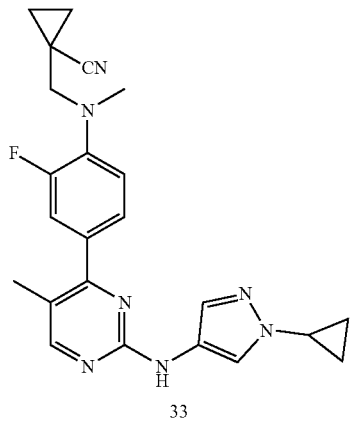

DIPEA (1.26 g, 9.80 mmol) in DMF (2 mL) was stirred at 130° C. for 48 hrs. After cooling down to RT, the mixture was diluted with EtOAc (20 mL) and washed with brine. The separated organic layer was concentrated. The residue was purified by FCC (eluent: PE: EtOAc=20:1) to give the product (740 mg, 53% yield) as green oil. ¾ NMR (400 MHz, CDCh) δ 7.19-7.14 (m, 2H), 6.89 (t, J=9.2 Hz, 1H), 3.28 (s, 2H), 3.00 (s, 3H), 1.27-1.24 (m, 2H), 0.90-0.87 (m, 2H). $^{19}F$ NMR (376 MHz, CDCh) 6-119.15.

Step 4. 1-(((2-fluoro-4-(4,4,5,5-tetramethyl-1,3,2-dioxaborolan-2-yl)phenyl)(methyl)amino)methyl)cyclopropanecarbonitrile (33e)

A mixture of 33d (200 mg, 0.709 mmol), 4,4,4',4',5,5,5',5'-octamethyl-2,2'-bi(1,3,2-dioxaborolane) (270 mg, 1.064 mmol), Pd(dppf)Ch (104 mg, 0.142 mmol) and KOAc (139 mg, 1.418 mmol) in 1,4-dioxane (3 mL) was stirred at 100° C. under N2 overnight. After cooling down to RT, the mixture was concentrated and purified by FCC (eluent: PE: EtOAc=2:1) to give the product (229 mg, 98% yield) as a white solid. LC-MS (Method 3): $t_R$=1.75 min, m/z $(M+H)^+$=331.2.

Step 5. 1-(((4-(2-Chloro-5-methylpyrimidin-4-yl)-2-fluorophenyl)(methyl)amino)methyl)cyclopropanecarbonitrile (33f)

A mixture of 33e (206 mg, 0.624 mmol), 2,4-dichloro-5-methylpyrimidine (102 mg, 0.624 mmol), Pd(dppf)Ch (91 mg, 0.125 mmol) and Na₂CO₃ (132 mg, 1.248 mmol) in 1,4-dioxane/H₂O (4 mL/1 mL) was stirred at 90° C. under N2 for 5 hrs. After cooling down to RT, the mixture was concentrated and purified by FCC (eluent: PE: EtOAc=2:1) to give the product (125 mg, 61% yield) as light yellow oil. LC-MS (Method 3): $t_R$=1.60 min, m/z $(M+H)^+$=331.1.

Step 6. 1-(((4-(2-((1-Cyclopropyl-1/T-pyrazol-4-yl)amino)-5-methylpyrimidin-4-yl)-2-fluorophenyl)(methyl)amino)methyl)cyclopropanecarbonitrile 33

A mixture of 33f (125 mg, 0.379 mmol), 1-cyclopropyl-liT-pyrazol-4-amine (51 mg, 0.417 mmol), Pd₂(dba)₃ (35 mg, 0.0379 mmol), X-phos (36 mg, 0.0758 mmol) and CS2CO3 (247 mg, 0.758 mmol) in 1,4-dioxane (3 mL) was stirred at 100° C. under N2 for 4 hrs. After cooling down to RT, the mixture was concentrated and purified by FCC (eluent: DCM: MeOH=30:1) to give the crude product. The crude product was purified by prep-HPLC (Method A) to give the product (53.8 mg, 34% yield) as a yellow solid. LC-MS (Method 1): $t_R$=3.49 min, m/z $(M+H)^+$=418.2. M NMR (400 MHz, DMSO-$d_6$) δ 9.29 (s, 1H), 8.30 (s, 1H), 7.90 (s, 1H), 7.53-7.48 (m, 3H), 7.15 (t, J=8.8 Hz, 1H), 3.67-3.63 (m, 1H), 3.37 (s, 2H), 3.00 (s, 3H), 2.24 (s, 3H), 1.29-1.26 (m, 2H), 1.05-1.00 (m, 2H), 0.99-0.96 (m, 2H), 0.95-0.91 (m, 2H). $^{19}F$ NMR (376 MHz, DMSO-$d_6$) δ-122.12.

Example 34

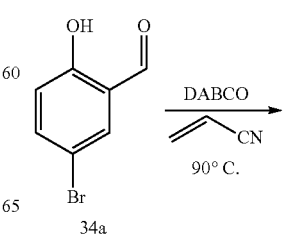

Step 1. Tert-butyl (4-bromo-2-fluorophenyl)(methyl)carbamate (33b)

A mixture of 33a (5.0 g, 17.24 mmol) and t-BuONa (2.15 g, 22.41 mmol) in DMF (6 mL) was stirred at 0° C. for 10 min. CH₃I (2.94 g, 20.69 mmol) was added dropwise to the reaction mixture. The mixture was stirred at 100° C. for 2 hrs. Another t-BuONa (496 mg, 5.17 mmol) and CH₃I (489 mg, 3.45 mmol) were added. The mixture was stirred at RT for another 2 hrs. The mixture was diluted with H2O (30 mL), extracted with EtOAc (50 mL*3). The separated organic layers were washed with brine and concentrated to give the crude product (5.22 g, 99% yield) as brown oil. 1H NMR (400 MHz, CDCl3) δ 7.28-7.24 (m, 2H), 7.12-7.08 (m, 1H), 3.17 (s, 3H), 1.40 (s, 9H). 19F NMR (376 MHz, CDCl3) δ-117.58.

Step 2. 4-Bromo-2-fluoro-7V-methylaniline (33c)

A solution of 33b (5.22 g, 17.17 mmol) in a solution of HCl(g) in EtOAc (35 mL, 2 M) was stirred at RT for 2 hrs. The mixture was concentrated. The residue was diluted with N¾(g) in MeOH (3 M, 15 mL). The mixture was stirred at RT for 10 mins and concentrated. The residue was diluted with DCM (20 mL) and filtered. The fdtrate was concentrated to give the crude product (3.37 g, 96% yield) as a brown solid. ¾ NMR (400 MHz, CDCl₃) δ 7.13-7.08 (m, 2H), 6.53 (t, J=8.0 Hz, 1H), 3.92 (s, 1H), 2.85 (s, 3H). $^{19}F$ NMR (376 MHz, CDCh) 6-134.45.

Step 3. 1-(((4-Bromo-2-fluorophenyl)(methyl)amino)methyl)cyclopropanecarbonitrile (33d)

A mixture of 33c (1.0 g, 4.90 mmol), (1-cyanocyclopropyl)methyl methanesulfonate (1.29 g, 7.35 mmol) and

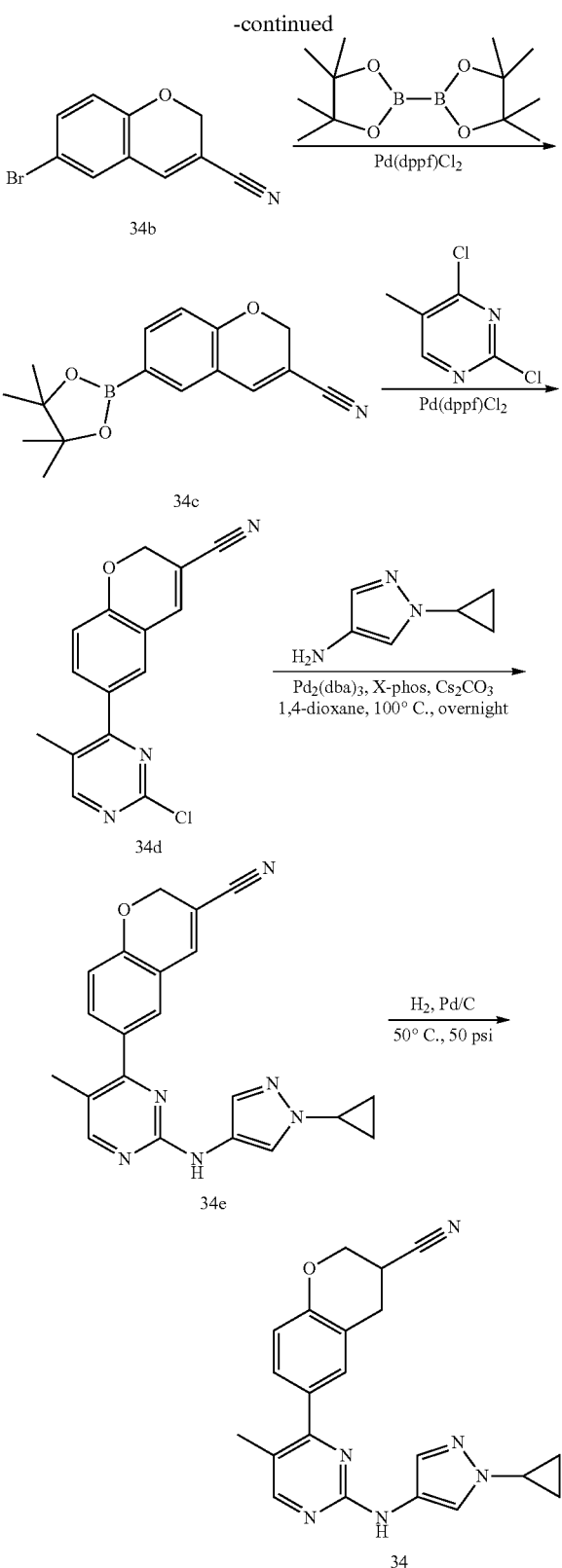

Step 1. 6-Bromo-2/l-chromene-3-carbonitrile (34b)

A mixture of 34a (5.0 g, 24.87 mmol), acrylonitrile (1.32 g, 24.87 mmol) and DABCO (1.09 g, 4.97 mmol) was stirred at 90° C. for 6 hrs. After cooling down to RT., the mixture was diluted with H2O (50 mL), extracted with DCM (50 mL*3). The combined organic layers were washed with brine (50 mL) and concentrated. The residue was purified by FCC (eluent: PE: EtOAc=30:1) to give the product as a yellow solid (1.25 g, 21% yield). $^3$M NMR (400 MHz, DMSO-$d_6$) δ 7.54 (s, 1H), 7.51 (d, J=2.4 Hz, 1H), 7.46 (dd, J=2.4, 8.4 Hz, 1H), 6.87 (d, J=8.8 Hz, 1H), 4.92 (d, J=1.6 Hz, 2H).

Step 2. 6-(4,4,5,5-Tetramethyl-1,3,2-dioxaborolan-2-yl)-2/T-chromene-3-carbonitrile (34c)

A mixture of 34b (940 mg, 3.98 mmol), 4,4,4',4',5,5,5',5'-octamethyl-2,2'-bi(1,3,2-dioxaborolane) (1.52 g, 5.97 mmol), KOAc (781 mg, 7.96 mmol) and Pd(dppf)Cl2 (582 mg, 0.796 mmol) in 1,4-dioxane (19 mL) was stirred at 100° C. under N2 for 5 hrs. The mixture was concentrated and the residue was purified by FCC (eluent: PE: EtOAc=30:1) to give the product (890 mg, 79% yield) as a white solid. $^3$M NMR (400 MHz, DMSO-$d_6$) δ 7.63 (s, 1H), 7.59-7.57 (m, 2H), 6.88 (d, J=8.8 Hz, 1H), 4.92 (d, J=1.6 Hz, 2H), 1.29 (d, J=5.2 Hz, 12H).

Step 3. 6-(2-Chloro-5-methylpyrimidin-4-yl)-2/T-chromene-3-carbonitrile (34d)

A mixture of 34c (890 mg, 3.14 mmol), 2,4-dichloro-5-methylpyrimidine (538 mg, 3.30 mmol), Na2CC>3 (666 mg, 6.28 mmol) and Pd(dppf)Cl2 (230 mg, 0.314 mmol) in 1,4-dioxane/H$_2$O (18 mL/4.5 mL) was stirred at 100° C. under N2 for 3 hrs. After cooling down to RT., the mixture was concentrated, purified by FCC (eluent: PE: EtOAc=4:1) to give the product (475 mg, 53% yield) as a yellow solid. LC-MS (Method 3): $t_R$=1.56 min, m/z (M+H)$^+$=284.0

Step 4. 6-(2-((1-Cyclopropyl-1//-pyrazol-4-yl)amino)-5-methylpyrimidin-4-yl)-2//-chromene-3-carbonitrile (34e)

A mixture of 34d (475 mg, 1.674 mmol), 1-cyclopropyl-1//-pyrazol-4-amine (206 mg, 1.674 mmol), Pd$_2$(dba) 3 (153 mg, 0.1674 mmol), X-phos (159 mg, 0.3348 mmol) and CS$_2$CO$_3$ (1.09 mg, 3.348 mmol), in 1,4-dioxane (10 mL) was stirred at 100° C. under N$_2$ overnight. After cooling down to RT., the mixture was concentrated and the residue was purified by FCC (eluent: PE: EtOAc=2:1) to give the product (330 mg, 53% yield) as a white solid. LC-MS (Method 1): $t_R$=2.66 mi, m/z (M+H)$^+$=371.1

Step 5. 6-(2-((1-Cyclopropyl-1//-pyrazol-4-yl)amino)-5-methylpyrimidin-4-yl)chroman-3-carbonitrile (34)

To a mixture of 34e (50 mg, 0.135 mmol) in EtOAc (10 mL) was added Pd/C (40 mg, 10% Pd/C wetted with ca. 55% water). The mixture was stirred under ¾ (50 Psi) at 50° C. for 48 hrs. The mixture was filtered. The filtrate was concentrated to give a crude product. The crude was purified by the prep-HPLC (method A) to give the product (16.0 mg, 32% yield) as a white solid. LC-MS (Method 1): $t_R$=2.91 min, m/z (M+H)$^+$=373.1. $^1$H NMR (400 MHz, DMSO-$d_6$) δ 9.29 (s, 1H), 8.30 (s, 1H), 7.92 (s, 1H), 7.54-7.51 (m, 2H), 7.45 (s, 1H), 6.96 (d, J=8.4 Hz, 1H), 4.45-4.41 (m, 1H), 4.31-4.28 (m, 1H), 3.66-3.62 (m, 2H), 3.28-3.24 (m, 1H), 3.12-3.07 (m, 1H), 2.22 (s, 3H), 1.00-0.90 (m, 4H).

Example 35
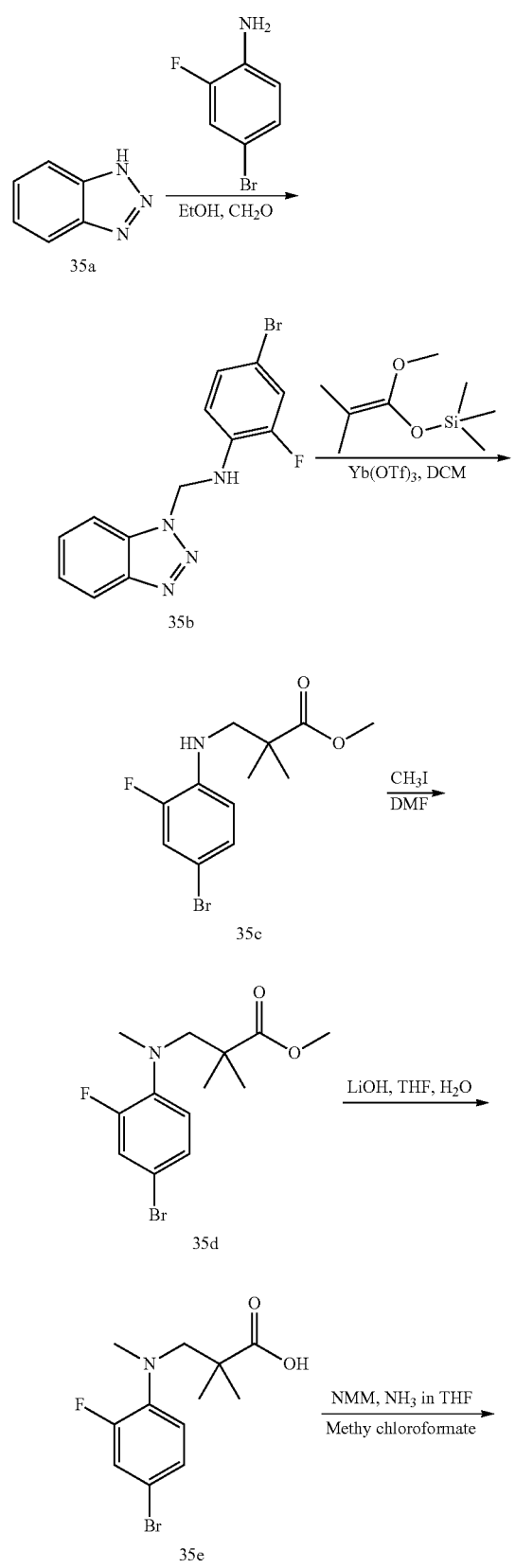
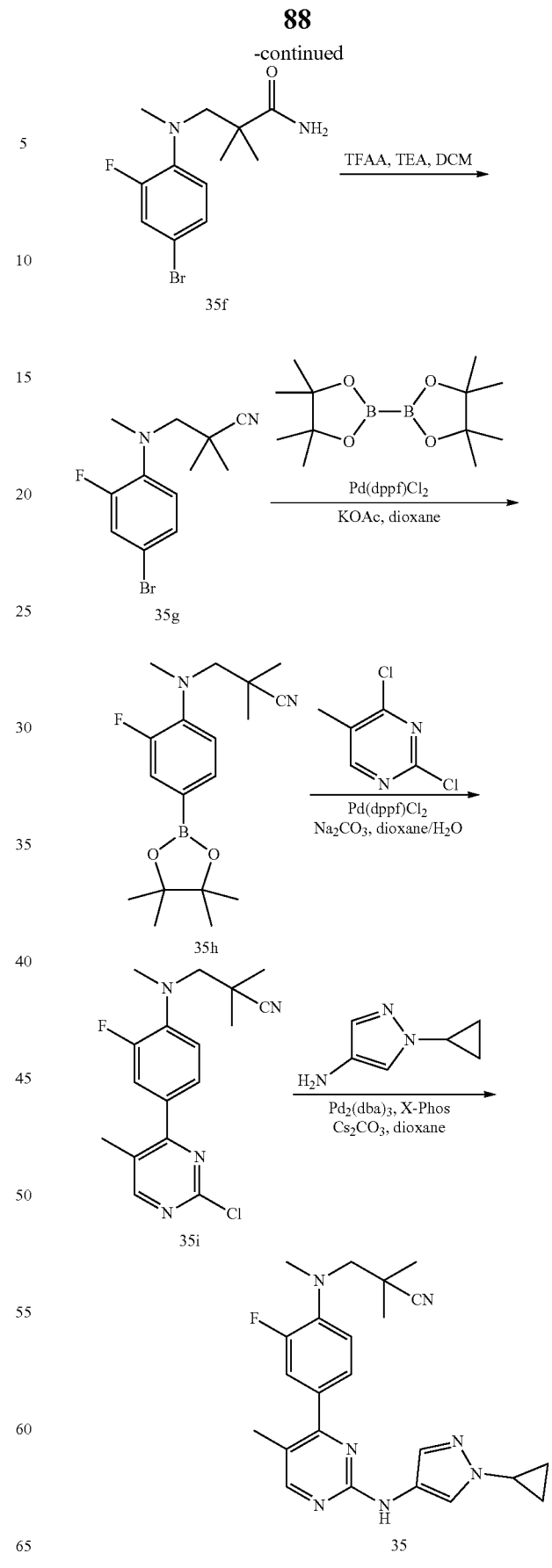

Step 1. 7V-((1/T-benzo[i/][1,2,3]triazol-1-yl) methyl)-4-bromo-2-fluoroaniline (35b)

To a solution of 35a (2.2 g, 18.4 mmol) and 4-bromo-2-fluoroaniline (2.5 g, 13.2 mmol) in EtOH (40 mL) and water (8 mL) was added formaldehyde (8 mL, 37% wt in water) dropwise. The mixture was stirred at RT for 30 minutes. The mixture was filtered. The filter cake was washed with EtOH and dried to give the crude product (3.2 g, 73% yield) as a white solid. $^1$H NMR (400 MHz, CDCh) δ 8.06 (d, J=8.4 Hz, 1H), 7.63 (d, J=8.0 Hz, 1H), 7.51 (t, J=7.6 Hz, 1H), 7.38 (t, J=7.6 Hz, 1H), 7.13-7.09 (m, 2H), 7.04 (t, J=8.4 Hz, 1H), 6.10 (d, J=6.8 Hz, 2H), 5.17 (br s, 1H).

Step 2. Methyl 3-((4-bromo-2-fluorophenyl)amino)-2,2-dimethylpropanoate (35c)

To a solution of 35b (900 mg, 2.80 mmol) and Yb(OTf)3 (348 mg, 5.61 mmol) in DCM (10 mL) was added a solution of ((1-methoxy-2-methylprop-1-en-1-yl)oxy)trimethylsilane (731 mg, 4.21 mmol) in DCM (2 mL). The mixture was stirred at 0° C. to RT overnight. The mixture was concentrated. The residue was purified by FCC (eluent: PE:EtOAc=40:1) to give the product (470 mg, 55% yield) as colorless oil. ¾ NMR (400 MHz, CDCb) δ 7.11-7.06 (m, 2H), 6.58 (t, J=4.8 Hz, 1H), 4.22 (br s, 1H), 3.68 (s, 3H), 3.23 (d, J=6.4 Hz, 2H), 1.26 (s, 6H).

Step 3. Methyl 3-((4-bromo-2-fluorophenyl) (methyl)amino)-2,2-dimethylpropanoate (35d)

To a solution of 35c (1.0 g, 3.28 mmol) in DMF (7 mL) was added NaH (328 mg, 8.20 mmol, 60% in mineral oil) in batches at 0° C. After stirring for 40 minutes, iodomethane 700 mg, 4.92 mmol) in DMF (1 mL) was added dropwise at 0° C. The mixture was stirred at RT. for 3 hrs. The mixture was diluted with H2O (20 mL), extracted with EtOAc (20 mL*3). The combined organic layers were washed with brine (20 mL), dried over Na$_2$SC>$_4$, filtered and the filtrate was concentrated to give a crude product (1.1 g, 100% yield) as a yellow solid. LC-MS (Method 3): $t_R$=1.83 min, m/z (M+H)$^+$=320.0.

Step 4. 3-((4-Bromo-2-fluorophenyl)(methyl) amino)-2,2-dimethylpropanoic acid (35e)

To a mixture of 35d (1.1 g, 3.46 mmol) in MeOH/THF/H$_2$O (8 mL/4 mL/4 mL) was added LiOHH$_2$O (726 mg, 17.29 mmol). The mixture was stirred at 50° C. for 4 hours. After cooling to RT, the mixture was adjusted to pH 3~4 by 2N aq. HCl. The mixture was extracted with DCM (30 mL*3). The combined organic layers were concentrated to give a crude product (1.03 g, 100% yield) as a yellow solid, which was used for next step directly. LC-MS (Method 3): $t_R$-1.58 mm, m/z (M+H)$^+$=306.1.

Step 5. 3-((4-Bromo-2-fluorophenyl)(methyl) amino)-2,2-dimethylpropanamide (35f)

To a solution of 35e (1.03 g, 3.39 mmol) in THF (10 mL) was added NMM (1.03 g, 10.66 mmol) and methy chloroformate (644 mg, 6.78 mmol) at 0° C. The mixture was stirred at 0° C. for 1 hour. The solid was filtered and the filtrate was dropwise added a solution of NH$_3$(g) in THF (3 M, 5 mL). The resultant mixture was stirred at 0° C. to RT for 2 hours and concentrated to give a crude product (1.1 g, 100% yield) as yellow oil. LC-MS (Method 3): $t_R$=1.55 min, m/z (M+H)$^+$=305.0.

Step 6. 3-((4-Bromo-2-fluorophenyl)(methyl) amino)-2,2-dimethylpropanenitrile (35 g)

To a mixture of 35f (1.1 g, 3.46 mmol) and TEA (1.1 g, 10.89 mmol) in DCM (10 mL) was added TFAA (1.14 g, 5.45 mmol) at 0° C. for 2 hours. The mixture was diluted with water (20 mL), and extracted with DCM (30 mL*2). The combined organic layers were washed with brine (20 mL) and concentrated. The residue was purified by FCC (PE: EtOAc=20:1) to give the product (540 mg, 52% yield) as yellow oil. LC-MS (Method 3): $t_R$=1.88 min, m/z (M+H)+287.0.

Step 7. 3-((2-Fluoro-4-(4,4,5,5-tetramethyl-1,3,2-dioxaborolan-2-yl)phenyl)(methyl)amino)-2,2-dimethylpropanenitrile (35h)

Compound 35h (280 mg) was synthesized in 80% yield by utilizing a similar preparative procedure to the second step of Example 25 with 35 g (300 mg, 1.056 mmol) and 4,4,4',4',5,5,5',5'-octamethyl-2,2'-bi(1,3,2-dioxaborolane) (402 mg, 1.585 mmol) as starting materials. LC-MS (Method 3): $t_R$=1.98 min, m/z (M+H)$^+$=333.2.

Step 8. 3-((4-(2-Chloro-5-methylpyrimidin-4-yl)-2-fluorophenyl)(methyl)amino)-2,2-dimethylpropanenitrile (35i)

Compound 35i (60 mg) was synthesized in 43% yield by utilizing a similar preparative procedure to the third step of Example 25 with 35h (140 mg, 0.422 mmol) and 2,4-dichloro-5-methylpyrimidine (69 mg, 0.422 mmol) as starting materials. LC-MS (Method 3): $t_R$=1.87 min, m/z (M+H)$^+$=333.1.

Step 9. 3-((4-(2-((1-Cyclopropyl-/T-pyrazol-4-yl) amino)-5-methylpyrimidin-4-yl)-2-fluorophenyl) (methyl)amino)-2,2-dimethylpropanenitrile (35)

Compound 35 (13.7 mg) was synthesized in 18% yield by utilizing a similar preparative procedure to the final step of Example 25 with 35i (60 mg, 0.181 mmol) and 1-cyclopropyl-1H-pyrazol-4-amine (24 mg, 0.199 mmol) as starting materials. LC-MS (Method 1): $t_R$=4.22 min, m/z (M+H)$^+$= 420.2. ¾ NMR (400 MHz, DMSO-d$_6$) δ 9.27 (s, 1H), 8.29 (s, 1H), 7.89 (s, 1H), 7.51-7.47 (m, 3H), 7.22 (t, J=9.2 Hz, 1H), 3.67-3.62 (m, 1H), 3.58 (s, 2H), 3.13 (s, 3H), 2.24 (s, 3H), 1.31 (s, 6H), 1.00-0.98 (m, 2H), 0.97-0.89 (m, 2H). $^{19}$F NMR (376 MHz, DMSO-d$_6$) δ-121.84.

Example 36

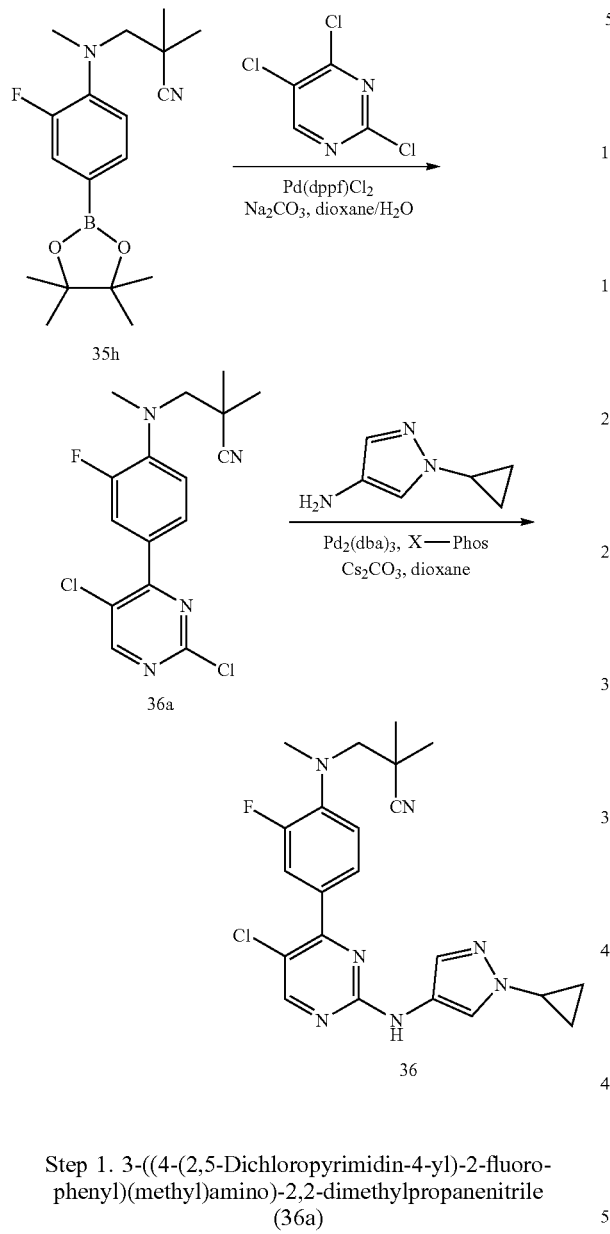

Step 1. 3-((4-(2,5-Dichloropyrimidin-4-yl)-2-fluorophenyl)(methyl)amino)-2,2-dimethylpropanenitrile (36a)

Compound 36a (270 mg) was synthesized in 85% yield by utilizing a similar preparative procedure to the third step of Example 25 with 35h (300 mg, 0.904 mmol) and 2,4,5-trichloropyrimidine (182 mg, 0.994 mmol) as starting materials. LC-MS (Method 3): $t_R$=1.78 min, m/z (M+H)$^+$=353.0.

Step 2. 3-((4-(5-Chloro-2-((1-cyclopropyl-Li7-pyrazol-4-yl)amino)pyrimidin-4-yl)-2-fluorophenyl)(methyl)amino)-2,2-dimethylpropanenitrile (36)

Compound 36 (19.9 mg) was synthesized in 6% yield by utilizing a similar preparative procedure to the final step of Example 25 with 36a (270 mg, 0.767 mmol) and 1-cyclopropyl-\H-pyrazol-4-amine (104 mg, 0.844 mmol) as starting materials. LC-MS (Method 1): $t_R$=3.76 min, m/z (M+H)$^+$=440.1. ¾ NMR (400 MHz, DMSO-d$_6$) δ 9.69 (s, 1H), 8.48 (s, 1H), 7.89 (s, 1H), 7.70-7.63 (m, 2H), 7.51 (s, 1H), 7.23 (t, J=9.2 Hz, 1H), 3.69-3.66 (m, 1H), 3.63 (s, 2H), 3.15 (s, 3H), 1.31 (s, 6H), 1.01-0.96 (m, 2H), 0.95-0.90 (m, 2H). $^{19}$F NMR (376 MHz, DMSO-d$_6$) δ-121.77.

Example 37

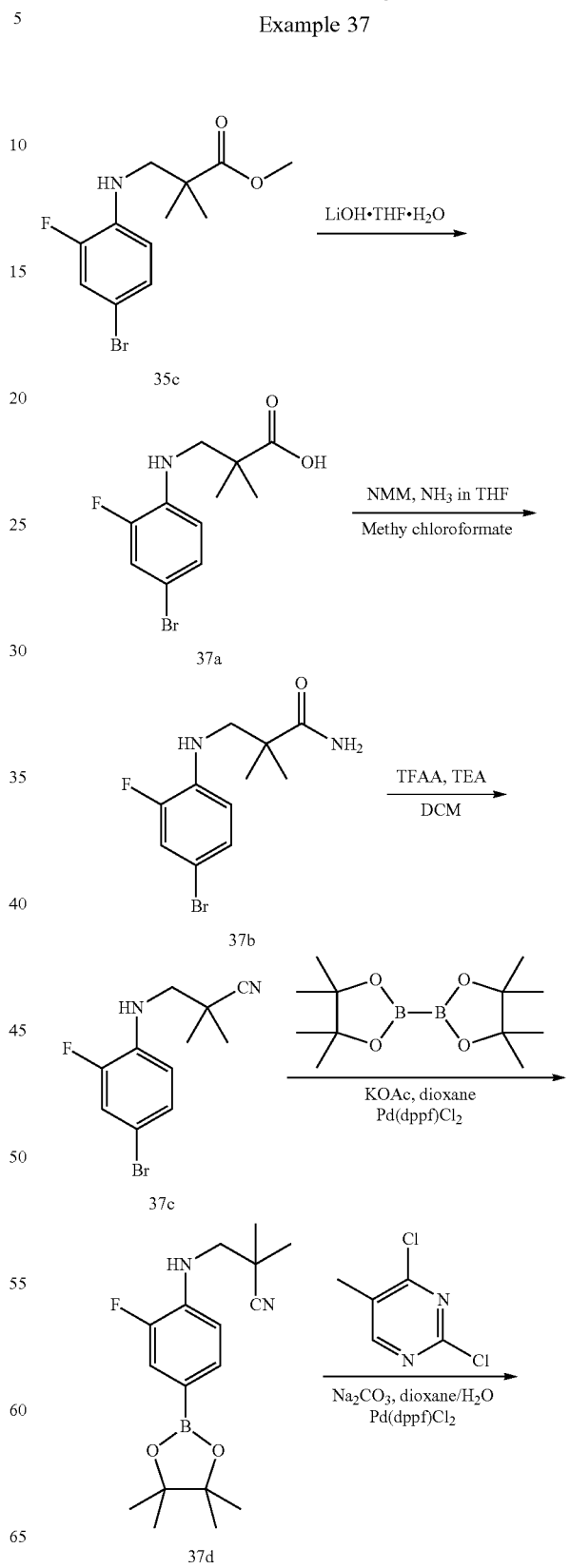

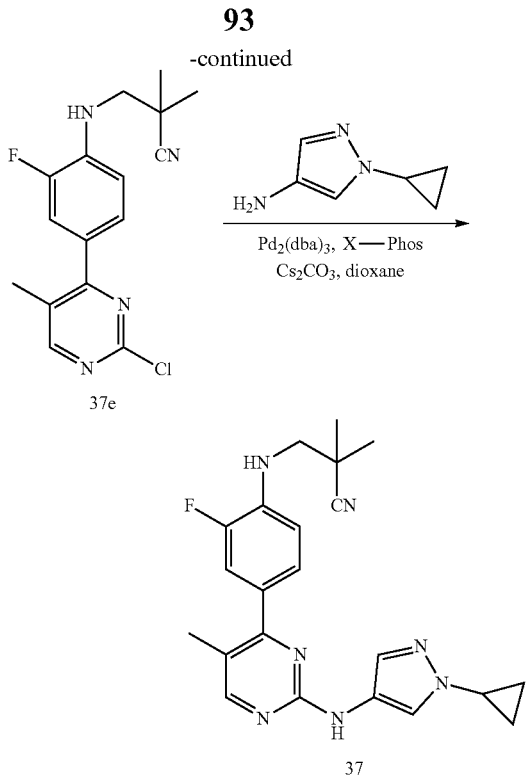

37

Step 1. 3-((4-Bromo-2-fluorophenyl)amino)-2,2-dimethylpropanoic acid (37a)

To a solution of 35c (470 mg, 1.56 mmol) in THF (2 mL) and MeOH (2 mL) was added aq. LiOH·H$_2$O (197 mg, 4.69 mmol in 1 mL of water). The mixture was stirred at 30° C. for 2 hrs. The mixture was diluted with water (50 mL) and extracted with EtOAc (50 mL*2). The separated aqueous layer was adjusted to pH 4~5 by 1N aq. HCl and extracted with EtOAc (50 mL). The separated organic layer was dried over Na2SO4' filtered and concentrated to give the crude product (430 mg, 96% yield) as yellow oil. ¾ NMR (400 MHz, DMSO-d$_6$) δ 12.38 (br s, 1H), 7.27 (dd, J=11.6, 2.4 Hz, 1H), 7.11 (d, J=8.4 Hz, 1H), 6.81 (t, J=9.2 Hz, 1H), 5.20 (br s, 1H), 3.22 (d, J=6.0 Hz, 2H), 1.13 (s, 6H).

Step 2. 3-((4-Bromo-2-fluorophenyl)amino)-2,2-dimethylpropanamide (37b)

To a solution of 37a (430 mg, 1.48 mmol) in THF (5 mL) was added NMM (450 mg, 4.45 mmol) followed by methyl chloroformate (282 mg, 2.97 mmol) at 0° C. The mixture was stirred at 0° C. to RT for 1 hour. The mixture was filtered. Then a solution of N¾(g) in THF (5 mL, 4M) was added to the filtrate. The mixture was stirred at 0° C. to RT overnight. The mixture was diluted with water (50 mL) and extracted with EtOAc (50 mL*2). The combined organic phases were dried over Na$_2$SO4, filtered and concentrated to give the crude product (400 mg, 93% yield) as yellow oil. ¾ NMR (400 MHz, DMSO-d$_6$) δ 7.26 (dd, J=11.6, 2.4 Hz, 1H), 7.19 (s, 1H), 7.11 (dd, J=8.8, 2.0 Hz, 1H), 6.94 (s, 1H), 6.80 (t, J=9.2 Hz, 1H), 5.17-5.14 (m, 1H), 3.12 (d, J=6.0 Hz, 2H), 1.12 (s, 6H).

Step 3. 3-((4-Bromo-2-fluorophenyl)amino)-2,2-dimethylpropanenitrile (37c)

To a solution of 37b (350 mg, 1.21 mmol) and TEA (367 mg, 3.63 mmol) in DCM (5 mL) was added TFAA (381 mg, 1.82 mmol) at 0° C. The mixture was stirred at 0° C. to 25° C. for 30 minutes. The mixture was diluted with sat. NaHCCb (50 mL), extracted with EtOAc (50 mL*2). The combined organic phases were dried over Na$_2$SO$_4$, fdtered and concentrated to give the crude product (274 mg, 84% yield) as yellow oil. ¾ NMR (400 MHz, DMSO-d$_6$) δ 7.29 (dd, J=11.6, 2.4 Hz, 1H), 7.12 (dd, J=8.4, 1.6 Hz, 1H), 6.96 (t, J=9.2 Hz, 1H), 5.95-5.92 (m, 1H), 3.31 (s, 2H), 1.31 (s, 6H).

Step 4. 3-((2-Fluoro-4-(4,4,5,5-tetramethyl-1,3,2-dioxaborolan-2-yl)phenyl)amino)-2,2-dimethylpropanenitrile (37d)

Compound 37d (300 mg, crude) was synthesized in 93% yield by utilizing a similar preparative procedure to the second step of Example 25 with 37c (274 mg, 1.01 mmol) and 4,4,4',4',5,5,5',5'-octamethyl-2,2'-bi(1,3,2-dioxaborolane) (258 mg, 1.01 mmol) as starting materials. LC-MS (Method 3): t$_{3/4}$=1.88 min, m/z (M+H)$^+$=319.2.

Step 5. 3-((4-(2-Chloro-5-methylpyrimidin-4-yl)-2-fluorophenyl)amino)-2,2-dimethylpropanenitrile (37e)

Compound 37e (170 mg crude) was synthesized in 57% yield by utilizing a similar preparative procedure to the third step of Example 25 with 37d (300 mg, 0.94 mmol) and 2,4-dichloro-5-methylpyrimidine (231 mg, 1.42 mmol) as starting materials. LC-MS (Method 3): t¾=1.74 mm, m/z (M+H)$^+$=319.1.

Step 8. 3-((4-(2-((1-Cyclopropyl-1/T-pyrazol-4-yl)amino)-5-methylpyrimidin-4-yl)-2-fluorophenyl)amino)-2,2-dimethylpropanenitrile (37)

Compound 37 (14.8 mg, crude) was synthesized in 17% yield by utilizing a similar preparative procedure to the final step of Example 25 with 37e (69 mg, 0.22 mmol) and 1-cyclopropyl-1//-pyrazol-4-amine (40 mg, 0.33 mmol) as starting materials. LC-MS (Method 1): t$_R$=3.66 mm, m/z (M+H)$^+$=406.2. ¾ NMR (400 MHz, DMSO-d$_6$) δ 9.22 (s, 1H), 8.25 (s, 1H), 7.90 (s, 1H), 7.50-7.42 (m, 3H), 7.11 (t, J=9.2 Hz, 1H), 6.19 (t, J=4.8 Hz, 1H), 3.67-3.62 (m, 1H), 3.42 (d, J=6.8 Hz, 2H), 2.25 (s, 3H), 1.36 (s, 6H), 1.00-0.89 (m, 4H).

Example 38

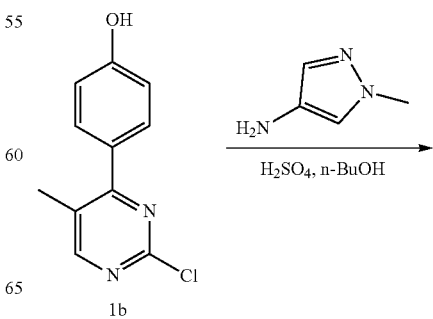

-continued

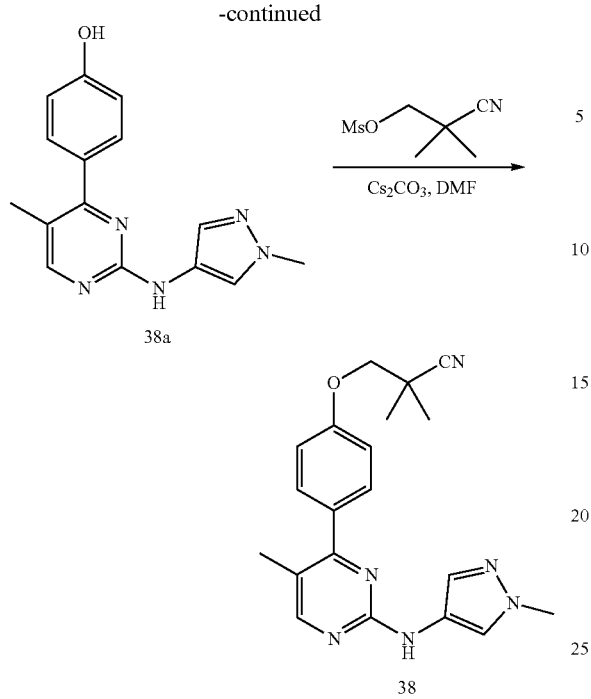

Step 1. 4-(5-Methyl-2-((1-methyl-V//-pyrazol-4-yl)amino)pyrimidin-4-yl)phenol (38a)

A mixture of 1 b (500 mg, 2.27 mmol), 1-methyl-1//-pyrazol-4-amine (264 mg, 2.72 mmol) and cone. H2SO4 (1 drop) in n-BuOH (3 mL) was stirred at 120° C. for 2 hours. The reaction mixture was concentrated and purified by silica gel column (DCM: MeOH=20:1) to give the product (348 mg, 55% yield) as a brown solid. ¾ NMR (400 MHz, DMSO-$d_6$) δ 9.81 (s, 1H), 9.22 (s, 1H), 8.26 (s, 1H), 7.83 (s, 1H), 7.56 (d, J=8.4 Hz, 2H), 7.48 (s, 1H), 6.88 (d, J=8.8 Hz, 2H), 3.78 (s, 3H), 2.20 (s, 3H).

Step 2. 2,2-Dimethyl-3-(4-(5-methyl-2-((1-methyl-1//-pyrazol-4-yl)amino)pyrimidin-4-yl)phenoxy)propanenitrile (38)

Compound 38 (26.7 mg) was synthesized in 26% yield by utilizing a similar preparative procedure to the final step of Example 1 with 38a (80 mg, 0.28 mmol) and 2-cyano-2-methylpropyl methanesulfonate (74 mg, 0.42 mmol) as starting materials. LC-MS (Method 1): $t_R$=3.66 min, m/z (M+H)$^+$=363.2. ¾ NMR (400 MHz, DMSO-$d_6$) δ 9.29 (s, 1H), 8.29 (s, 1H), 7.83 (s, 1H), 7.68 (d, J=8.8 Hz, 2H), 7.48 (s, 1H), 7.12 (d, J=8.4 Hz, 2H), 4.09 (s, 2H), 3.78 (s, 3H), 2.21 (s, 3H), 1.44 (s, 6H).

Example 39

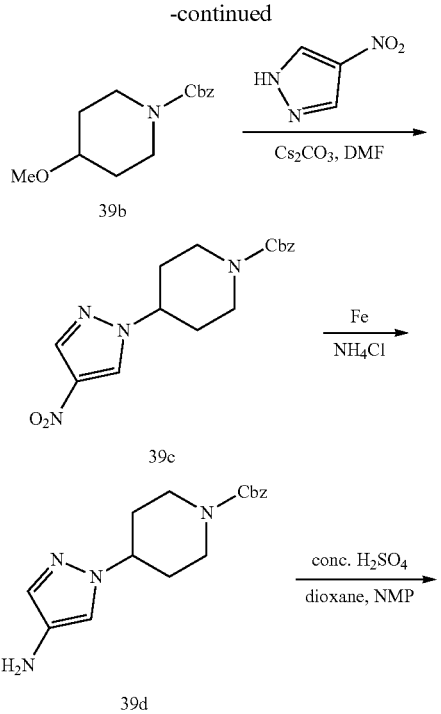

Step 1. Benzyl 4-((methylsulfonyl)oxy)piperidine-1-carboxylate (39b)

To a mixture of benzyl 4-hydroxypiperidine-1-carboxylate (10.0 g, 42.50 mmol) and TEA (8.6 g, 85.15 mmol) in DCM (120 mL) was added MsCl (5.4 g, 47.16 mmol) at RT. After stirring at RT for 18 hrs, the reaction mixture was diluted with H2O (50 mL) and extracted with DCM (40 mL*3). The combined organic layers were concentrated to afford the crude product (13.2 g, 99%) as brown oil. $^1$HNMR (400 MHz, CDCl$_3$) δ 7.38-7.30 (m, 5H), 5.13 (s, 2H), 4.93-4.87 (m, 1H), 3.78-3.72 (m, 2H), 3.45-3.39 (m, 2H), 3.30 (s, 3H), 1.97-1.96 (m, 2H), 1.88-1.82 (m, 2H).

Step 2. Benzyl 4-(4-nitro-1/T-pyrazol-1-yl)piperidine-1-carboxylate (39c)

To a mixture of 39b (13.5 g, 43.13 mmol) and 4-nitrolif-pyrazole (4.14 g, 36.64 mmol) in DMF (150 mL) was added CS$_2$CO$_3$ (14.06 g, 43.13 mmol). The reaction was stirred for 20 hrs at 120° C. After cooling to RT, the reaction mixture was filtered and the filtrate was diluted with H$_2$O (80 mL). The mixture was extracted with EtOAc (80 mL*2) and the combined organic layers were concentrated to dryness. The residue was purified by column chromatography on silica gel (PE: EtOAc=1:1) to afford the product (7.11 g, 58%) as yellow oil. ¾ NMR (400 MHz, CDCl$_3$) δ 8.14 (s, 1H), 8.08 (s, 1H), 7.40-7.32 (m, 5H), 5.15-5.12 (m 2H), 4.35-4.28 (m, 3H), 2.98-2.95 (m, 2H), 2.20-2.17 (m, 2H), 1.94-1.92 (m, 2H).

Step 3. Benzyl 4-(4-amino-1//-pyrazol-1-yl)piperidine-1-carboxylate (39d)

Compound 39c (7.11 g, 21.55 mmol) was dissolved in EtOH (120 mL). NH$_4$Cl (5.76 g, 107.66 mmol) was dissolved in H2O (25 mL). The above two solutions were mixed together and warmed to 60° C. Fe powder (4.22 g, 75.36 mmol) was added to the mixture. The mixture was stirred at 80° C. for 3 hrs. After cooling to RT, the reaction mixture was filtered and the fdtrate was concentrated. The residue was diluted with H2O (60 mL) and extracted with EtOAc (60 mL*3). The combined organic layers were concentrated to dryness to give the crude product (6.4 g, 98%) as purple oil. LC-MS (Method 3): t¾=1.25 min, m/z (M+H)$^+$=301.1.

Step 4. Benzyl 4-(4-((4-(3-fluoro-4-hydroxyphenyl)-5-methylpyrimidin-2-yl)amino)-1/T-pyrazol-1-yl)piperidine-1-carboxylate (39e)

To a mixture of 39d (756 mg, 2.52 mmol) and 4a (500 mg, 2.10 mmol) in 1,4-dioxane (5 mL) and NMP (5 mL), was added conc. H2SO4 (5 drops). The mixture was stirred at 120° C. for 16 hrs. After cooling to RT, the reaction mixture was diluted with H2O (40 mL) and extracted with EtOAc (30 mL*3). The combined organic layers were concentrated and the residue was purified by column chromatography on silica gel (DCM: MeOH=30:1) to afford the product (0.8 g, 76%) as green solid. LC-MS (Method 3): t$_R$=1.61 min, m/z (M+H)$^+$=503.2.

Step 5. Benzyl 4-(4-((4-(4-(2-cyano-2-methylpropoxy)-3-fluorophenyl)-5-methylpyrimidin-2-yl)amino)-1//-pyrazol-1-yl)piperidine-1-carboxylate (39f)

Compound 39f (55 mg) was synthesized in 31% yield by utilizing a similar preparative procedure to the final step of Example 1 with 39e (150 mg, 0.30 mmol) and 2-cyano-2-methylpropyl methanesulfonate (79 mg, 0.45 mmol) as starting materials. LC-MS (Method 3): t$_R$=1.78 mm, m/z (M+H)$^+$=584.3.

Step 6. 3-(2-Fluoro-4-(5-methyl-2-((1-(piperidin-4-yl)-1/T-pyrazol-4-yl)amino)pyrimidin-4-yl)phenoxy)-2,2-dimethylpropanenitrile (39)

Compound 39f (55 mg, 0.09 mmol) was dissolved in MeOH (2 mL) followed by the addition of Pd/C (24 mg, 10% wt, wetted with ca. 55% water) and Pd(OH)$_2$/C (24 mg, 20% wt dihydroxypalladium on charcoal). The above mixture was stirred under ¾ (1 atm) at 40° C. for 6 hours. The mixture was filtered and the filtrate was concentrated. The residue was purified by IVep-HPLC (Method A) to give the title product (5.6 mg, 14% yield). LC-MS (Method 1): t$_R$=3.33 mm, m/z (M+H)$^+$=450.3. ¾NMR (400 MHz, CD3OD) δ 8.17 (s, 1H), 7.94 (s, 1H), 7.53 (s, 1H), 7.44 (dd, J=2.4, 12.0 Hz, 1H), 7.39 (d, J=8.4 Hz, 1H), 7.16 (t, J=8.4 Hz, 1H), 4.34-4.29 (m, 1H), 4.03 (s, 2H), 3.36 (d, J=13.2 Hz, 2H), 3.03-2.96 (m, 2H), 2.17-2.15 (m, 5H), 2.10-2.01 (m, 2H), 1.42 (s, 6H).

Example 40

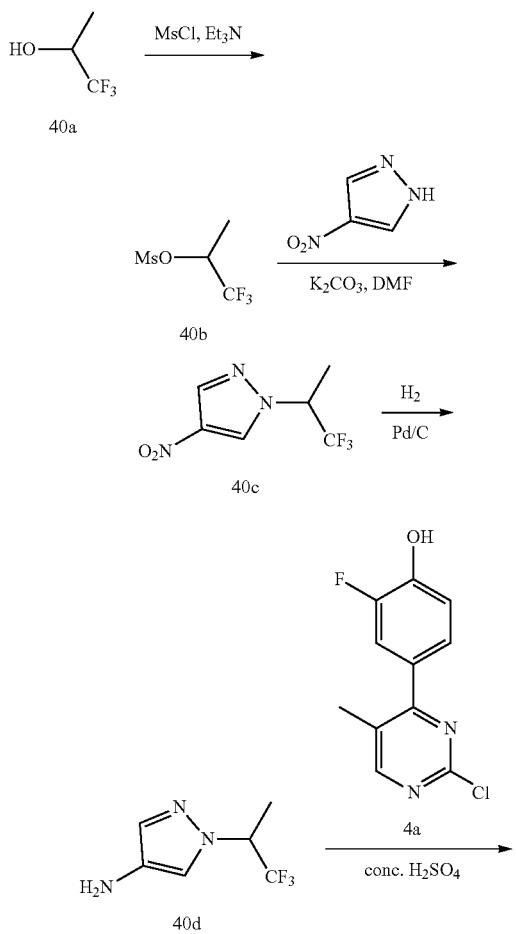

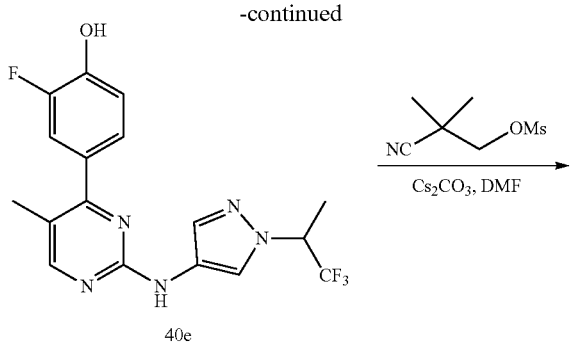

40e

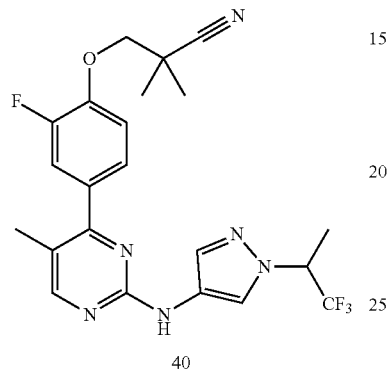

40

Step 1. 1,1,1-Trifluoropropan-2-yl methanesulfonate (40b)

To a mixture of 1,1,1-trifluoropropan-2-ol (5.0 g, 43.86 mmol) and TEA (8.86 g, 87.72 mmol) in DCM (100 mL) was added MsCl (5.5 g, 48.24 mmol) at 0° C. The mixture was warmed to RT and stirred for 2 hours. The mixture was diluted with DCM (300 mL), washed with H₂O (300 mL*3), dried over Na₂SO4 and filtered. The filtrate was concentrated to afford the title product (7.38 g, 88%) as yellow oil. $^1$HNMR (400 MHz, CDCb) δ 5.02-4.98 (m, 1H), 3.11 (s, 3H), 1.58 (d, J=6.4 Hz, 3H).

Step 2. 4-Nitro-1-(1,1,1-trifluoiOpiOpan-2-yl)-1//-pyrazole (40c)

To a mixture of 4-nitro-lif-pyrazole (3.62 g, 32.03 mmol) and 40b (7.38 g, 38.44 mmol) in DMF (100 mL) was added K2CO3 (8.84 g, 64.06 mmol). The mixture was stirred at 120° C. under N2 for 18 hours. The mixture was cooled down to RT and concentrated to dryness. The residue was purified by flash chromatography on silica gel (PE: EtOAc=8:1) to afford the title product (3.1 g, crude, 46%) as yellow oil. $^1$HNMR(400 MHz, CDCb) δ 8.30 (s, 1H), 8.13 (s, 1H), 4.94-4.91 (m, 1H), 1.82 (d, J=6.8 Hz, 3H).

Step 3. 1-(1,1,1-Trifluoropropan-2-yl)-1/T-pyrazol-4-amine (40d)

Compound 40d (1.2 g) was synthesized in 45% yield by utilizing a similar preparative procedure to the second step of Example 8 with 40c (3.1 g crude, 14.83 mmol) as starting material. LC-MS (Method 1): $t_R$=0.38 mm, m/z (M+H)⁺=180.1.

Step 4. 2-Fluoro-4-(5-methyl-2-((1-(1,1,1-trifluoiOpiOpan-2-yl)-1//-pyrazol-4-yl)amino)pyrimidin-4-yl)phenol (40e)

To a mixture of 4a (100 mg, 0.42 mmol) and 40d (90 mg, 0.50 mmol) in n-BuOH (10 mL) was added cat. H2SO4 (0.5 mL, 1 drop in 1 mL n-BuOH). The mixture was stirred at 120° C. overnight. After cooling down to RT, the mixture was concentrated to dryness and purified by prep-HPLC (method A) to afford the title product (60 mg, 38% yield) as a yellow solid. LC-MS (Method 1): $t_R$=1.51 min, m/z (M+H)⁺=382.2.

Step 5. 3-(2-Fluoro-4-(5-methyl-2-((1-(1,1,1-trifluoropropan-2-yl)-1//-pyrazol-4-yl)amino)pyrimidin-4-yl)phenoxy)-2,2-dimethylpropanenitrile (40)

Compound 40 (5.4 mg) was synthesized in 7% yield by utilizing a similar preparative procedure to the final step of Example 1 with 40e (60 mg, 0.16 mmol) and 2-cyano-2-methylpropyl methanesulfonate (49 mg, 0.24 mmol) as starting materials. LC-MS (Method 1): $t_R$=3.41 min, m/z (M+H)⁺=463.1. ¾ NMR (400 MHz, CD₃OD) δ 8.32 (s, 1H), 8.14 (s, 1H), 7.70 (s, 1H), 7.58 (d, J=2.0 Hz, 1H), 7.55-7.51 (m, 2H), 7.28 (t, J=8.4 Hz, 1H), 5.11-5.04 (m, 1H), 4.15 (s, 2H), 2.30 (s, 3H), 1.74 (d, J=6.8 Hz, 3H), 1.54 (s, 6H). $^{19}$F NMR (376 MHz, CD₃OD) δ-77.67, -136.00.

Example 41

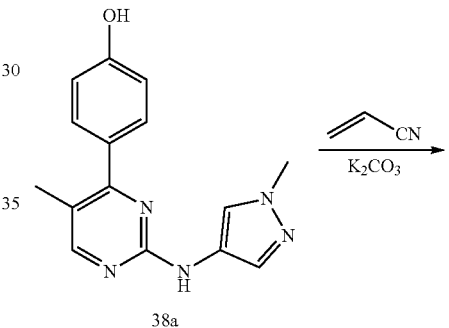

38a

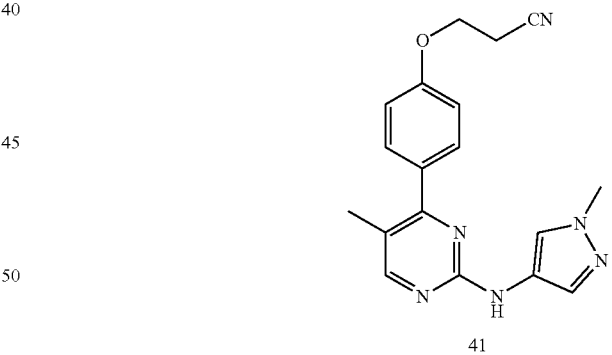

41

3-(4-(5-Methyl-2-((1-methyl-1/T-pyrazol-4-yl)amino)pyrimidin-4-yl)phenoxy)propanenitrile (41)

A mixture of 38a (226 mg, 0.68 mmol), K2CO3 (187 mg, 1.36 mmol) and t-BuOH (52 mg, 0.68 mmol) in acrylonitrile (2 ml) was stirred at 120° C. under microwave for 6 hours. The mixture was cooled to RT and concentrated. The residue was purified by Prep-HPLC to afford the title product (27.7 mg, 12% yield) as a yellow solid. LC-MS (Method 1): $t_R$=3.07 min, m/z (M+H)⁺=335.2. ¾ NMR (400 MHz, DMSO-d₆) δ 9.30 (s, 1H), 8.30 (s, 1H), 7.83 (s, 1H), 7.68 (d, J=8.4 Hz, 2H), 7.48 (s, 1H), 7.11 (t, J=8.8 Hz, 2H), 4.27 (t, J=6.0 Hz, 2H), 3.78 (s, 3H), 3.05 (t, J=6.4 Hz, 2H), 2.21 (s, 3H).

Example 42

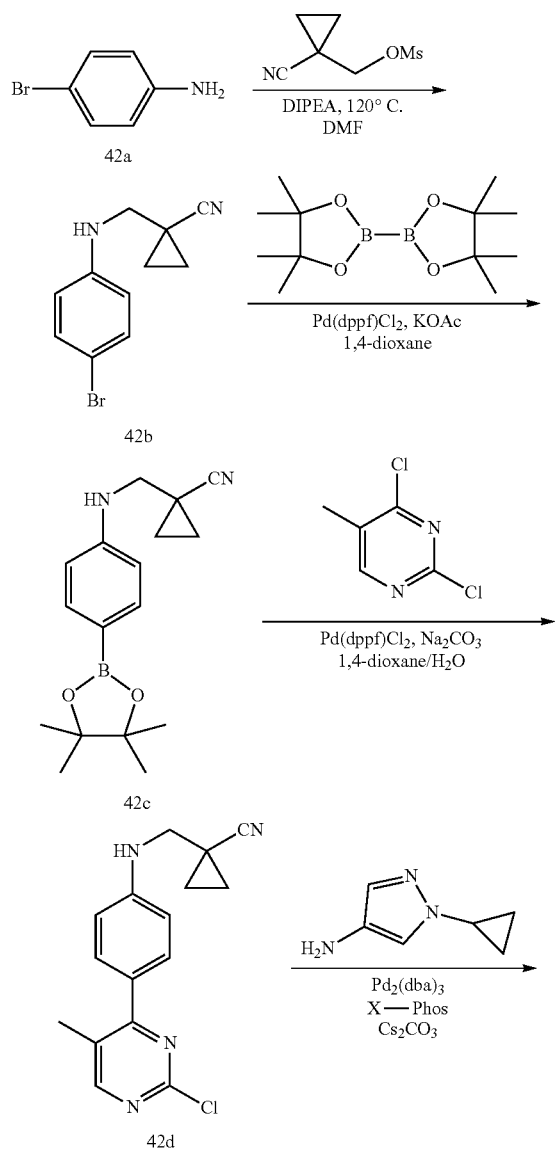

Step 1. 1-(((4-Bromophenyl)amino)methyl)cyclopropanecarbonitrile (42b)

A mixture of 4-bromoaniline (200 mg, 1.16 mmol), (1-cyanocyclopropyl)methyl methanesulfonate (305 mg, 1.74 mmol) and DIPEA (300 mg, 2.32 mmol) in DMF (1 mL) was stirred at 120° C. for 3 hours. The mixture was cooled down to R.T. and concentrated to dryness. The residue was purified by flash chromatography on silica gel (PE: EtOAc=5:1) to afford the title product (100 mg, 34%) as a yellow solid. LC-MS (Method 3): $t_R$=1.40 min, m/z $(M+H)^+$=251.1.

Step 2. 1-(((4-(4,4,5,5-Tetramethyl-1,3,2-dioxaborolan-2-yl)phenyl)amino)methyl)cyclopropanecarbonitrile (42c)

Compound 42c (119 mg) was synthesized in 100% yield by utilizing a similar preparative procedure to the second step of Example 10 with 42b (100 mg, 0.4 mmol) and 4,4,4',4',5,5,5',5'-octamethyl-2,2'-bi(1,3,2-dioxaborolane) (102 mg, 0.4 mmol) as starting materials. LC-MS (Method 3): $t_{3/4}$=1.60 min, m/z $(M+H)^+$=299.2.

Step 3. 1-(((4-(2-Chloro-5-methylpyrimidin-4-yl)phenyl)amino)methyl)cyclopropanecarbonitrile (42d)

Compound 42d (70 mg) was synthesized in 59% yield by utilizing a similar preparative procedure to the third step of Example 10 with 42c (119 mg, 0.4 mmol) and 2,4-dichloro-5-methylpyrimidine (98 mg, 0.6 mmol) as starting materials. LC-MS (Method 3): $t_R$=1.50 min, m/z $(M+H)^+$=299.1.

Step 4. 1-(((4-(2-((1-Cyclopropyl-Li7-pyrazol-4-yl)amino)-5-methylpyrimidin-4-yl)phenyl)amino)methyl)cyclopropanecarbonitrile (42)

Compound 42 (6 mg) was synthesized in 7% yield by a utilizing similar preparative procedure to the final step of Example 10 with 42d (70 mg, 0.23 mmol) and 1-cyclopropyl-1H-pyrazol-4-amine (43 mg, 0.35 mmol) as starting materials. LC-MS (Method 1): $t_R$=3.76 min, m/z $(M+H)^+$=386.2. ¾ NMR (400 MHz, CDCh) δ 8.21 (s, 1H), 7.92 (s, 1H), 7.58 (d, J=8.4 Hz, 2H), 7.49 (s, 1H), 6.71 (d, J=8.8 Hz, 2H), 6.66 (s, 1H), 4.15 (t, J=5.2 Hz, 1H), 3.59-3.55 (m, 1H), 3.39 (d, J=6.0 Hz, 2H), 2.28 (s, 3H), 1.35-1.32 (m, 2H), 1.15-1.11 (m, 2H), 1.05-1.01 (m, 2H), 1.00-0.96 (m, 2H).

Example 43

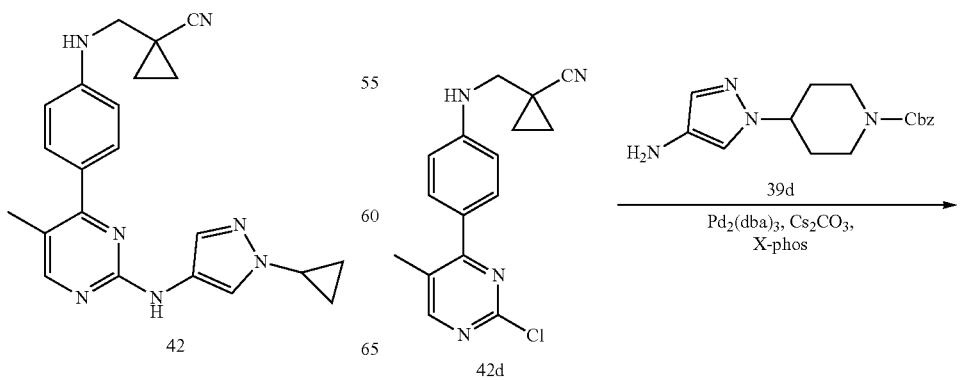

-continued

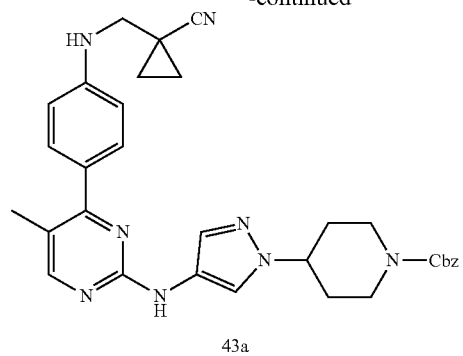

43a

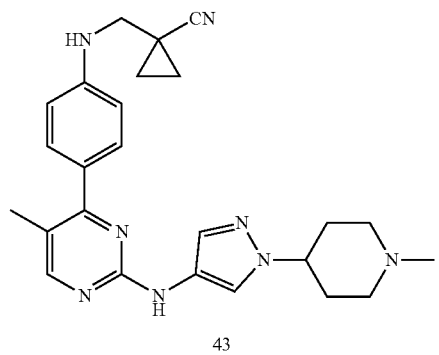

43

Step 1. Benzyl 4-(4-((4-(4-(((1-cyanocyclopropyl)methyl)amino)phenyl)-5-methylpyrimidin-2-yl)amino)-1//-pyrazol-1-yl)piperidine-1-carboxylate (43a)

Compound 43a (120 mg) was synthesized in 53% yield by utilizing a similar preparative procedure to the second step of Example 1 with 42d (120 mg, 0.4 mmol) and 39d (180 mg, 0.6 mmol) as starting materials. LC-MS (Method 3): $t_R$=1.64 min, m/z (M+H)$^+$=563.3.

Step 2. 1-(((4-(5-Methyl-2-((1-(1-methylpiperidin-4-yl)-1//-pyrazol-4-yl)amino)pyrimidin-4-yl)phenyl)amino)methyl)cyclopropanecarbonitrile (43)

A mixture of 43a (80 mg, 0.14 mmol) in MeOH (10 mL) was added Pd/C (40 mg, 10% wt, wetted with ca. 55% water) and Pd(OH)$_2$/C (40 mg, 20% wt) and one drop of formaldehyde (37% solution). The mixture was stirred at 40° C. under ¾ (1 atm) for 16 hrs. The reaction mixture was filtered and the filtrate was concentrated to afford a residue. The residue was purified by prep-HPLC (Method A) to afford the product (6 mg, 10% yield). LC-MS (Method 1): $t_R$=3.83 mm, m/z (M+H)$^+$=443.2. ¾ NMR (400 MHz, CDCh) δ 8.20 (s, 1H), 7.94 (s, 1H), 7.57 (d, J=8.4 Hz, 2H), 7.52 (s, 1H), 6.71 (d, J=8.8 Hz, 2H), 6.69 (s, 1H), 4.17-4.07 (m, 1H), 3.40 (d, J=6.0 Hz, 2H), 3.02-2.96 (m, 2H), 2.34 (s, 3H), 2.28 (s, 3H), 2.19-2.06 (m, 6H), 1.35-1.32 (m, 2H), 1.05-1.02 (m, 2H).

Example 44

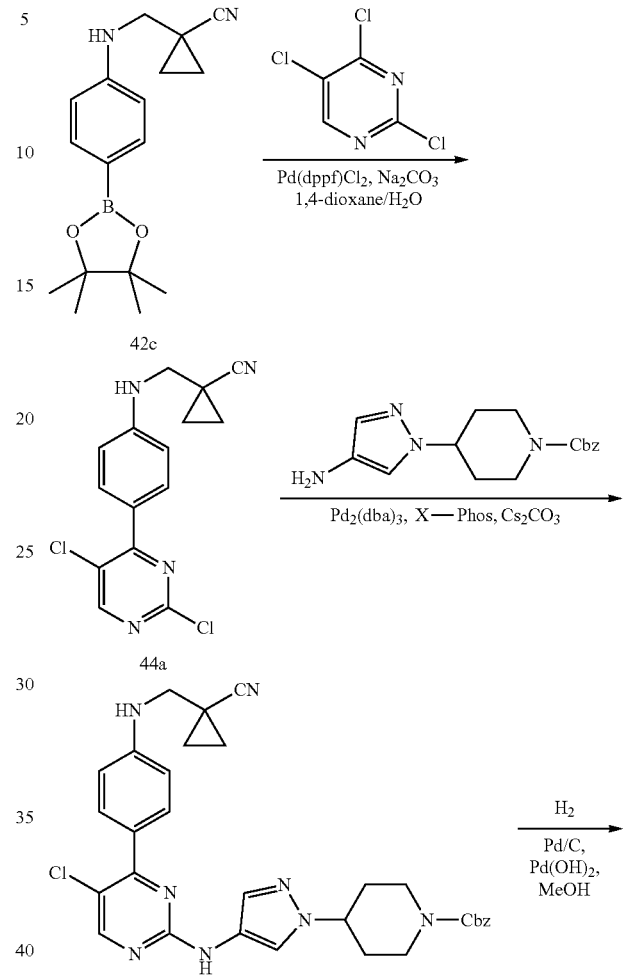

Step 1. 1-(((4-(2-Chloro-5-methylpyrimidin-4-yl)phenyl)amino)methyl)cyclopropanecarbonitrile (44a)

Compound 44a (126 mg) was synthesized in 79% yield by utilizing a similar preparative procedure to the second step of Example 42 with 42c (150 mg, 0.50 mmol) and 2,4,5-trichloropyrimidine (137 mg, 0.75 mmol) as starting materials. $^1$H NMR (400 MHz, CDCl$_3$) δ 8.52 (s, 1H), 7.96 (d, J=8.8 Hz, 2H), 6.69 (d, J=8.8 Hz, 2H), 4.37 (t, J=6.0 Hz, 1H), 3.40 (d, J=6.0 Hz, 2H), 1.36-1.33 (m, 2H), 1.27-1.24 (m, 2H).

Step 2. Benzyl 4-(4-((5-chloro-4-(4-(((1-cyanocyclopropyl)methyl)amino)phenyl)pyrimidin-2-yl)amino)-1//-pyrazol-1-yl)piperidine-1-carboxylate (44b)

Compound 44b (60 mg) was synthesized in 26% yield by utilizing a similar preparative procedure to the third step of Example 42 with 44a (96 mg, 0.30 mmol) and benzyl 4-(4-amino-1//-pyrazol-1-yl(piperidine-1-carboxylate (136 mg, 0.50 mmol) as starting materials. LC-MS (Method 3): $t_R$=1.67 min, m/z (M+H)$^+$=583.3.

Step 3. 1-(((4-(5-Chloro-2-((1-(piperidin-4-yl)-1/T-pyrazol-4-yl)amino)pyrimidin-4-yl)phenyl)amino)methyl)cyclopropanecarbonitrile (44)

A mixture of 44b (60 mg, 0.1 mmol) in MeOH (2 mL) was added Pd/C (24 mg, 10% wt, wetted with ca. 55% water) and Pd(OH)2/C (24 mg, 20% dihydroxypalladium on charcoal wt) under ¾ (1 atm) at 40° C. for 6 hours. The mixture was filtered and the filtrate was concentrated. The residue was purified by Prep-HPLC (Method A) to give the title product (1.5 mg, 3% yield) as a yellow solid. LC-MS (Method 1): $t_R$=3.20 min, m/z (M+H)$^+$=449.2. $^1$H NMR (400 MHz, CD3OD) δ 8.20 (s, 1H), 7.94 (s, 1H), 7.75 (d, J=8.4 Hz, 2H), 7.51 (s, 1H), 6.69 (d, J=8.8 Hz, 2H), 4.19-4.12 (m, 1H), 3.32 (s, 2H), 3.13-3.10 (m, 2H), 2.73-2.67 (m, 2H), 2.04-2.01 (m, 2H), 1.88-1.78 (m, 2H), 1.18-1.15 (m, 2H), 1.00-0.97 (m, 2H).

Example 45

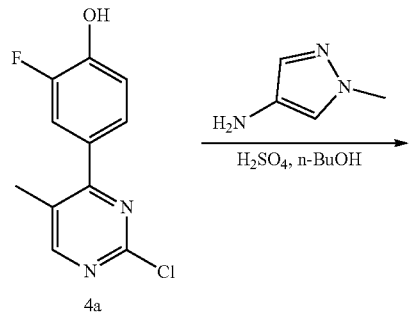

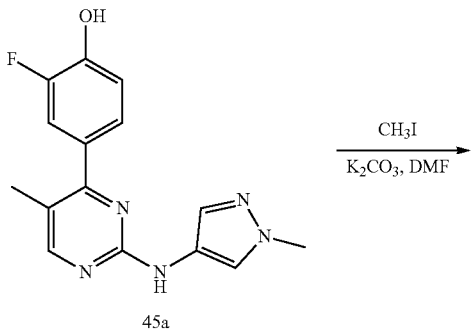

-continued

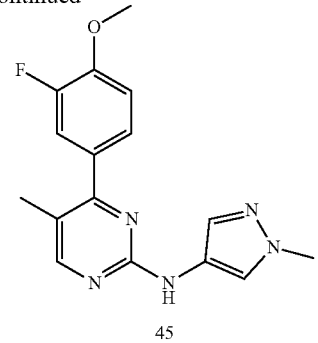

Step 1. 2-Fluoro-4-(5-methyl-2-((1-methyl-1//-pyrazol-4-yl)amino)pyrimidin-4-yl)phenol (45a)

To a mixture of 4a (500 mg, 2.1 mmol) and 1-methyl-1//-pyrazol-4-amine (295 mg, 2.55 mmol) in n-BuOH (8 mL) was added cat. H2SO4 (0.5 mL, 1 drop in 1 mL n-BuOH). The mixture was stirred at 120° C. overnight. After cooling down to RT, the mixture was concentrated to dryness and purified by prep-HPLC (Method A) to afford the title product as a yellow solid (357 mg, 47% yield). LC-MS (Method 3): $t_R$=1.28 min, m/z (M+H)$^+$=300.1.

Step 2. 4-(3-FluoiO-4-methoxyphenyl)-5-methyl-/V-(1-methyl-1//-pyrazol-4-yl)pyrimidin-2-amine (45)

A mixture of 45a (50 mg, 0.17 mmol), CH$_3$I (29 mg, 0.20 mmol) and K2CO3 (47 mg, 0.34 mmol) in DMF (1 mL) was stirred at 30° C. for 2 hours. The mixture was concentrated and purified by prep-HPLC (Method A) to get the product (5.4 mg, 10% yield) as a white solid. LC-MS (Method 1): $t_R$=3.34 mm, m/z (M+H)$^+$=314.2. $^1$H NMR (400 MHz, DMSO-d$_6$) δ 9.30 (s, 1H), 8.31 (s, 1H), 7.82 (s, 1H), 7.58-7.51 (m, 2H), 7.48 (s, 1H), 7.29 (t, J=8.8 Hz, 1H), 3.91 (s, 3H), 3.78 (s, 3H), 2.21 (s, 3H).

Example 46

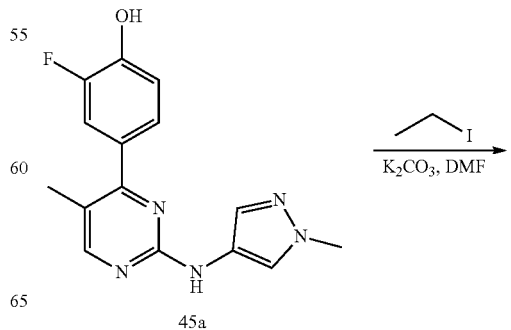

-continued

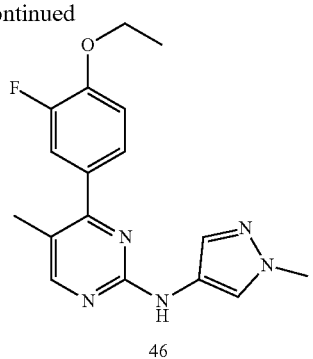

46

Step 1. 4-(4-Ethoxy-3-fluorophenyl)-5-methyl-7V-(1-methyl-Li7-pyrazol-4-yl)pyrimidin-2-amine (46)

Compound 46 (4.3 mg) was synthesized in 8% yield by utilizing a similar preparative procedure to the final step of Example 45 with 45a (50 mg, 0.17 mmol) and iodoethane (33 mg, 0.21 mmol) as starting materials. LC-MS (Method 1): $t_R$=3.36 min, m/z (M+H)$^+$=328.2. $^1$H NMR (400 MHz, DMSO-d$_6$) δ 9.30 (s, 1H), 8.31 (s, 1H), 7.82 (s, 1H), 7.58-7.49 (m, 3H), 7.28 (t, J=8.8 Hz, 1H), 4.22-4.17 (m, 2H), 3.79 (s, 3H), 2.22 (s, 3H), 1.39 (t, J=6.8 Hz, 3H).

Example 47

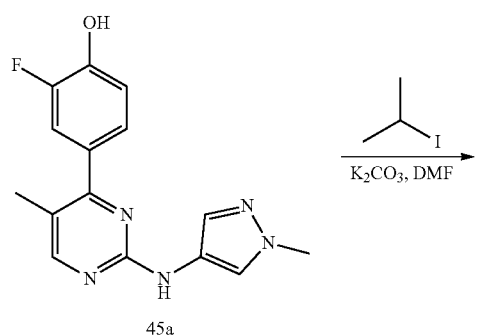

45a

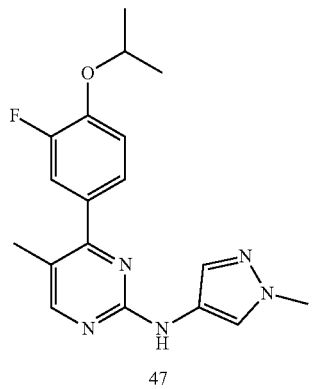

47

Step 1. 4-(3-FluoiO-4-isopropoxyphenyl)-5-methyl-/V-(1-methyl-1//-pyrazol-4-yl)pyrimidin-2-amine (47)

Compound 47 (4.3 mg) was synthesized in 8% yield by utilizing a similar preparative procedure to the final step of Example 45 with 45a (50 mg, 0.17 mmol) and 2-iodopropane (36 mg, 0.21 mmol) as starting materials. LC-MS (Method 1): $t_R$=3.01 min, m/z (M+H)$^+$=342.2. $^1$H NMR (400 MHz, DMSO-d$_6$) δ 9.29 (s, 1H), 8.31 (s, 1H), 7.82 (s, 1H), 7.55 (dd, J=2.0, 12.0 Hz, 1H), 7.50-7.48 (m, 2H), 7.28 (t, J=8.8 Hz, 1H), 4.76-4.73 (m, 1H), 3.78 (s, 3H), 2.22 (s, 3H), 1.33 (d, J=6.0 Hz, 6H).

Example 48

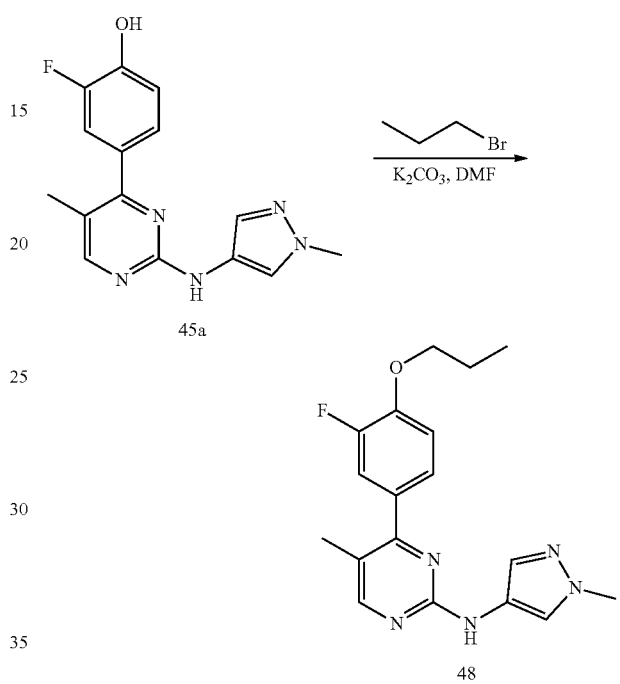

48

Step 1. 4-(3-FluoiO-4-propoxyphenyl)-5-methyl-/V-(1-methyl-1//-pyrazol-4-yl)pyrimidin-2-amine (48)

Compound 48 (4.9 mg) was synthesized in 8% yield by utilizing a similar preparative procedure to the final step of Example 45 with 45a (50 mg, 0.17 mmol) and 1-bromopropane (26 mg, 0.21 mmol) as starting materials. LC-MS (Method 1): $t_R$=3.99 min, m/z (M+H)$^+$=342.2. $^1$H NMR (400 MHz, DMSO-d$_6$) δ 9.30 (s, 1H), 8.31 (s, 1H), 7.82 (s, 1H), 7.55 (dd, J=2.0, 12.0 Hz, 1H), 7.50-7.49 (m, 2H), 7.28 (t, J=8.8 Hz, 1H), 4.08 (t, J=6.4 Hz, 2H), 3.78 (s, 3H), 2.22 (s, 3H), 1.83-1.74 (m, 2H), 1.01 (t, J=7.2 Hz, 3H).

Example 49

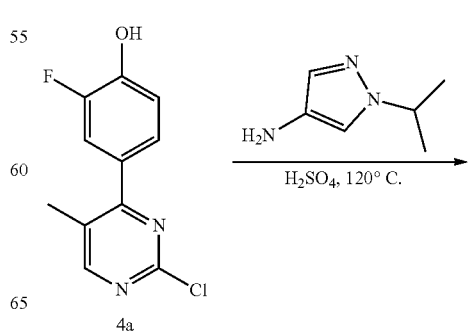

4a

109

-continued

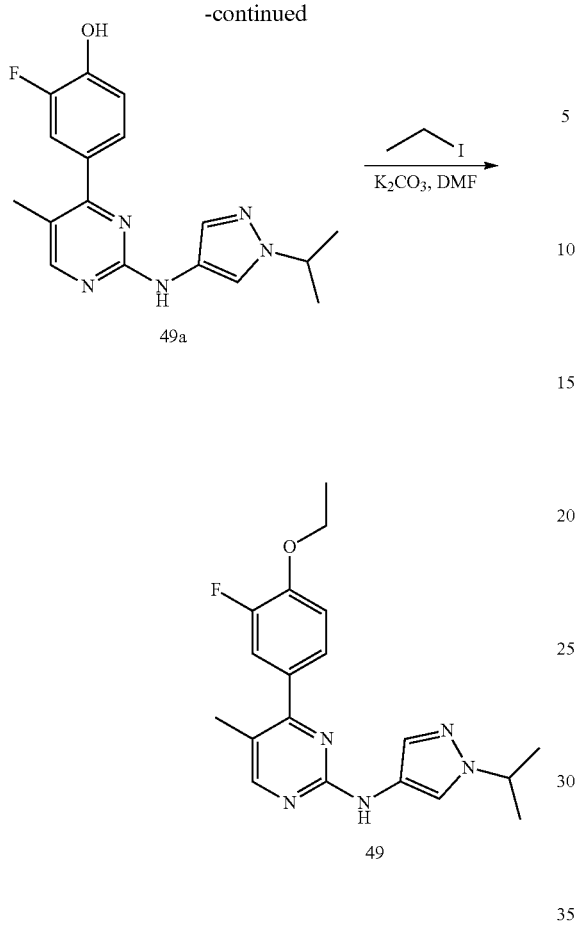

Step 1. 2-Fluoro-4-(2-((1-isopropyl-1//-pyrazol-4-yl)amino)-5-methylpyrimidin-4-yl)phenol (49a)

Compound 49a (40 mg) was synthesized in 42% yield by utilizing a similar preparative procedure to the first step of Example 45 with 4a (70 mg, 0.30 mmol) and 1-isopropyl-1//-pyrazol-4-amine (74 mg, 0.59 mmol) as starting materials. LC-MS (Method 3): $t_R$=1.47 min, m/z (M+H)$^+$=328.1.

Step 2. 4-(4-Ethoxy-3-fluorophenyl)-7V-(1-isopropyl-li/-pyrazol-4-yl)-5-methylpyrimidin-2-amine (49)

Compound 49 (10 mg) was synthesized in 23% yield by utilizing a similar preparative procedure to the final step of Example 45 with 49a (40 mg, 0.12 mmol) and iodoethane (23 mg, 0.15 mmol) as starting materials. LC-MS (Method 1): $t_R$=3.54 min, m/z (M+H)$^+$=356.2. $^1$H NMR (400 MHz, CDCb) δ 8.26 (s, 1H), 7.90 (s, 1H), 7.51 (s, 1H), 7.47 (d, J=12.8 Hz, 1H), 7.41 (d, J=8.4 Hz, 1H), 7.03 (t, J=8.4 Hz, 1H), 6.92 (s, 1H), 4.49-4.42 (m, 1H), 4.18 (q, J=6.8 Hz, 2H), 2.28 (s, 3H), 1.52-1.47 (m, 9H).

110

Example 50

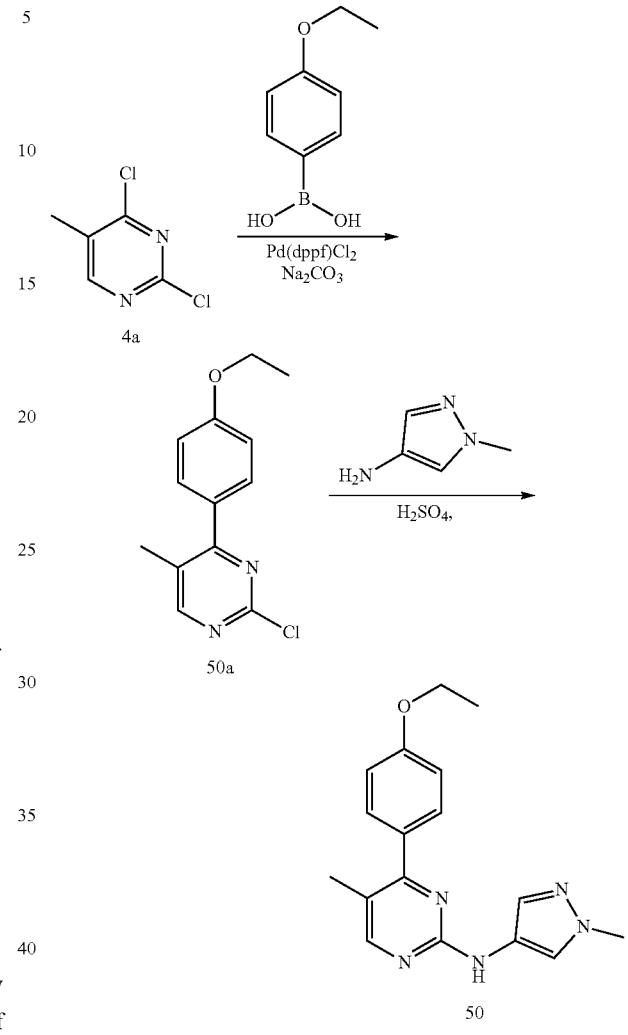

Step 1. 2-Chloro-4-(4-ethoxyphenyl)-5-methylpyrimidine (50a)

Compound 50a (510 mg) was synthesized in 69% yield by utilizing a similar preparative procedure to the first step of Example 1 with 1a (500 mg, 3.01 mmol) and (4-ethoxyphenyl)boronic acid (491 mg, 3.01 mmol) as starting materials. $^1$H NMR (400 MHz, DMSO-d$_6$) δ 8.64 (s, 1H), 7.69 (d, J=9.2 Hz, 2H), 7.07 (d, J=9.2 Hz, 2H), 4.11 (q, J=7.2 Hz, 2H), 2.37 (s, 3H), 1.36 (t, J=6.8 Hz, 3H).

Step 2. 4-(4-Ethoxyphenyl)-5-methyl-/V-(1-methyl-1//-pyrazol-4-yl)pyrimidin-2-amine (50)

Compound 50 (3.6 mg) was synthesized in 4% yield by utilizing a similar preparative procedure to the first step of Example 45 with 50a (70 mg, 0.28 mmol) and 1-methyl-1//-pyrazol-4-amine (33 mg, 0.34 mmol) as starting materials. LC-MS (Method 1): $t_R$=3.56 min, m/z (M+H)$^+$= 310.2. ¾ NMR (300 MHz, CDCb) δ 8.28 (s, 1H), 7.90 (s, 1H), 7.64 (d, J=8.7 Hz, 2H), 7.53 (s, 1H), 7.03 (d, J=8.7 Hz, 2H), 6.78 (s, 1H), 4.11 (q, J=6.9 Hz, 2H), 3.92 (s, 3H), 2.31 (s, 3H), 1.36 (t, J=6.9 Hz, 3H).

Example 51. Testing for Biological Activities

Compounds were tested against JAK1, JAK2, JAK2V617F and TYK2.

Assay Formats: JAK activity was determined in the reaction buffer 50 mM HEPES, 0.01% Brij35, 10 mMMgCl2, 2 mMDTT by a microfluidic assay. The phosphorylation of a FAM labeled peptide substrate was monitored in the Caliper EZ Reader II (Perkin Elmer). The assay condition for each batch of enzyme (Carna Biosciences) was optimized to obtain 10% conversion rate of peptide substrate.

The test compounds were dissolved in DMSO to a stock concentration of 10 mM. 3-fold serially diluted compounds with top concentration of 5 µM were pre-incubated with JAK1, JAK2, JAK2V617F or TYK2 for 10 min at ambient temperature. The final DMSO concentration of assay mixture was 1%. FAM labeled peptide substrate (final concentration 3 M) and ATP (1 mM concentration) were sequentially added to initiate the kinase reaction at 28° C. The reaction was stopped by adding 50 mMEDTA. The reaction time for JAK1, JAK2, JAK2V617F and TYK2 was 120 min, 20 min, 30 min and 10 min, respectively.

The well in the test plate without enzyme was defined as 100% inhibition. And the well without compound but with equivalent DMSO was defined as no inhibition. The percent inhibition was calculated by the following formula.

% Inhibition=(Conversion$_{max}$−Conversion$_{sample}$)/(Conversion$_{max}$−Conversion$_{min}$)*100 Conversion$_{max}$ means the conversion rate in the positive well without addition of compound Conversion$_{min}$ means the conversion rate in the well without addition of enzyme Conversion$_{sample}$ means the conversion rate of test compounds The dose-response (percent inhibition) curve was plotted and IC50 values were determined by GraphPad software.

Exemplary results are summarized in Table 1.

TABLE 1

| Summary of Exemplary Structures | | | |
|---|---|---|---|
| Example | Structure | IUPAC name | Mol Weight |
| 1 | 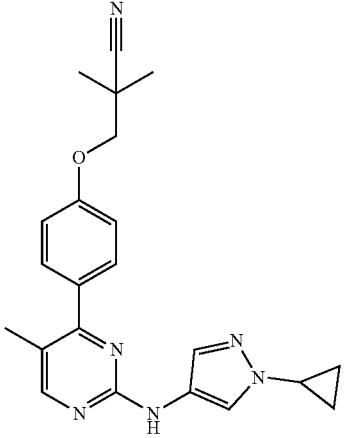 [SMILES: Cc1cnc(Nc2cnn(C3CC3)c2)nc1-c1ccc(OCC(C)(C)C#N)cc1] | 3-(4-(2-((1-cyclopropyl-1H-pyrazol-4-yl)amino)-5-methylpyrimidin-4-yl)phenoxy)-2,2-dimethylpropanenitrile | 388.46 |
| 2 | 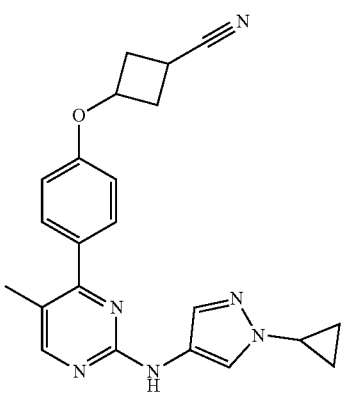 [SMILES: Cc1cnc(Nc2cnn(C3CC3)c2)nc1-c1ccc(OC2CC(C#N)C2)cc1] | 3-(4-(2-((1-cyclopropyl-1H-pyrazol-4-yl)amino)-5-methylpyrimidin-4-yl)phenoxy)cyclobutanecarbonitrile | 386.45 |

TABLE 1-continued

Summary of Exemplary Structures

| Example | Structure | IUPAC name | Mol Weight |
|---|---|---|---|
| 3 | 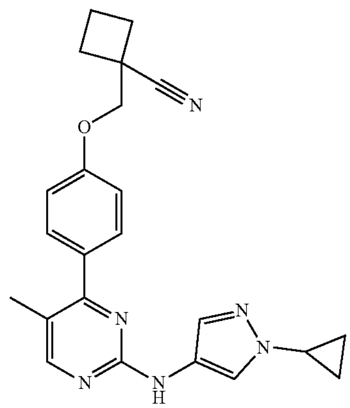 [SMILES: Cc1cnc(Nc2cnn(C3CC3)c2)nc1-c1ccc(OCC2(C#N)CCC2)cc1] | 1-((4-(2-((1-cyclopropyl-1H-pyrazol-4-yl)amino)-5-methylpyrimidin-4-yl)phenoxy)methyl)cyclobutane-carbonitrile | 400.48 |
| 4 | 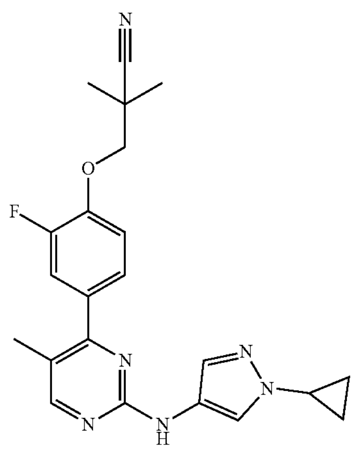 [SMILES: Cc1cnc(Nc2cnn(C3CC3)c2)nc1-c1ccc(OCC(C)(C)C#N)c(F)c1] | 3-(4-(2-((1-cyclopropyl-1H-pyrazol-4-yl)amino)-5-methylpyrimidin-4-yl)-2-fluorophenoxy)-2,2-dimethylpropanenitrile | 406.46 |
| 5 | 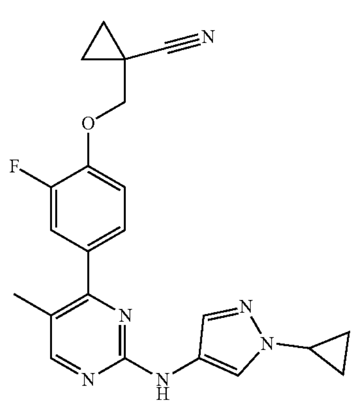 [SMILES: Cc1cnc(Nc2cnn(C3CC3)c2)nc1-c1ccc(OCC2(C#N)CC2)c(F)c1] | 1-((4-(2-((1-cyclopropyl-1H-pyrazol-4-yl)amino)-5-methylpyrimidin-4-yl)-2-fluorophenoxy)methyl)cyclopropane-carbonitrile | 404.44 |

TABLE 1-continued

Summary of Exemplary Structures

| Example | Structure | IUPAC name | Mol Weight |
|---|---|---|---|
| 6 | 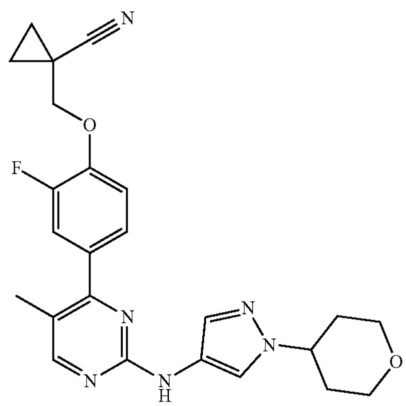 [SMILES: Cc1cnc(Nc2cnn(C3CCOCC3)c2)nc1-c1ccc(OCC2(C#N)CC2)c(F)c1] | 1-((2-fluoro-4-(5-methyl-2-((1-(tetrahydro-2H-pyran-4-yl)-1H-pyrazol-4-yl)amino)pyrimidin-4-yl)phenoxy)methyl)cyclopropane-carbonitrile | 448.49 |
| 7 | 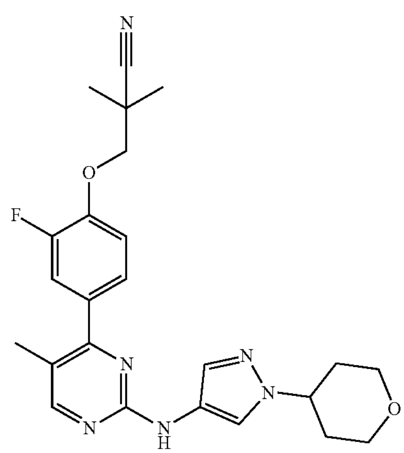 [SMILES: Cc1cnc(Nc2cnn(C3CCOCC3)c2)nc1-c1ccc(OCC(C)(C)C#N)c(F)c1] | 3-(2-fluoro-4-(5-methyl-2-((1-(tetrahydro-2H-pyran-4-yl)-1H-pyrazol-4-yl)amino)pyrimidin-4-yl)phenoxy)-2,2-dimethylpropanenitrile | 450.51 |
| 8 | 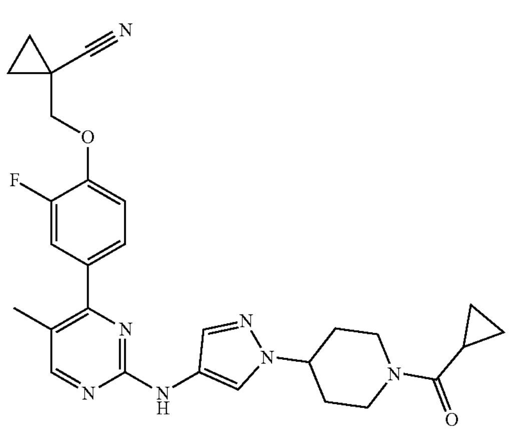 [SMILES: Cc1cnc(Nc2cnn(C3CCN(C(=O)C4CC4)CC3)c2)nc1-c1ccc(OCC2(C#N)CC2)c(F)c1] | 1-((4-(2-((1-(1-(cyclopropanecarbonyl)piperidin-4-yl)-1H-pyrazol-4-yl)amino)-5-methylpyrimidin-4-yl)-2-fluorophenoxy)methyl)cyclopropane-carbonitrile | 515.58 |

TABLE 1-continued

Summary of Exemplary Structures

| Example | Structure | IUPAC name | Mol Weight |
|---------|-----------|------------|------------|
| 9 | 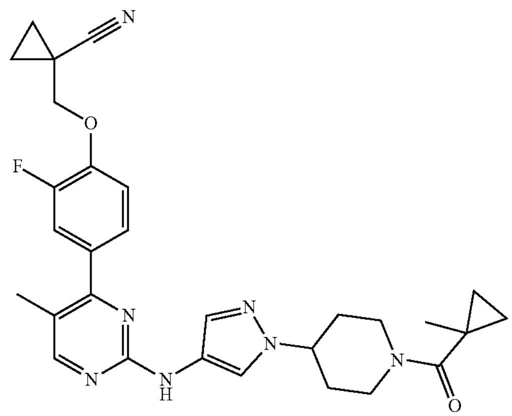 [SMILES: Cc1cnc(Nc2cnn(C3CCN(C(=O)C4(C)CC4)CC3)c2)nc1-c1ccc(OCC2(C#N)CC2)c(F)c1] | 1-((2-fluoro-4-(5-methyl-2-((1-(1-(1-methylcyclopropanecarbonyl)piperidin-4-yl)-1H-pyrazol-4-yl)amino)pyrimidin-4-yl)phenoxy)methyl)cyclopropane-carbonitrile | 529.61 |
| 10 | 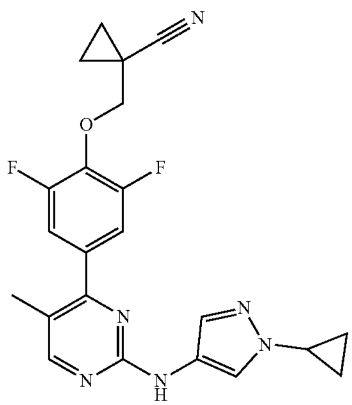 [SMILES: Cc1cnc(Nc2cnn(C3CC3)c2)nc1-c1cc(F)c(OCC2(C#N)CC2)c(F)c1] | 1-((4-(2-((1-cyclopropyl-1H-pyrazol-4-yl)amino)-5-methylpyrimidin-4-yl)-2,6-difluorophenoxy)methyl)cyclopropane carbonitrile | 422.43 |
| 11 | 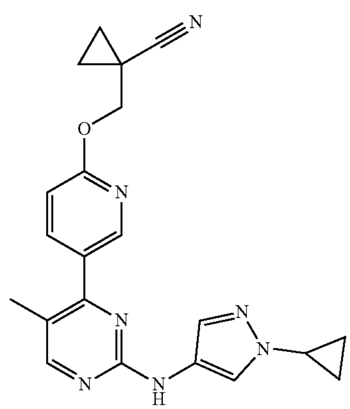 [SMILES: Cc1cnc(Nc2cnn(C3CC3)c2)nc1-c1ccc(OCC2(C#N)CC2)nc1] | 1-(((5-(2-((l-cyclopropyl-1H-pyrazol-4-yl)amino)-5-methylpyrimidin-4-yl)pyridin-2-yl)oxy)methyl)cyclopropanecarbonitrile | 387.44 |
| 12 | 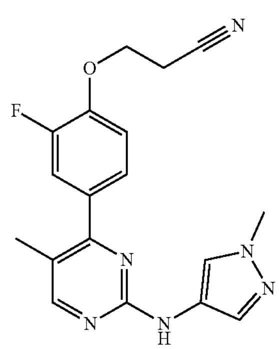 [SMILES: Cc1cnc(Nc2cnn(C)c2)nc1-c1ccc(OCCC#N)c(F)c1] | 3-(2-fluoro-4-(5-methyl-2-((1-methyl-1H-pyrazol-4-yl)amino)pyrimidin-4-yl)phenoxy)propanenitrile | 352.37 |

TABLE 1-continued

Summary of Exemplary Structures

| Example | Structure | IUPAC name | Mol Weight |
|---|---|---|---|
| 13 | 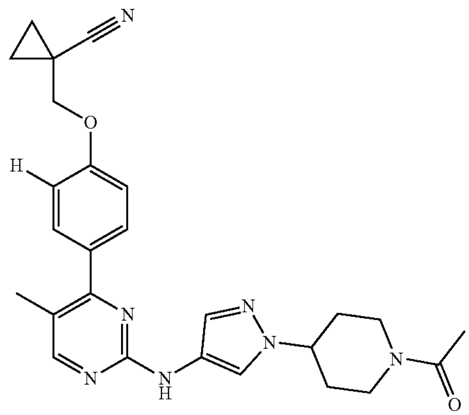 [SMILES: CC(=O)N1CCC(n2cc(Nc3ncc(C)c(-c4ccc(OCC5(C#N)CC5)cc4)n3)cn2)CC1] | 1-((4-(2-((1-(1-acetylpiperidin-4-yl)-1H-pyrazol-4-yl)amino)-5-methylpyrimidin-4-yl)-2-fluorophenoxy)methyl)cyclopropane-carbonitrile | 489.54 |
| 14 | 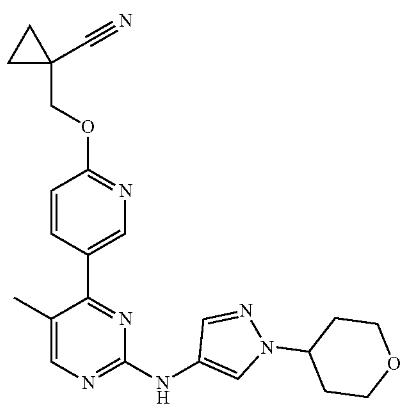 [SMILES: Cc1cnc(Nc2cnn(C3CCOCC3)c2)nc1-c1ccc(OCC2(C#N)CC2)nc1] | 1-(((5-(5-methyl-2-((1-(tetrahydro-2H-pyran-4-yl)-1H-pyrazol-4-yl)amino)pyrimidin-4-yl)pyridin-2-yl)oxy)methyl)cyclopropanecarbonitrile | 431.49 |
| 15 | 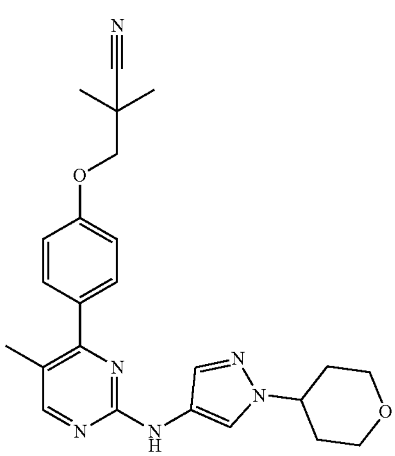 [SMILES: Cc1cnc(Nc2cnn(C3CCOCC3)c2)nc1-c1ccc(OCC(C)(C)C#N)cc1] | 2,2-dimethyl-3-(4-(5-methyl-2-((1-(tetrahydro-2H-pyran-4-yl)-1H-pyrazol-4-yl)amino)pyrimidin-4-yl)phenoxy)propanenitrile | 432.52 |

TABLE 1-continued

Summary of Exemplary Structures

| Example | Structure | IUPAC name | Mol Weight |
|---------|-----------|------------|------------|
| 16 | 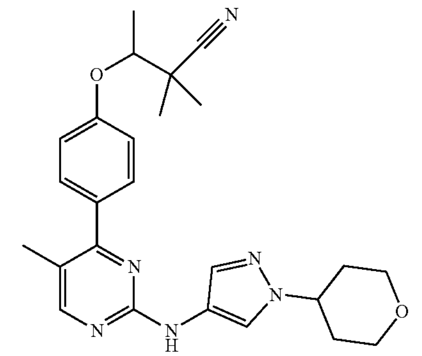 [SMILES: Cc1cnc(Nc2cnn(C3CCOCC3)c2)nc1-c1ccc(OC(C)C(C)(C)C#N)cc1] | 2,2-dimethyl-3-(4-(5-methyl-2-((1-(tetrahydro-2H-pyran-4-yl)-1H-pyrazol-4-yl)amino)pyrimidin-4-yl)phenoxy)butanenitrile | 446.54 |
| 17 | 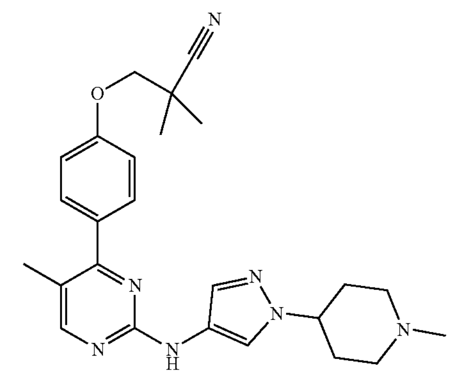 | 2,2-dimethyl-3-(4-(5-methyl-2-((1-(1-methylpiperidin-4-yl)-1H-pyrazol-4-yl)amino)pyrimidin-4-yl)phenoxy)propanenitrile | 445.56 |
| 18 | 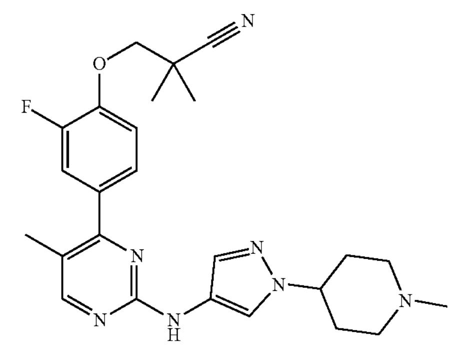 | 3-(2-fluoro-4-(5-methyl-2-((1-(1-methylpiperidin-4-yl)-1H-pyrazol-4-yl)amino)pyrimidin-4-yl)phenoxy)-2,2-dimethylpropanenitrile | 463.55 |
| 19 | 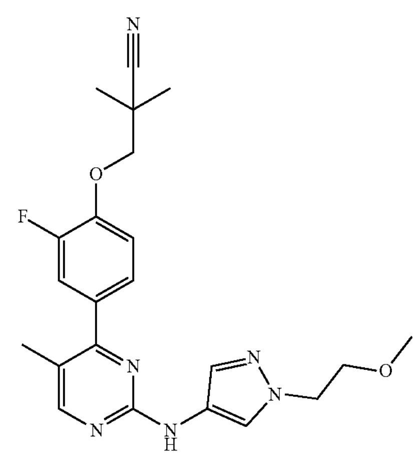 | 3-(2-fluoro-4-(2-((1-(2-methoxyethyl)-1H-pyrazol-4-yl)amino)-5-methylpyrimidin-4-yl)phenoxy)-2,2-dimethylpropanenitrile | 424.47 |

TABLE 1-continued

Summary of Exemplary Structures

| Example | Structure | IUPAC name | Mol Weight |
|---|---|---|---|
| 20 | 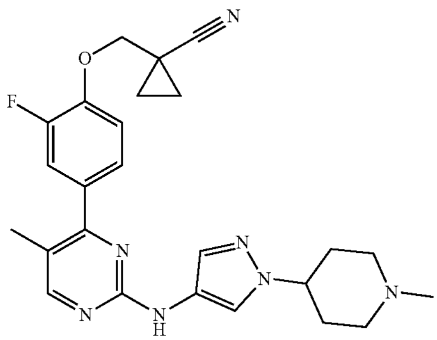 | 1-((2-fluoro-4-(5-methyl-2-((1-(1-methylpiperidin-4-yl)-1H-pyrazol-4-yl)amino)pyrimidin-4-yl)phenoxy)methyl)cyclopropanecarbonitrile | 461.53 |
| 21 | 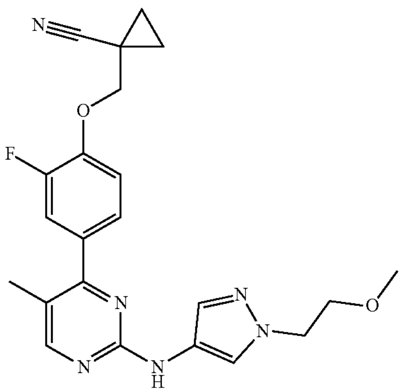 | 1-((2-fluoro-4-(2-((1-(2-methoxyethyl)-1H-pyrazol-4-yl)amino)-5-methylpyrimidin-4-yl)phenoxy)methyl)cyclopropanecarbonitrile | 422.45 |
| 22 | 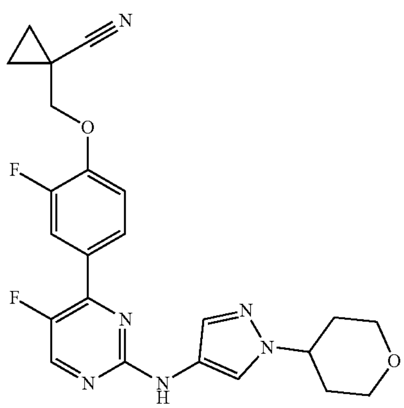 [SMILES: N#CC1(COc2ccc(-c3nc(Nc4cnn(C5CCOCC5)c4)ncc3F)cc2F)CC1] | 1-((2-fluoro-4-(5-fluoro-2-((1-(tetrahydro-2H-pyran-4-yl)-1H-pyrazol-4-yl)amino)pyrimidin-4-yl)phenoxy)methyl)cyclopropanecarbonitrile | 452.46 |
| 23 | 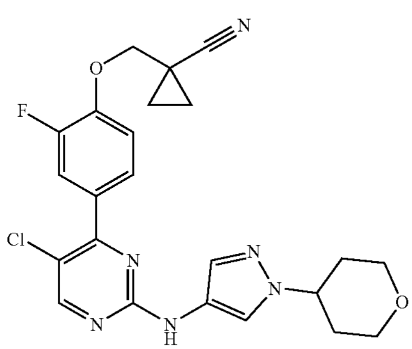 [SMILES: N#CC1(COc2ccc(-c3nc(Nc4cnn(C5CCOCC5)c4)ncc3Cl)cc2F)CC1] | 1-((4-(5-chloro-2-((1-(tetrahydro-2H-pyran-4-yl)-1H-pyrazol-4-yl)amino)pyrimidin-4-yl)-2-fluorophenoxy)methyl)cyclopropanecarbonitrile | 468.91 |

TABLE 1-continued

Summary of Exemplary Structures

| Example | Structure | IUPAC name | Mol Weight |
|---|---|---|---|
| 24 | 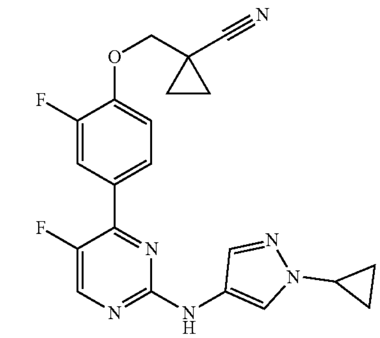 [SMILES: N#CC1(COc2ccc(-c3nc(Nc4cnn(C5CC5)c4)ncc3F)cc2F)CC1] | 1-((4-(2-((1-cyclopropyl-1H-pyrazol-4-yl)amino)-5-fluoropyrimidin-4-yl)-2-fluorophenoxy)methyl)cyclopropane-carbonitrile | 408.40 |
| 25 | 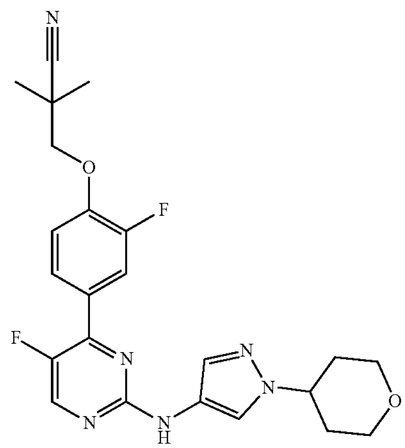 [SMILES: CC(C)(C#N)COc1ccc(-c2nc(Nc3cnn(C4CCOCC4)c3)ncc2F)cc1F] | 3-(2-fluoro-4-(5-fluoro-2-((1-(tetrahydro-2H-pyran-4-yl)-1H-pyrazol-4-yl)amino)pyrimidin-4-yl)phenoxy)-2,2-dimethylpropanenitrile | 454.47 |
| 26 | 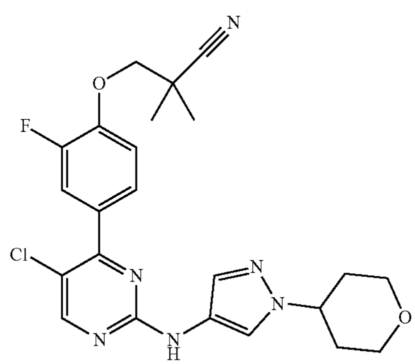 [SMILES: CC(C)(C#N)COc1ccc(-c2nc(Nc3cnn(C4CCOCC4)c3)ncc2Cl)cc1F] | 3-(4-(5-chloro-2-((1-(tetrahydro-2H-pyran-4-yl)-1H-pyrazol-4-yl)amino)pyrimidin-4-yl)-2-fluorophenoxy)-2,2-dimethylpropanenitrile | 470.93 |
| 27 | 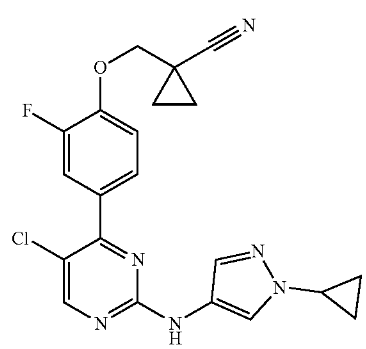 [SMILES: N#CC1(COc2ccc(-c3nc(Nc4cnn(C5CC5)c4)ncc3Cl)cc2F)CC1] | 1-((4-(5-chloro-2-((1-cyclopropyl-1H-pyrazol-4-yl)amino)pyrimidin-4-yl)-2-fluorophenoxy)methyl)cyclopropane carbonitrile | 424.86 |

TABLE 1-continued

Summary of Exemplary Structures

| Example | Structure | IUPAC name | Mol Weight |
|---|---|---|---|
| 28 | 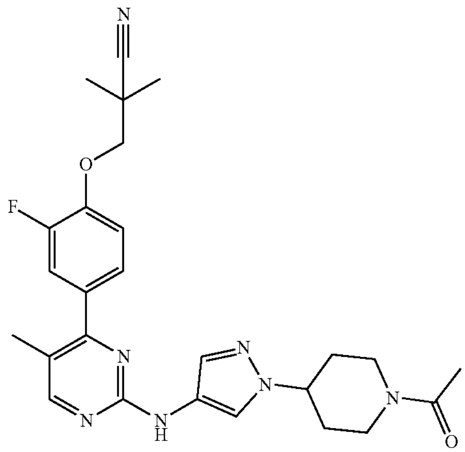 [SMILES: CC(=O)N1CCC(n2cc(Nc3ncc(C)c(-c4ccc(OCC(C)(C)C#N)c(F)c4)n3)cn2)CC1] | 3-(4-(2-((1-(1-acetylpiperidin-4-yl)-1H-pyrazol-4-yl)amino)-5-methylpyrimidin-4-yl)-2-fluorophenoxy)-2,2-dimethylpropanenitrile | 491.56 |
| 29 | 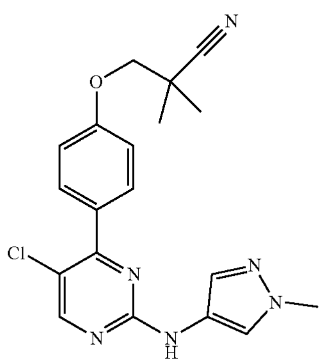 [SMILES: Cn1cc(Nc2ncc(Cl)c(-c3ccc(OCC(C)(C)C#N)cc3)n2)cn1] | 3-(4-(5-chloro-2-((1-methyl-1H-pyrazol-4-yl)amino)pyrimidin-4-yl)phenoxy)-2,2-dimethylpropanenitrile | 382.85 |
| 30 | 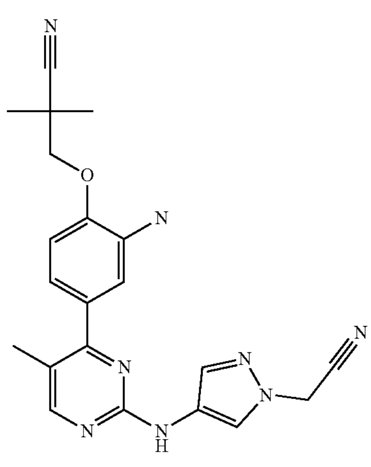 [SMILES: Cc1cnc(Nc2cnn(CC#N)c2)nc1-c1ccc(OCC(C)(C)C#N)c(N)c1] | 3-(4-(2-((1-(cyanomethyl)-1H-pyrazol-4-yl)amino)-5-methylpyrimidin-4-yl)-2-fluorophenoxy)-2,2-dimethylpropanenitrile | 405.43 |

TABLE 1-continued

Summary of Exemplary Structures

| Example | Structure | IUPAC name | Mol Weight |
|---|---|---|---|
| 31 | 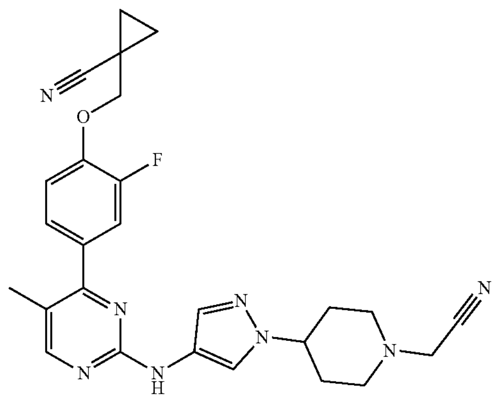 [SMILES: Cc1cnc(Nc2cnn(C3CCN(CC#N)CC3)c2)nc1-c1ccc(OCC2(C#N)CC2)c(F)c1] | 1-((4-(2-((1-(cyanomethyl)-1H-pyrazol-4-yl)amino)-5-methylpyrimidin-4-yl)-2-fluorophenoxy)methyl)cyclopropane-carbonitrile | 403.41 |
| 32 | 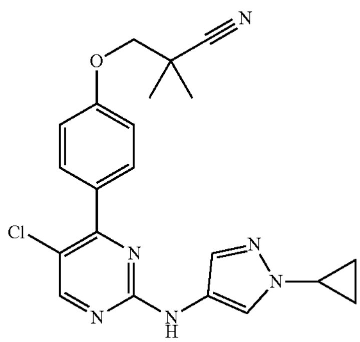 [SMILES: CC(C)(C#N)COc1ccc(-c2nc(Nc3cnn(C4CC4)c3)ncc2Cl)cc1] | 3-(4-(5-chloro-2-((1-cyclopropyl-1H-pyrazol-4-yl)amino)pyrimidin-4-yl)phenoxy)-2,2-dimethylpropanenitrile | 408.88 |
| 33 | 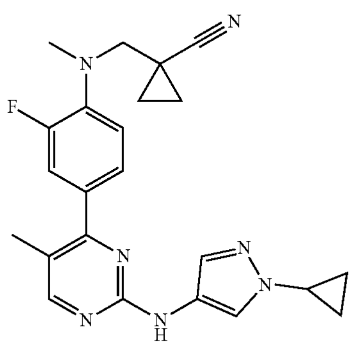 [SMILES: Cc1cnc(Nc2cnn(C3CC3)c2)nc1-c1ccc(N(C)CC2(C#N)CC2)c(F)c1] | 1-(((4-(2-((1-cyclopropyl-1H-pyrazol-4-yl)amino)-5-methylpyrimidin-4-yl)-2-fluorophenyl)(methyl)amino)methyl)cyclopropanecarbonitrile | 417.48 |
| 34 | 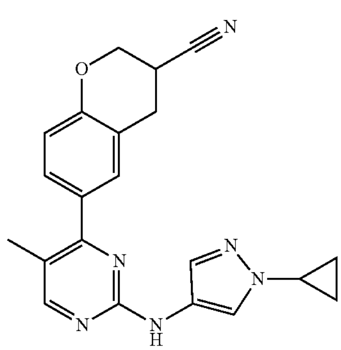 [SMILES: Cc1cnc(Nc2cnn(C3CC3)c2)nc1-c1ccc2c(c1)CC(C#N)CO2] | 6-(2-((1-cyclopropyl-1H-pyrazol-4-yl)amino)-5-methylpyrimidin-4-yl)chroman-3-carbonitrile | 372.42 |

TABLE 1-continued

Summary of Exemplary Structures

| Example | Structure | IUPAC name | Mol Weight |
|---|---|---|---|
| 35 | 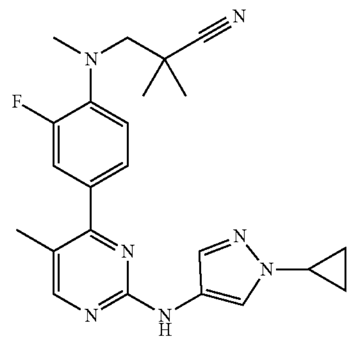 [SMILES: Cc1cnc(Nc2cnn(C3CC3)c2)nc1-c1ccc(N(C)CC(C)(C)C#N)c(F)c1] | 3-((4-(2-((1-cyclopropyl-1H-pyrazol-4-yl)amino)-5-methylpyrimidin-4-yl)-2-fluorophenyl)(methyl)amino)-2,2-dimethylpropanenitrile | 419.50 |
| 36 | 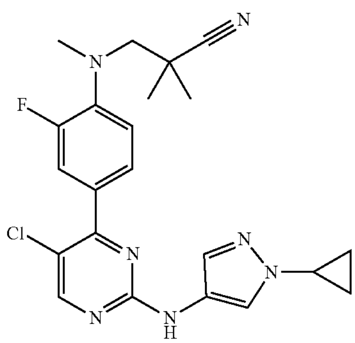 [SMILES: CN(CC(C)(C)C#N)c1ccc(-c2nc(Nc3cnn(C4CC4)c3)ncc2Cl)cc1F] | 3-((4-(5-chloro-2-((1-cyclopropyl-1H-pyrazol-4-yl)amino)pyrimidin-4-yl)-2-fluorophenyl)(methyl)amino)-2,2-dimethylpropanenitrile | 439.92 |
| 37 | 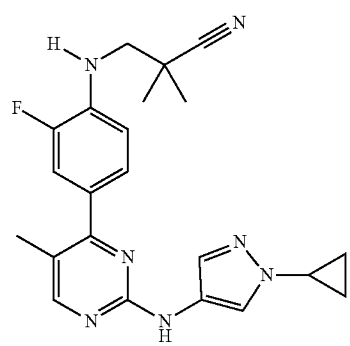 [SMILES: Cc1cnc(Nc2cnn(C3CC3)c2)nc1-c1ccc(NCC(C)(C)C#N)c(F)c1] | 3-((4-(2-((1-cyclopropyl-1H-pyrazol-4-yl)amino)-5-methylpyrimidin-4-yl)-2-fluorophenyl)amino)-2,2-dimethylpropanenitrile | 405.47 |
| 38 | 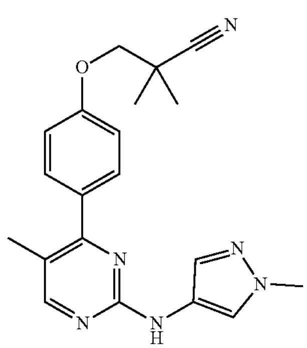 | 2,2-dimethyl-3-(4-(5-methyl-2-((1-methyl-1H-pyrazol-4-yl)amino)pyrimidin-4-yl)phenoxy)propanenitrile | 362.43 |

TABLE 1-continued

Summary of Exemplary Structures

| Example | Structure | IUPAC name | Mol Weight |
|---|---|---|---|
| 39 | 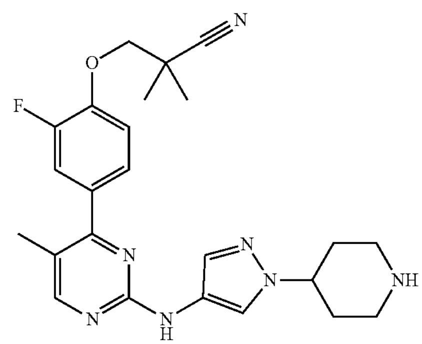 [SMILES: Cc1cnc(Nc2cnn(C3CCNCC3)c2)nc1-c1ccc(OCC(C)(C)C#N)c(F)c1] | 3-(2-fluoro-4-(5-methyl-2-((1-(piperidin-4-yl)-1H-pyrazol-4-yl)amino)pyrimidin-4-yl)phenoxy)-2,2-dimethylpropanenitrile | 449.52 |
| 40 | 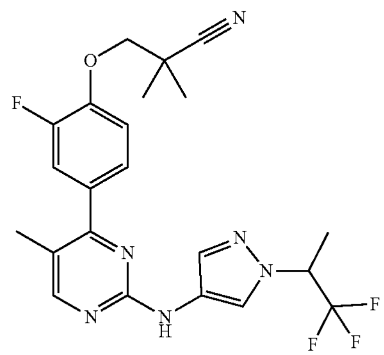 [SMILES: Cc1cnc(Nc2cnn(C(C)C(F)(F)F)c2)nc1-c1ccc(OCC(C)(C)C#N)c(F)c1] | 3-(2-fluoro-4-(5-methyl-2-((1-(1,1,1-trifluoropropan-2-yl)-1H-pyrazol-4-yl)amino)pyrimidin-4-yl)phenoxy)-2,2-dimethylpropanenitrile | 462.44 |
| 41 | 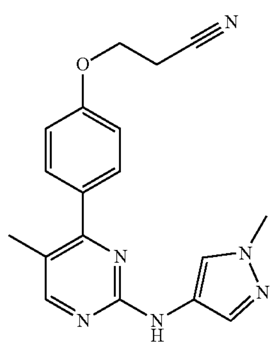 | 3-(4-(5-methyl-2-((1-methyl-1H-pyrazol-4-yl)amino)pyrimidin-4-yl)phenoxy)propanenitrile | 334.37 |
| 42 | 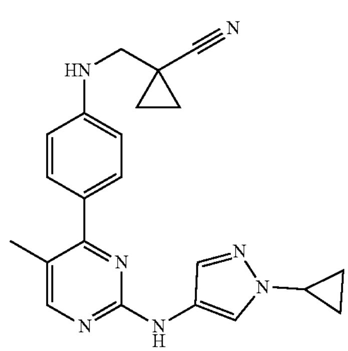 [SMILES: Cc1cnc(Nc2cnn(C3CC3)c2)nc1-c1ccc(NCC2(C#N)CC2)cc1] | 1-(((4-(2-((1-cyclopropyl-1H-pyrazol-4-yl)amino)-5-methylpyrimidin-4-yl)phenyl)amino)methyl)cyclopropanecarbonitrile | 385.46 |

TABLE 1-continued

Summary of Exemplary Structures

| Example | Structure | IUPAC name | Mol Weight |
|---|---|---|---|
| 43 | 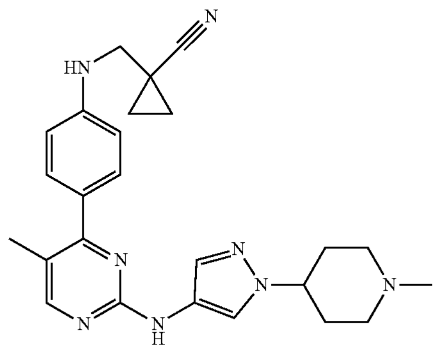 | 1-(((4-(5-methyl-2-((1-(1-methylpiperidin-4-yl)-1H-pyrazol-4-yl)amino)pyrimidin-4-yl)phenyl)amino)methyl)cyclopropane carbonitrile | 442.56 |
| 44 | 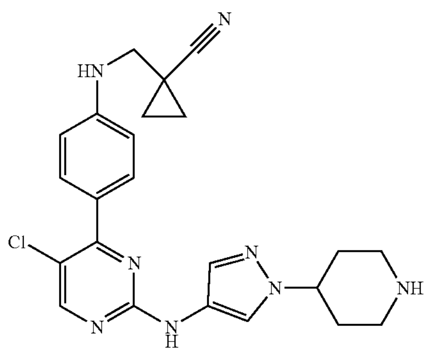 [SMILES: N#CC1(CNc2ccc(-c3nc(Nc4cnn(C5CCNCC5)c4)ncc3Cl)cc2)CC1] | 1-(((4-(5-chloro-2-((1-(piperidin-4-yl)-1H-pyrazol-4-yl)amino)pyrimidin-4-yl)phenyl)amino)methyl)cyclopropane carbonitrile | 448.95 |

TABLE 2

Summary of IC50 (nM)

| Example | JAK1 (5 nM) (1 mM ATP) | JAK2 (0.25 nM) (1 mM ATP) | J2V617F (2.5 nM) (1 mM ATP) | TYK2 (2.5 nM) (1 mM ATP) |
|---|---|---|---|---|
| 1 | 4.8 | 0.27 | 3.1765 | 12 |
| 2 | 72.74 | — | 170.9 | — |
| 3 | 8.862 | — | 28.12 | 21.88 |
| 4 | <2.5 | 0.4254 | <1.25 | <1.25 |
| 5 | 3.325 | — | <1.25 | 3.263 |
| 6 | 7.417 | — | <1.25 | <1.25 |
| 7 | <2.5 | — | <1.25 | <1.25 |
| 8 | 6.197 | — | <1.25 | — |
| 9 | 7.06 | — | <1.25 | — |
| 10 | 124 | — | 113 | — |
| 11 | 65.07 | — | 138.5 | 217.9 |
| 12 | 19.6 | 32.3 | — | 64.73 |
| 13 | 5.578 | — | <1.25 | — |
| 14 | 201.6 | — | 163.4 | 351.4 |
| 15 | 5.712 | — | <1.25 | — |
| 16 | 39.2 | — | 6.33 | — |
| 17 | <2.5 | <0.25 | <1.25 | <1.25 |
| 18 | <2.5 | 0.4273 | — | <1.25 |
| 19 | <2.5 | <0.25 | <1.25 | <1.25 |
| 20 | <2.5 | 0.2513 | — | <1.25 |
| 21 | 7.31 | <0.25 | <1.25 | <1.25 |
| 22 | 136 | — | 56.8 | — |
| 23 | 13.63 | — | <1.25 | — |
| 24 | 84.15 | — | 111 | — |
| 25 | 32.05 | — | 32.05 | — |
| 26 | 6.171 | — | <1.25 | — |
| 27 | 5.528 | — | 1.491 | — |
| 28 | <2.5 | — | <1.25 | — |
| 29 | 14.1 | 3.4 | — | 41.4 |
| 30 | <2.5 | 0.3 | — | — |
| 31 | 7.938 | 3.2 | — | — |
| 32 | 28.9 | 0.9 | — | 106 |
| 33 | 10.84 | <0.25 | 6.163 | 30.04 |
| 34 | 135.9 | 58.84 | — | — |
| 35 | 72.09 | 1.664 | — | — |
| 36 | 103 | 4.6 | — | — |
| 37 | 14.51 | 0.7413 | — | <1.25 |
| 38 | 7.494 | 1.094 | — | 2.617 |
| 39 | <2.5 | 0.3768 | — | <1.25 |
| 40 | <2.5 | 0.6541 | — | 1.785 |
| 41 | 19.64 | 32.33 | — | 64.73 |
| 42 | 19.24 | 27.41 | — | 102.4 |
| 43 | 26.78 | 3.121 | — | 98.45 |
| 44 | 35.25 | 1.457 | — | 173 |

TABLE 3A

| Example | Structure | IUPAC name | Mol. Weight |
|---|---|---|---|
| 45 | 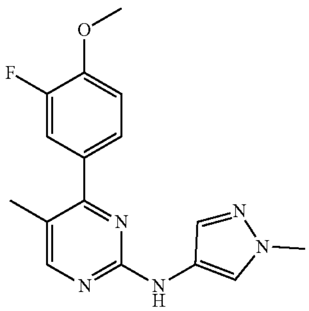 | 4-(3-fluoro-4-methoxyphenyl)-5-methyl-N-(1-methyl-1H-pyrazol-4-yl)pyrimidin-2-amine | 313.33 |
| 46 | 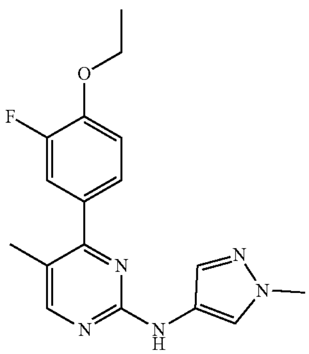 | 4-(4-ethoxy-3-fluorophenyl)-5-methyl-N-(1-methyl-1H-pyrazol-4-yl)pyrimidin-2-amine | 327.36 |
| 47 | 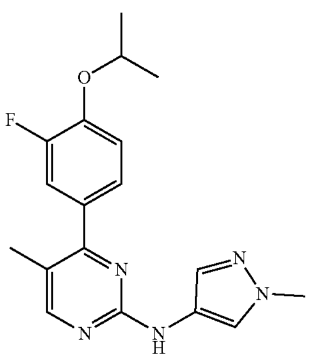 | 4-(3-fluoro-4-isopropoxyphenyl)-5-methyl-N-(1-methyl-1H-pyrazol-4-yl)pyrimidin-2-amine | 341.38 |
| 48 | 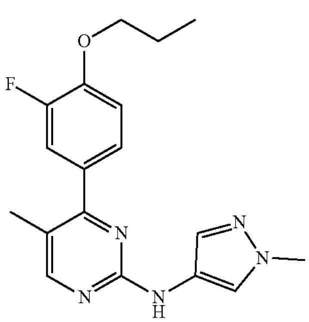 | 4-(3-fluoro-4-propoxyphenyl)-5-methyl-N-(1-methyl-1H-pyrazol-4-yl)pyrimidin-2-amine | 341.38 |

TABLE 3A-continued

Certain Literature Compounds

| Example | Structure | IUPAC name | Mol. Weight |
|---|---|---|---|
| 49 | 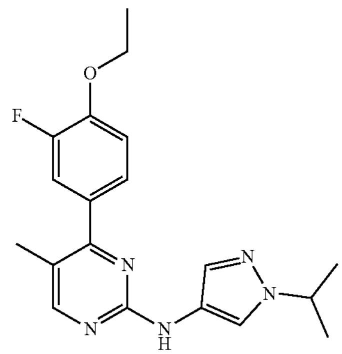 [SMILES: CCOc1ccc(-c2nc(Nc3cnn(C(C)C)c3)ncc2C)cc1F] | 4-(4-ethoxy-3-fluorophenyl)-N-(1-isopropyl-1H-pyrazol-4-yl)-5-methylpyrimidin-2-amine | 355.41 |
| 50 | 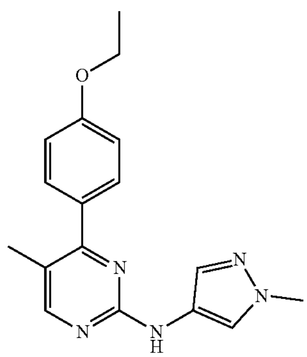 | 4-(4-ethoxyphenyl)-5-methyl-N-(1-methyl-1H-pyrazol-4-yl)pyrimidin-2-amine | 309.36 |

TABLE 3B

Exemplary Testing Data of Literature Compounds

| Example | JAK1 (5 nM) (1 mM ATP) | JAK2 (0.25 nM) (1 mM ATP) | J2V617F (2.5 nM) (1 mM ATP) | TYK2 (2.5 nM) (1 mM ATP) |
|---|---|---|---|---|
| 45 | 109.9 | 121.5 | 206.1 | — |
| 46 | 40.63 | 60.63 | 86.27 | 74.86 |
| 47 | 48.61 | 61.3 | 84.18 | — |
| 48 | 25.7 | 39.63 | 59.98 | — |
| 49 | 52.58 | 80.7 | 103.3 | 41.25 |
| 50 | 150.5 | 200.6 | 342.6 | 157.1 |

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A compound having the structural formula (I):

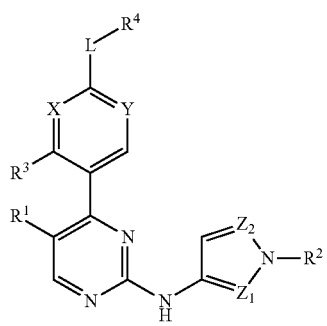

wherein
L is O;
X is $CR^x$, wherein $R^x$ is H or F;
Y is CH;
$Z_1$ is CH;
$Z_2$ is N;
$R^1$ is H, F, Cl or methyl;
$R^2$ is a $C_1$-$C_6$ aliphatic group;
$R^3$ is H; and
$R^4$ is a $C_{2-5}$ alkyl group substituted with CN, optionally comprises a 3- or 4-membered ring,
or a pharmaceutically acceptable form or an isotope derivative thereof.

2. The compound of claim 1, wherein $R^x$ is H.
3. The compound of claim 1, wherein $R^x$ is F.
4. The compound of claim 1, wherein $R^4$ comprises a 3-membered ring.
5. The compound of claim 1, wherein $R^4$ comprises a 4-membered ring.
6. The compound of claim 1, wherein $R^1$ is H.
7. The compound of claim 1, wherein $R^1$ is F.
8. The compound of claim 1, wherein $R^1$ is Cl.
9. The compound of claim 1, wherein $R^1$ is methyl.
10. The compound of claim 1, wherein $R^2$ comprises a $C_3$ cyclic alkyl.
11. A compound selected:

| Example | Structure | IUPAC name |
|---|---|---|
| 1 | 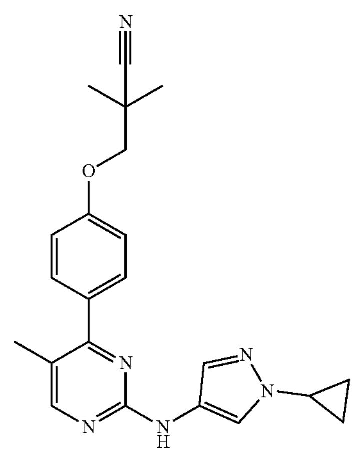 [SMILES: Cc1cnc(Nc2cnn(C3CC3)c2)nc1-c1ccc(OCC(C)(C)C#N)cc1] | 3-(4-(2-((1-cyclopropyl-1H-pyrazol-4-yl)amino)-5-methylpyrimidin-4-yl)phenoxy)-2,2-dimethylpropanenitrile |
| 2 | 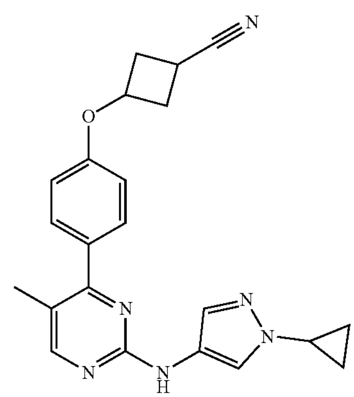 [SMILES: Cc1cnc(Nc2cnn(C3CC3)c2)nc1-c1ccc(OC2CC(C#N)C2)cc1] | 3-(4-(2-((1-cyclopropyl-1H-pyrazol-4-yl)amino)-5-methylpyrimidin-4-yl)phenoxy)cyclobutanecarbonitrile |

-continued

| Example | Structure | IUPAC name |
|---|---|---|
| 3 | 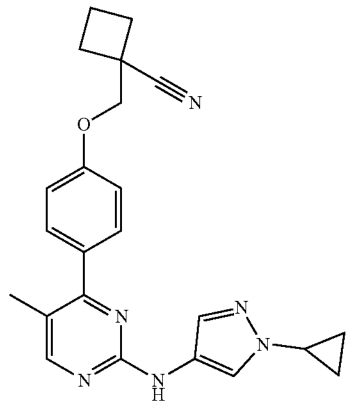 [SMILES: Cc1cnc(Nc2cnn(C3CC3)c2)nc1-c1ccc(OCC2(C#N)CCC2)cc1] | 1-((4-(2-((1-cyclopropyl-1H-pyrazol-4-yl)amino)-5-methylpyrimidin-4-yl)phenoxy)methyl)cyclobutanecarbonitrile |
| 4 | 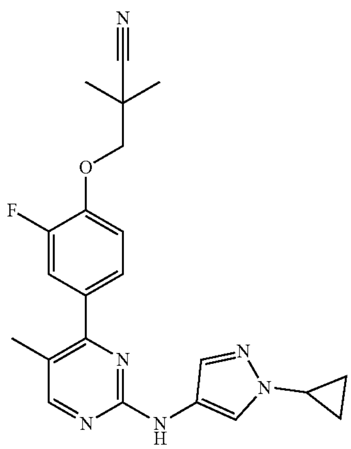 [SMILES: Cc1cnc(Nc2cnn(C3CC3)c2)nc1-c1ccc(OCC(C)(C)C#N)c(F)c1] | 3-(4-(2-((1-cyclopropyl-1H-pyrazol-4-yl)amino)-5-methylpyrimidin-4-yl)-2-fluorophenoxy)-2,2-dimethylpropanenitrile |
| 5 | 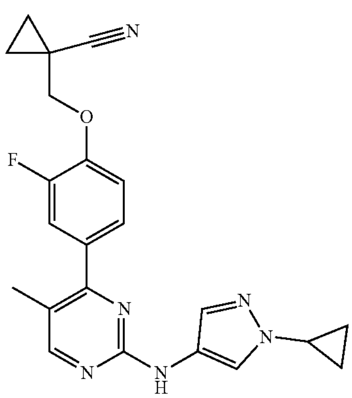 | 1-((4-(2-((1-cyclopropyl-1H-pyrazol-4-yl)amino)-5-methylpyrimidin-4-yl)-2-fluorophenoxy)methyl)cyclopropanecarbonitrile |
| 12 | 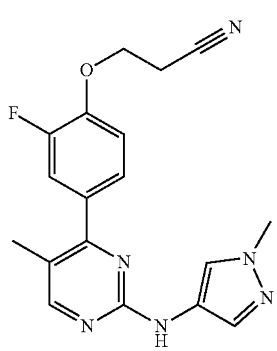 | 3-(2-fluoro-4-(5-methyl-2-((1-methyl-1H-pyrazol-4-yl)amino)pyrimidin-4-yl)phenoxy)propanenitrile |

| Example | Structure | IUPAC name |
|---|---|---|
| 24 | 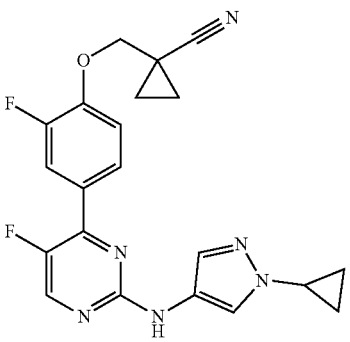 [SMILES: N#CC1(COc2ccc(-c3nc(Nc4cnn(C5CC5)c4)ncc3F)cc2F)CC1] | 1-((4-(2-((1-cyclopropyl-1H-pyrazol-4-yl)amino)-5-fluoropyrimidin-4-yl)-2-fluorophenoxy)methyl)cyclopropanecarbonitrile |
| 27 | 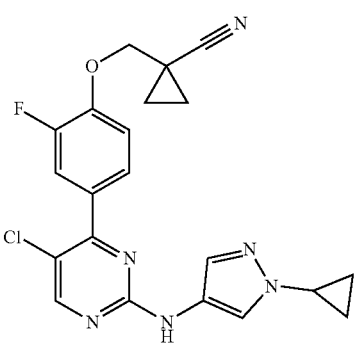 [SMILES: N#CC1(COc2ccc(-c3nc(Nc4cnn(C5CC5)c4)ncc3Cl)cc2F)CC1] | 1-((4-(5-chloro-2-((1-cyclopropyl-1H-pyrazol-4-yl)amino)pyrimidin-4-yl)-2-fluorophenoxy)methyl)cyclopropanecarbonitrile |
| 29 | 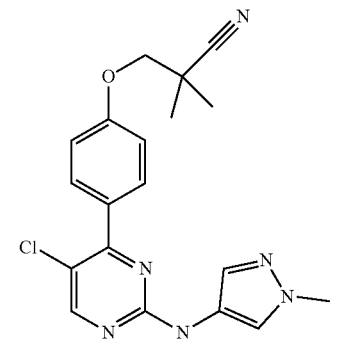 | 3-(4-(5-chloro-2-((1-methyl-1H-pyrazol-4-yl)amino)pyrimidin-4-yl)phenoxy)-2,2-dimethylpropanenitrile |
| 32 | 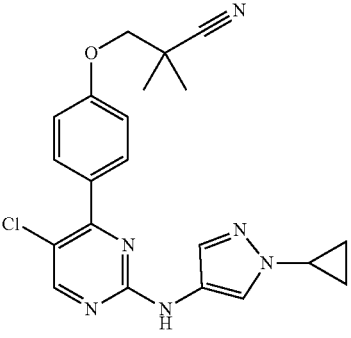 [SMILES: CC(C)(C#N)COc1ccc(-c2nc(Nc3cnn(C4CC4)c3)ncc2Cl)cc1] | 3-(4-(5-chloro-2-((1-cyclopropyl-1H-pyrazol-4-yl)amino)pyrimidin-4-yl)phenoxy)-2,2-dimethylpropanenitrile |

| Example | Structure | IUPAC name |
| --- | --- | --- |
| 38 | 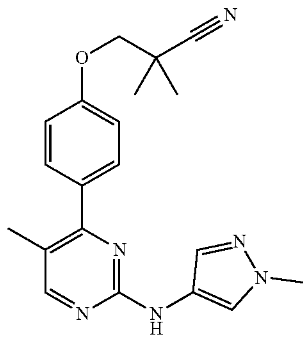 | 2,2-dimethyl-3-(4-(5-methyl-2-((1-methyl-1H-pyrazol-4-yl)amino)pyrimidin-4-yl)phenoxy )propanenitrile |
| 40 | 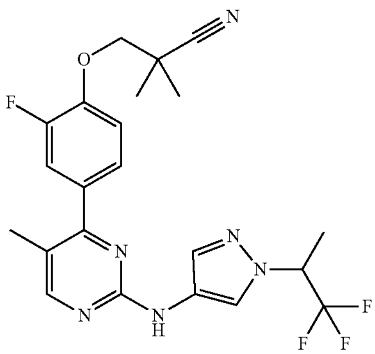 [SMILES: Cc1cnc(Nc2cnn(C(C)C(F)(F)F)c2)nc1-c1ccc(OCC(C)(C)C#N)c(F)c1] | 3-(2-fluoro-4-(5-methyl-2-((1-(1,1,1-trifluoropropan-2-yl)-1H-pyrazol-4-yl)amino)pyrimidin-4-yl)phenoxy)-2,2-dimethylpropanenitrile |
| 41 | 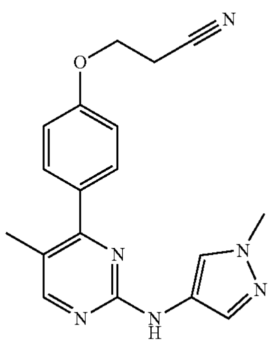 | 3-(4-(5-methyl-2-((1-methyl-1H-pyrazol-4-yl)amino)pyrimidin-4-yl)phenoxy)propanenitrile |

12. A pharmaceutical composition comprising a compound according to claim 1, and a pharmaceutically acceptable excipient, carrier, or diluent.

13. A pharmaceutical composition comprising a compound of claim 11.

* * * * *